(12) United States Patent
Niederweis et al.

(10) Patent No.: US 12,312,385 B2
(45) Date of Patent: *May 27, 2025

(54) MSP NANOPORES AND USES THEREOF

(71) Applicant: THE UAB RESEARCH FOUNDATION, Birmingham, AL (US)

(72) Inventors: Michael Niederweis, Homewood, AL (US); Mikhail Pavlenok, Birmingham, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/516,332

(22) Filed: Nov. 21, 2023

(65) Prior Publication Data

US 2024/0174721 A1    May 30, 2024

Related U.S. Application Data

(60) Continuation of application No. 17/674,140, filed on Feb. 17, 2022, now Pat. No. 11,858,966, which is a continuation of application No. 16/997,032, filed on Aug. 19, 2020, now Pat. No. 11,292,817, which is a division of application No. 15/304,183, filed as application No. PCT/US2015/026239 on Apr. 16, 2015, now Pat. No. 10,781,237.

(60) Provisional application No. 61/980,415, filed on Apr. 16, 2014, provisional application No. 61/980,393, filed on Apr. 16, 2014.

(51) Int. Cl.
| | | |
|---|---|---|
| C07K 14/35 | (2006.01) | |
| C12Q 1/6869 | (2018.01) | |
| G01N 27/447 | (2006.01) | |
| G01N 33/487 | (2006.01) | |

(52) U.S. Cl.
CPC ............ *C07K 14/35* (2013.01); *C12Q 1/6869* (2013.01); *G01N 27/44743* (2013.01); *G01N 27/44756* (2013.01); *G01N 33/48721* (2013.01)

(58) Field of Classification Search
CPC .................................................... C07K 14/35
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,267,872 B1 | 7/2001 | Akeson et al. | |
| 6,362,002 B1 | 3/2002 | Denison et al. | |
| 6,406,880 B1 | 6/2002 | Thornton | |
| 6,428,959 B1 | 8/2002 | Deamer | |
| 6,617,113 B2 | 9/2003 | Deamer | |
| 6,673,615 B2 | 1/2004 | Denison et al. | |
| 6,746,594 B2 | 6/2004 | Akeson et al. | |
| 6,936,433 B2 | 8/2005 | Akeson et al. | |
| 7,189,503 B2 | 3/2007 | Akeson et al. | |
| 7,238,485 B2 | 7/2007 | Akeson et al. | |
| 7,444,053 B2 | 10/2008 | Schmidt et al. | |
| 7,713,544 B2 | 5/2010 | Chaikof et al. | |
| 8,673,550 B2 | 3/2014 | Gundlach et al. | |
| 9,170,230 B2 | 10/2015 | Gundlach et al. | |
| 9,534,024 B2 | 1/2017 | Gundlach et al. | |
| 9,624,275 B2 | 4/2017 | Gundlach et al. | |
| 10,781,237 B2 | 9/2020 | Niederweis et al. | |
| 11,292,817 B2 | 4/2022 | Niederweis et al. | |
| 11,858,966 B2 | 1/2024 | Niederweis et al. | |
| 2006/0063171 A1 | 3/2006 | Akeson et al. | |
| 2007/0190542 A1 | 8/2007 | Ling et al. | |
| 2007/0269843 A1 | 11/2007 | Thornton | |
| 2009/0298072 A1 | 12/2009 | Ju | |
| 2017/0218443 A1 | 8/2017 | Gundlach et al. | |

FOREIGN PATENT DOCUMENTS

| | | |
|---|---|---|
| JP | 07248329 A | 9/1995 |
| WO | 0116327 A2 | 3/2001 |
| WO | 0116328 A2 | 3/2001 |
| WO | 2004032511 A1 | 4/2004 |
| WO | 2006028508 A2 | 3/2006 |
| WO | 2009044170 A1 | 4/2009 |
| WO | 2010034018 A2 | 3/2010 |
| WO | 2011106456 A2 | 9/2011 |
| WO | 2012107778 A2 | 8/2012 |
| WO | 2015166275 A1 | 11/2015 |

OTHER PUBLICATIONS

CA Patent Application No. 3207570, Office Action, Aug. 12, 2024, 5 pages.
WO 2012/107778, filed Feb. 11, 2011 (priority date), by ONT entitled "Mutant Pores," exhibit submitted Jun. 29, 2015, in support of Patent Owners' Supplemental Response for U.S. Patent Trial and Appeal Board, Case No. IPR2014-00513, Aug. 16, 2012, 103 pages.
International Publication No. WO 2015/110813 A1, Southern District of California, Case No. 3:16-cv-00477-LAB-MDD, as exhibit 21, and cited in International Trade Commission, Investigation No. 337-3123,, Jul. 30, 2015, 113 pages.
Petitioner's Reply to Patent Owners' Response, in U.S. Patent Trial and Appeal Board Case No. IPR2014-00513, *Oxford Nanopore Technologies, Ltd. v. The University of Washington and the UAB Research Foundation*, served Mar. 11, 2015, 20 pages.
Complaint of Illumina, Inc., et al., Under Section 337 of the Tariff Act of 1930, as Amended, submitted in U.S. International Trade Commission, Investigation No. 337-3123, in the Matter of Certain Nanopores and Products containing Same, Feb. 23, 2016, 39 pages.
Complainants' Statement on the Public Interest, submitted in U.S. International Trade Commission, Investigation No. 37-3123, in the Matter of Certain Nanopores and Products Containing Same, Feb. 23, 2016, 5 pages.

(Continued)

*Primary Examiner* — Albert M Navarro
(74) *Attorney, Agent, or Firm* — Kilpatrick Townsend & Stockton LLP

(57) ABSTRACT

Provided herein are mutant single-chain *Mycobacterium smegmatis* porin (Msp) and uses thereof.

9 Claims, 27 Drawing Sheets

Specification includes a Sequence Listing.

(56) References Cited

OTHER PUBLICATIONS

Declaration of Jennifer Harris, exhibit in U.S. Patent Trial and Appeal Board Case No. IPR2014-00513, *Oxford Nanopore Technologies Ltd.* v. *University of Washington and UAB Research Foundation*, Dec. 11, 2014, 6 pages.
Deposition of Steven Benner, Ph.D., taken Jul. 31, 2015, Exhibit 1058 Submitted Aug. 28, 2015, in *Oxford Nanopore Technologies Ltd.* v. *University of Washington and UAB Research Foundation*, Before the U.S. Patent Trial and Appeal Board, 69 pages.
Joint List of Disputed Claim Terms and Proposed Constructions, submitted in U.S. International Trade Commission, Investigation No. 337-TA-991, in the Matter of Certain Nanopores and Products Containing Same, Jun. 10, 2016, 8 pages.
Patent Owners' Demonstratives for Oral Argument in U.S. Patent Trial and Appeal Board, Case No. IPR2014-00513, *Oxford Nanopore Technologies, Ltd.* v. *The University of Washington and the UAB Research Foundation*, Dec. 3, 2015, 89 pages.
WO 2013/098562, filed Dec. 29, 2011 (priority date), by ONT entitled "Enzyme Method", Jul. 4, 2013, 89 pages.
Declaration of Daniel Branton, exhibit cited in U.S. Patent Trial and Appeal Board Case No. IPR2015-00057, Oct. 11, 2014, 91 pages.
International Publication No. WO 2015/110777 A1, cited in U.S. D.C., Southern District of California, Case No. 3:16-cv-00477-LAB-MDD, as exhibit 21, and cited in International Trade Commission, investigation No. 337-3123, Jul. 30, 2015, 92 pages.
WO 2014/135838, filed Mar. 8, 2013 (priority date), by ONT entitled "Enzyme Stalling Method," exhibit submitted Jun. 29, 2015, in support of Patent Owners' Supplemental Response for U.S. Patent Trial and Appeal Board, Sep. 12, 2014, 109 pages.
Project Information Page for Project No. 1 R21 HG004145 01: http://projectreporter.nih.gov/project_info_details.cfm?aid=7192749 &icde=22969799 [retrieved Jan. 20, 2015, 1 page.
WO 2013/057495, filed Oct. 21, 2011 (priority date), by ONT entitled "Method of Characterizing a Target Polynucleotide Using a Pore and a hel308 Helicase", Apr. 25, 2013, 110 pages.
WO 2015/056028, filed Oct. 18, 2013 (priority date), by ONT entitled Method of Characterizing a Target Ribonucleic Acid (RNA) Comprising Forming a Complementary Polynucleolide Which Moves Through a Transmembrane Pore, Apr. 23, 2015, 67 pages.
WO 2015/055981, filed Oct. 18, 2013 (priority date), by ONT entitled "Modified Enzymes," exhibit submitted Jun. 29, 2015, in support of Patent Owners' Supplemental Response for U.S. Patent Trial and Appeal Board, Case No. IPR2014-00513, 146 pages.
WO 2013/014451, filed Jul. 25, 2011 (priority date), by ONT entitled "Hairpin Loop Method for Double Strand Polynucleotide Sequencing Using Transmembrane Pores," exhibit submitted Jun. 29, 2015, in support of Patent, Jan. 31, 2013, 92 pages.
"2007 Amgen Faculty", Exhibit 5 to the Deposition of Jennifer Harris in U.S. Patent Trial and Appeal Board Case No. IPR2014-00513, *Oxford Nanopore Technologies Ltd.* v. *The University of Washington and the UAB Research Foundation*, Feb. 3, 2015, 7 pages.
"2007 Amgen Scholars", Exhibit 6 to the Deposition of Jennifer Harris in U.S. Patent Trial and Appeal Board Case No. IPR2014-00513, *Oxford Nanopore Technologies, Ltd.* v. *The University of Washington and the UAB Research Foundation*, Feb. 3, 2015, 6 pages.
"About the Amgen Scholars Program", Exhibit 4 to the Deposition of Jennifer Harris in U.S. Patent Trial and Appeal Board Case No. IPR2014-00513, *Oxford Nanopore Technologies, Ltd.* v. *The University of Washington and the UAB Research Foundation,*, Jun. 18-Aug. 17, 2007, 1 page.
"Analytical ESI-MS Report by Integrated DNA Technologies", Exhibit 1053 in U.S. Patent Trial and Appeal Board Case No. IPR2014-00513, *Oxford Nanopore Technologies, Ltd.* v. *The University of Washington and the UAB Research Foundation*, Apr. 1, 2015, 1 page.

"Analyze", Definition of Analyse at Dictionary.com, Exhibit cited in U.S. Patent Trial and Appeal Board Case No. IPR2014-00513, Available Online at: <http:/dictionary.reference.com/browse/analyse?s=t>, Accessed from Internet on: Nov. 25, 2020, 4 pages.
"Case No. IPR2014-00512", Decision in U.S. Patent Trial and Appeal Board, *Oxford Nanopore Technologies, Ltd.* v. *University of Washington and UAB Research Foundation*, Sep. 15, 2014, 22 pages.
"Case No. IPR2014-00512 and case No. IPR2014-0051", Declaration of Daniel Branton, exhibit cited in U.S. Patent Trial and Appeal Board, Mar. 18, 2014, 236 pages.
"Case No. IPR2014-00512 and Case No. IPR2014-00513", ProQuest response to e-mail inquiry re Thomas Butler's dissertation, exhibit cited in U.S. Patent Trial and Appeal Board, Nov. 4, 2013, 1 page.
"Case No. IPR2014-00512 and case No. IPR2014-00513", Declaration of Roland Benz, exhibit cited in U.S. Patent Trial and Appeal Board, Mar. 17, 2014, 124 pages.
"Case No. IPR2014-00513", Jennifer Harris, Exhibit 1048, submitted Mar. 11, 2015, in support of Petitioner's Reply to Patent Owners' Response in U.S. Patent Trial and Appeal Board, Aug. 14, 2007, 1 page.
"Case No. IPR2014-00513", Jennifer Harris , Exhibit 1049, submitted Mar. 11, 2015, in support of Petitioner's Reply to Patent Owners' Response in U.S. Patent Trial and Appeal Board, Aug. 16, 2007, 1 page.
"Case No. IPR2014-00513", Sanghera, G., exhibit submitted in support of Patent Owners' Supplemental Response for U.S. Patent Trial and Appeal Board, *Oxford Nanopore Technologies, Ltd.* v. *The University of Washington and UAB Research Foundation*, Feb. 4, 2011, 1 page.
"Case No. IPR2014-00513", Declaration of Daniel Branton, Exhibit 1044 in U.S. Patent Trial and Appeal Board, *Oxford Nanopore Technologies, Ltd.* v. *University of Washington and the UAB Research Foundation*, Mar. 11, 2015, 16 pages.
"Case No. IPR2014-00513", Deposition Upon Oral Examination of Daniel Branton in U.S. Patent Trial and Appeal Board, *Oxford Nanopore Technologies, Ltd.* v. *The University of Washington and the UAB Research Foundation*, Apr. 15, 2015, 165 pages.
"Case No. IPR2014-00513", Jennifer Harris, Exhibit 1046, submitted Mar. 11, 2015, in support of Petitioner's Reply 48 to Patent Owners' Response in U.S. Patent Trial and Appeal Board, Oxford Nanopore Technologies, Aug. 14, 2007, 2 pages.
"Case No. IPR2014-00513", Jennifer Harris , Exhibit 1047, submitted Mar. 11, 2015, in support of Petitioner's Reply to Patent Owners' Response in U.S. Patent Trial and Appeal Board, Aug. 8, 2007, 2 pages.
"Case No. IPR2014-00513", Willcocks, S., exhibit submitted Jun. 29, 2015, in support of Patent Owners' Supplemental Response for U.S. Patent Trial and Appeal Board, *Oxford Nanopore Technologies, Ltd.* v. *University of Washington and UAB Research Foundation*, Jul. 1, 2009, 2 pages.
"Case No. IPR2014-00513", Declaration, exhibit submitted Jun. 29, 2015, in support of Patent Owners' Supplemental Response for U.S. Patent Trial and Appeal Board, *Oxford Nanopore Technologies, Ltd.* v. *University of Washington and UAB Research Foundation*, Jun. 26, 2015, 22 pages.
"Case No. IPR2014-00513", Notice of Deposition of Jennifer Harris, Exhibit 1 to the Deposition of Jennifer Harris in U.S. Patent Trial and Appeal Board, *Oxford Nanopore Technologies, Ltd.* v. *The University of Washington and the UAB Research Foundation*, Jan. 26, 2015, 3 pages.
"Case No. IPR2014-00513", Decision in U.S. Patent Trial and Appeal Board, *Oxford Nanopore Technologies, Ltd.* v. *University of Washington and UAB Research Foundation*, Sep. 15, 2014, 30 pages.
"Case No. IPR2014-00513", Decision Granting Petitioner's Motion for Joinder and Instituting Inter Partes Review, 37 C.F.R. §§ 42.108, 42.122, U.S. Patent Trial and Appeal Board, Apr. 27, 2015, 31 pages.
"Case No. IPR2014-00513", Petitioners Reply to Patent Owners' Supplemental Response in U.S. Patent Trial and Appeal Board, *Oxford Nanopore Technologies, Ltd.* v. *University of Washington and UAB Research Foundation*, Aug. 28, 2015, 32 pages.

(56) References Cited

OTHER PUBLICATIONS

"Case No. IPR2014-00513", Declaration of Steven A. Benner, Ph.D., exhibit in U.S. Patent Trial and Appeal Board, *Oxford Nanopore Technologies, Ltd.* v. *University of Washington and UAB Research Foundation*, Dec. 11, 2014, 33 pages.
"Case No. IPR2014-00513", Deposition of Steven A. Benner, Exhibit 1042 to U.S. Patent Trial and Appeal Board , *Oxford Nanopore Technologies, Ltd.* v. *The University of Washington and the UAB Research Foundation*,, Feb. 12, 2015, 36 pages.
"Case No. IPR2014-00513", Order: Conduct of the Proceeding: 37 C.F.R. § 42.5, U.S. Patent Trial and Appeal Board Paper No. 25, in U.S. Patent Trial and Appeal Board, Feb. 19, 2015, 5 pages.
"Case No. IPR2014-00513", Abstract Listing, Exhibit 8 to the Deposition of Jennifer Harris in U.S. Patent Trial and Appeal Board, *Oxford Nanopore Technologies, Ltd.* v. *The University of Washington and the UAB Research Foundation*, Feb. 3, 2015, 5 pages.
"Case No. IPR2014-00513", Maria Vignone of the U.S. Patent Trial and Appeal Board in U.S. Patent Trial and Appeal Board, *Oxford Nanopore Technologies, Ltd.* v. *The University of Washington and the UAB Research Foundation*, Mar. 4, 2015, 5 pages.
"Case No. IPR2014-00513", Petitioner's Demonstratives for Oral Argument in U.S. Patent Trial and Appeal Board, *Oxford Nanopore Technologies, Ltd.* v. *The University of Washington and the UAB Research Foundation*, Dec. 3, 2015, 53 pages.
"Case No. IPR2014-00513", Final Written Decision in U.S. Patent Trial and Appeal Board, *Oxford Nanopore Technologies, Ltd.* v. *The University of Washington and the UAB Research Foundation*, Feb. 26, 2016, 58 pages.
"Case No. IPR2014-00513", Patent Owners' Supplemental Response in U.S. Patent Trial and Appeal Board, *Oxford Nanopore Technologies, Ltd.* v. *University of Washington and UAB Research Foundation*, Jun. 29, 2015, 60 pages.
"Case No. IPR2014-00513", Patent Owners' Motion to Amend in U.S. Patent Trial and Appeal Board, *Oxford Nanopore Technologies, Ltd.* v. *University of Washington and UAB Research Foundation*, Dec. 11, 2014, 7 pages.
"Case No. IPR2014-00513", Deposition Upon Oral Examination of Jennifer Harris, Exhibit 1045 to U.S. Patent Trial and Appeal Board, *Oxford Nanopore Technologies, Ltd.* v. *The University of Washington and the UAB Research oundation*,, Feb. 3, 2015, 75 pages.
"Case No. IPR2014-00513", Supplemental Declaration of Daniel Branton, Exhibit 1052 in U.S. Patent Trial and Appeal Board, *Oxford Nanopore Technologies, Ltd.* v. *The University of Washington and the UAB Research Foundation*, Apr. 1, 2015, 9 pages.
"Case No. IPR2014-00513", Record of Oral Hearing held in U.S. Patent Trial and Appeal Board, *Oxford Nanopore Technologies, Ltd.* v. *The University of Washington and the UAB Research Foundation*, Jan. 4, 2016, 90 pages.
"Case No. IPR2014-00513", Willcocks, S., exhibit submitted Jun. 29, 2015, in support of Patent Owners' Supplemental Response for U.S. Patent Trial and Appeal Board, Apr. 10, 2009, 3 pages.
"Case No. IPR2014-00513", Patent Owners' Response in U.S. Patent Trial and Appeal Board, *Oxford Nanopore Technologies, Ltd.* v. *University of Washington and UAB Research Foundation*, Dec. 11, 2014, 33 pages.
"Case No. IPR2015-00027", Patent Owners' Preliminary Response in U.S. Patent Trial and Appeal Board, *Oxford Nanopore Technologies, Ltd.* v. *University of Washington and UAB Research Foundation*, Jan. 29, 2015, 34 pages.
"Case No. IPR2015-00057", U.S. Pat. No. 8,673,550, Motion for Joinder and/or Consolidation With Related Instituted Inter Partes Review to the U.S. Patent Trial and Appeal Board, Oct. 13, 2014, 11 pages.
"Case No. IPR2015-00057", Declaration of James Willcocks, exhibit cited in U.S. Patent Trial and Appeal Board, Oct. 13, 2014, 4 pages.
"Case No. IPR2015-00057", Declaration of Roland Benz, exhibit cited in U.S. Patent Trial and Appeal Board, Oct. 13, 2014, 71 pages.
"Certain Nanopores and Products Containing Same", Response of Oxford Nanopore Technologies Ltd. and Oxford Nanopore Technologies, Inc. to the Complaint of Illumina, Inc, Apr. 25, 2016, 99 pages.
"Complaint for Patent Infringement", submitted in U.S.D.C., Southern District of California, Case No. 3:16-cv-00477-AB-MDD, *Illumina, Inc.*, et al. v. *Oxford Nanopore Technologies*, Feb. 23, 2016, 14 pages.
"Declaration of Lindsey Miles", May 27, 2014, 3 pages.
"DNA Sequencing—The Hole Story: Nanopores May Lead the Way to a New Generation of Sequencing", The Economist, Oct. 16, 2008, pp. 1-2.
"First Year Amgen Scholars and Leading Scientists Attend Symposium to Explore Drug Discovery & Development", News Release, Available on Internet at: http://www.amgen.com/media/media_pr_detail.jsp?releaseiD=1037887, Aug. 7, 2007, 3 pages.
"Funding Opportunity Announcement for RFA-HG-05-004", Exhibit Cited in Patent Owners' Preliminary Response in U.S. Patent Trial and Appeal Board Case No. IPR2015-00057, Accessed from Internet on Jan. 20, 2015, 23 pages.
"Licensing Deal Marks Coming of Age for UAB-UW Nanopore Sequencing Technology", Press Release, UAB News, Available Online at: http://www.uab.news/innovation/item/3847-licensing-deal-marks-coming-of-age-for-uab-uw-nanopore-sequencing-echnology.html, Accessed from internet on: Mar. 13, 2014, 4 pages.
"National Human Genome Research Institute Response to Baker Botts LLP Freedom of Information Act Request", exhibit cited in U.S. Patent Trial and Appeal Board Case No. IPR2014-00512 and Case No. IPR2014-00513, Dec. 13, 2013, 1 page.
"National Institutes of Health Public Health Service Grant Instructions", Exhibit Cited in U.S. Patent Trial and Appeal Board Case No. IPR2015-00057, Sep. 2004, 66 pages.
"Page and HPLC Purification", Available Online at: http://www.idtdna.com/pages/products/dna-rna/hplc-page, Accessed from internet on Feb. 9, 2015, 2 pages.
"Pamphlet of University of Washington Summer Research Poster Session", Exhibit in U.S. Patent Trial and Appeal Board Case No. IPR2014-00513, *Oxford Nanopore Technologies, Ltd.* v. *University of Washington and UAB Research Foundation*, Aug. 16, 2007, 56 pages.
"Purification of Oligonucleotides", Quick Look Version of the Full Technical Report Chemical Synthesis of Olligonucleotides, Integrated DNA Technologies, Exhibit 1051, 2009 and 2011, 3 pages.
"Respondents Oxford Nanopore Technologies Ltd. and Oxford Nanopore Technologies, Inc.'s Notice of Prior Art, Submitted in U.S. International Trade Commission", Investigation No. 337-TA-991, in the Matter of Certain Nanopores and Products Containing Same, May 27, 2016, 15 pages.
"The Smartest Company in the World. And It's Not Google", MIT Technology Review, exhibit in support of Patent Owners' Supplemental Response for U.S. Patent Trial and Appeal Board, Case No. IPR2014-00513, Mar./Apr. 2014, 6 pages.
"Through Constriction to a Wide Open Frontier", University of Washington Physics Newsletter, vol. 15, No. 6, Nov. 2007, 1 page.
"University of Washington Receives $1 Million Grant From Amgen Foundation for Undergraduate Science Research Program", Press release, Oct. 16, 2006, 3 pages.
"University of Washington Response to Baker Botts LLP", Public Records Request PR-2014-00281(Stage 1), and Jens Gundlach May 5, 2011 Email, Exhibit 1050, submitted Mar. 11, 2015, in support of Petitioners Reply to Patent Owners' Response in U.S. Patent Trial and Appeal Board Case No. IPR2014-00513, Nov. 18, 2014, 3 pages.
U.S. Appl. No. 13/069,187, "Correspondence With U.S. Patent and Trademark Office,", exhibit cited in U.S. PatentTrial and Appeal Board Case No. IPR2015-00057, Mar. 22, 2011, 119.
U.S. Appl. No. 15/304,183, "Advisory Action", Mar. 26, 2020, 2 pages.
U.S. Appl. No. 15/304,183, "Advisory Action", Apr. 30, 2019, 6 pages.
U.S. Appl. No. 15/304,183, "Advisory Action", May 21, 2020, 7 pages.

(56) References Cited

OTHER PUBLICATIONS

U.S. Appl. No. 15/304,183, "Advisory Action", Jun. 3, 2019, 8 pages.
U.S. Appl. No. 15/304,183, "Final Office Action", Dec. 20, 2019, 8 pages.
U.S. Appl. No. 15/304,183, "Final Office Action", Jan. 14, 2019, 9 pages.
U.S. Appl. No. 15/304,183, "Non-Final Office Action", Jun. 7, 2018, 17 pages.
U.S. Appl. No. 15/304,183, "Non-Final Office Action", Jun. 25, 2019, 5 pages.
U.S. Appl. No. 15/304,183, "Notice of Allowance", Jun. 17, 2020, 7 pages.
U.S. Appl. No. 15/304,183, "Restriction Requirement", Oct. 16, 2017, 6 pages.
U.S. Appl. No. 16/997,032, "Non-Final Office Action", Jun. 29, 2021, 5 pages.
U.S. Appl. No. 16/997,032, "Notice of Allowance", Nov. 23, 2021, 6 pages.
U.S. Appl. No. 17/674,140, "Non-Final Office Action", May 15, 2023, 8 pages.
U.S. Appl. No. 17/674,140, "Notice of Allowance", Aug. 30, 2023, 5 pages.
U.S. Appl. No. 61/098,938, "U.S. Provisional Application No.", Sep. 22, 2008, 33 pages.
Akeson et al., "Microsecond Time-Scale Discrimination Among Polycytidylic Acid, Polyadenylic Acid, and Polyuridylic Acid as Homopolymers or as Segments Within Single RNA Molecules", Biophysical Journal, vol. 77, No. 6, Dec. 1999, pp. 3227-3233.
Ball, "Ion Channel Gating and DNA Translocation in Single MspA Protein Pores", University of Washington Physics REU (Research Experiences for Undergraduates) Summer Research Program, manuscript and presentation slides,, 2006, 25 pages.
Baumann et al., "Forced Subunit Assembly in $\alpha 1\beta 2\gamma 2$ Receptors", Journal of Biological Chemistry, vol. 277, No. 48, Nov. 2002, pp. 46020-46025.
Bayley et al., "Functional Engineered Channels and Pores (Review)", Molecular Membrane Biology, vol. 21, No. 4, Jul.-Aug. 2004, pp. 209-220.
Bayley, "Nanopore Sequencing: From Imagination to Reality", Clinical Chemistry, vol. 61, No. 1, Jan. 2015, pp. 25-31.
Bayley et al., "Stochastic Sensors Inspired by Biology", Nature, vol. 413, No. 6852, Sep. 2001, pp. 226-230.
Benner et al., "Sequence-Specific Detection of Individual DNA Polymerase Complexes in Real Time Using a Nanopore", Nature Nanotechnology, vol. 2, No. 11, Nov. 2007, pp. 718-724.
Berkane et al., "Nanopores: Maltoporin Channel as a Sensor for Maltodextrin and Lambda-Phage", Journal of Nanobiotechnology, vol. 3, No. 1, Mar. 2, 2005, pp. 1-6.
Bossman et al., "Nanotechnology on Surfaces Using Mutants of MspA from *Mycobacterium smegmatis*", Abstract 66, the 41st Midwest Regional Meeting, Available Online at: http://acs.confex.com/acs/mwrm06techprogram/P38604.HTM, Oct. 25-27, 2006, 1 page.
Branton, "Case No. IPR2014-00513", exhibit submitted Jun. 29, 2015, in support of Patent Owners' Supplemental Response for U.S. Patent Trial and Appeal Board,, *Oxford Nanopore Technologies, Ltd. v. University of Washington and UAB Research Foundation*, Jul. 28, 2008, 30 pages.
Branton, "Case No. IPR2014-00513", exhibit submitted Jun. 29, 2015, in support of Patent Owners' Supplemental Response for U.S. Patent Trial and Appeal Board, *Oxford Nanopore Technologies, Ltd. v. University of Washington and UAB Research Foundation*, Jul. 30, 2008, 4 pages.
Branton et al., "The Potential and Challenges of Nanopore Sequencing", Nature Biotechnology, vol. 26, No. 10, Oct. 9, 2008, pp. 1146-1153.
Branton, "Transcript of Deposition", exhibit submitted Jun. 29, 2015, in support of Patent Owners' Supplemental Response for U.S. Patent Trial and Appeal Board, Case No. IPR2014-00513, *Oxford Nanopore Technologies, Ltd. v. University of Washington and UAB Research Foundation*, Apr. 15, 2015, 165 pages.
Branton, "Transcript of Deposition", exhibit submitted Jun. 29, 2015, in support of Patent Owners' Supplemental Response for U.S. Patent Trial and Appeal Board, Case No. IPR2014-00513, *Oxford Nanopore Technologies, Ltd. v. University of Washington and UAB Research Foundation*, Jun. 19, 2015, 237 pages.
Butler et al., "Determination of RNA Orientation During Translocation Through a Biological Nanopore", Biophysical Journal, vol. 90, No. 1, Jan. 2006, pp. 190-199.
Butler, "Nanopore Analysis of Nucleic Acids", A Dissertation Submitted in Partial Fulfillment of the Requirements for the Degree of Doctor of Philosophy, University of Washington, 2007, 120 pages.
Butler, "Nanopore Analysis of Nucleic Acids—Dissertation Defense Presentation", University of Washington, May 29, 2007.
Butler et al., "Single-Molecule DNA Detection with an Engineered MspA Protein Nanopore", Proceedings of the National Academy of Sciences vol. 105, No. 52, Dec. 30, 2008, pp. 20647-20652.
CA2,945,788, "Notice of Allowance", Mar. 23, 2023, 1 page.
CA2,945,788, "Office Action", Mar. 3, 2022, 5 pages.
CA2,945,788, "Office Action", Feb. 22, 2021, 7 pages.
Chen, "Probing Single DNA Molecule Transport Using Fabricated Nanopores", Nano Letters, vol. 4, No. 11, Nov. 2004, pp. 2293-2298.
Clarke et al., "Continuous Base Identification for Single-Molecule Nanopore DNA Sequencing", Nature Nanotechnology, vol. 4, Apr. 2009, pp. 265-270.
CN200980142855.5, "Office Action", Jun. 25, 2013, 10 pages.
CN201580019738.5, "Office Action", Mar. 11, 2020, 10 pages.
CN201580019738.5, "Office Action", Aug. 18, 2021, 3 pages.
CN201580019738.5, "Office Action", Apr. 28, 2021, 4 pages.
CN201580019738.5, "Office Action", Sep. 29, 2020, 5 pages.
Cockroft et al., "A Single-Molecule Nanopore Device Detects DNA Polymerase Activity with Single-Nucleotide Resolution", Journal of the American Chemical Society, vol. 130, No. 3, Jan. 2008, pp. 818-820.
Dani et al., "MspA Porin-Gold Nanoparticle Assemblies: Enhanced Binding Through a Controlled Cysteine Mutation", Nano Letters, vol. 8, No. 4, Apr. 2008, pp. 1229-1236.
Deamer et al., "Characterization of Nucleic Acids by Nanopore Analysis", Accounts of Chemical Research, vol. 35, No. 10, Oct. 2002, pp. 817-825.
Deamer et al., "Nanopores and Nucleic Acids: Prospects for Ultrarapid Sequencing", Focus Tibtech, vol. 18, No. 4, Apr. 2000, pp. 147-151.
Derrington et al., "Nanopore DNA Sequencing With MspA", PNAS, vol. 107, No. 37, Sep. 2010, pp. 16060-16065.
Dorner et al., "Identification of a Cation-Specific Channel (TipA) in the Cell Wall of the Gram-Positive Mycolata Tsukamurella inchonensis: The Gene of the Channel-Forming Protein Is Identical to mspA of *Mycobacterium smegmatis* and mppA of *Mycobacterium phlei*", Biochimica et Biophysica Acta, vol. 1667, No. 1, Nov. 2004, pp. 47-55.
Engelhardt et al., "A Tetrameric Porin Limits the Cell Wall Permeability of *Mycobacterium smegmatis*", Journal of Biological Chemistry, vol. 277, No. 40, Oct. 2002, pp. 37567-37572.
EP09815404.0, "Communication Pursuant to Rule 114(2) EPC", Exhibit cited in U.S. Patent Trial and Appeal Board Case No. IPR2015-00057, Nov. 27, 2012, 20 pages.
EP09815404.0, "Entry into the European Phase Before the European Patent Office", exhibit cited in U.S. Patent Trial and Appeal Board Case No. IPR2014-00512 and Case No. IPR2014-00513, Jan. 28, 2011, 3 pages.
EP09815404.0, "Letter Accompanying Subsequently Filed Items", Exhibit cited in U.S. Patent Trial and Appeal Board Case D No. IPR2014-00512 and Case No. IPR2014-00513,, Feb. 14, 2013, 15 pages.
EP09815404.0, "Office Action", Jun. 20, 2014, 6 pages.
EP09815404.0, "Supplementary European Search Report", Jul. 20, 2012, 6 pages.
EP09815404.0, "Third Party Observation", Dec. 3, 2012, 21 pages.
EP15779198.9, "Extended European Search Report", Sep. 26, 2017, 9 pages.

(56) References Cited

OTHER PUBLICATIONS

EP15779198.9, "Notice of Decision to Grant", Aug. 5, 2021, 2 pages.
EP15779198.9, "Office Action", Oct. 25, 2019, 4 pages.
EP15779198.9, "Office Action", Oct. 27, 2020, 4 pages.
EP15779198.9, "Office Action", Oct. 25, 2018, 5 pages.
EP21189783.0, "Extended European Search Report", Jan. 26, 2022, 7 pages.
Faller et al., "The Structure of a Mycobacterial Outer-Membrane Channel", Science, vol. 303, No. 5661, Feb. 2004, pp. 1189-1192.
Folgering et al., "Engineering Covalent Oligomers of the Mechanosensitive Channel of Large Conductance From *Escherichia coli* With Native Conductance and Gating Characteristics", Protein Science, vol. 14, No. 12, Dec. 2005, pp. 2947-2954.
Griffiths et al., "The Realm of the Nanopore", Analytical Chemistry, vol. 80, No. 1, Jan. 2008, pp. 23-27.
Gundlach, "Case No. IPR2014-00513", exhibit submitted Jun. 29, 2015, in support of Patent Owners' Supplemental Response for U.S. Patent Trial and Appeal Board, Feb. 19, 2012, 1 page.
Gundlach, "Engineering MspA for Nanopore Sequencing", Grant Application Abstract, Project Period, Sep. 26, 2006, 1 page.
Gundlach, "Engineering MspA for Nanopore Sequencing", National Human Genome Research Institute Grant Supplement No. 5R21 HG004145-02, exhibit cited in U.S. Patent Trial and Appeal Board and Case No. IPR2014-00512 and Case No. IPR2014-00513, Aug. 20, 2007, 13 pages.
Gundlach, "Engineering MspA for Nanopore Sequencing", National Human Genome Research Institute Grant No. 1R21 HG004145-01, exhibit cited in U.S. PatentTrial and Appeal Board Case No. D PR2014-00512 and Case No. IPR2014-00513, Sep. 25, 2006, 38 pages.
Gundlach et al., "MSP Nanopores and Related Methods", U.S. Pat. No. 8,673,550, Patent Owners' Preliminary Response, *Oxford Nanopore Technologies, Ltd. v. The University of Washington and the UAB Research Foundation*, Before the U.S. Patent Trial and Appeal Board, Case No. IPR2014-00513, Jun. 27, 2014, 20 pages.
Gundlach et al., "MSP Nanopores and Related Methods", U.S. Pat. No. 8,673,550, Patent Owners, Preliminary Response, *Oxford Nanopore Technologies, Ltd. v. The University of Washington and the UAB Research Foundation*, Before the U.S. Patent Trial and Appeal Board, Case No. IPR2014-00512, served, Jun. 27, 2014, 35 pages.
Gundlach et al., "MSP Nanopores and Related Methods", U.S. Pat. No. 8,673,550, Petition for Inter Partes Review of U.S. Pat. No. 8,673,550 Under 35 U.S.C. §§ 311-319 and 37 C.F.R. §§ 42.100 et seq. to the U.S. Patent Trial and Appeal Board, Case No. IPR2015-00057, Oct. 13, 2014, 64 pages.
Gundlach, "MSP Nanopores and Related Methods", U.S. Pat. No. 8,673,55, Petition for Inter Partes Review of U.S. Pat. No. 8,673,550 Under 35 U.S.C. §§ 311-319 and 37 C.F.R. §§ 42.100 et seq. to the U.S. Patent Trial and Appeal Board, Case No. IPR2014-00512, Mar. 18, 2014, 67 pages.
Gundlach et al., "MSP Nanopores and Related Methods", U.S. Pat. No. 8,673,550, Petition for Inter Partes Review of U.S. Pat. No. 8,673,550 Under 35 U.S.C. §§ 311-319 and 37 C.F.R. §§ 42.100 D t seq. to the U.S. Patent Trial and Appeal Board, Case No. IPR2014-00513, Mar. 18, 2014, 69 pages.
Gundlach et al., "Single Molecule DNA Detection with an Engineered MspA Protein Nanopore", Jul. 30, 2008.
Gundlach, "Single-Molecule DNA Detection with an Engineered MspA Protein Nanopore", cover letter to PNAS and supplemental information; and letter from Dr. Daniel Branton to PNAS exhibit submitted Jun. 29, 2015, in support of Patent Owners' Supplemental Response for U.S. Patent Trial and Appeal Board, Case No. IPR2014-00513, Jul. 31, 2008, 31 pages.
Gyarfas et al., "Mapping the Position of DNA Polymerase-Bound DNA Templates in a Nanopore at 5 A Resolution", ACS Nano, vol. 3, No. 6, Jun. 2009, pp. 1457-1466.

Hanss et al., "Identification and Characterization of a Cell Membrane Nucleic Acid Channel", Proceedings of the National Academy of Sciences of the United States of America, vol. 95, No. 4, Feb. 1998, pp. 1921-1926.
Heger, "Pre-Print Study Demonstrates Nanopore Sequencing of Bacteriophage Genome With MspA Pore", Available Online at: www.genomeweb.com, *Oxford Nanopore Technologies, Ltd. v. University of Washington and UAB Research Foundation*, Jun. 24, 2014, pp. 1-4.
Heger, "Proof-of-Principle Study Shows MspA Is Superior to Alpha-Hemolysin for Protein Nanopore Sequencing", Available Online at: www.genomeweb.com,, Aug. 24, 2010, pp. 1-4.
Heins et al., "The Preprotein Conducting Channel at the Inner Envelope Membrane of Plastids", EMBO Journal, vol. 21, No. 11, Jun. 2002, pp. 2616-2625.
Heinz et al., "Mycobacterial Porins—New Channel Proteins in Unique Membranes", Conference of the German Society of Biochemistry, Available Online at: http://www.vetmed.uni-giessen.de:80/pharmtoxlveranstaltungen/rauisch_05/abstracts pdf, Dec. 17, 2005, 1 page.
Heinz et al., "Selective Extraction and Purification of a Mycobacterial Outer Membrane Protein", Analytical Biochemistry, vol. 285, No. 1, Oct. 2000, pp. 113-120.
Heinz et al., "The Core of the Tetrameric Mycobacterial Porin MspA Is an Extremely Stable Sheet beta Domain", Journal of Biological Chemistry, vol. 278, No. 10, Mar. 2003, pp. 8678-8685.
Hoffman et al., "Disclosure of the Mycobacterial Outer Membrane: Cryo-Electron Tomography and Vitreous Sections Reveal the Lipid Bilayer Structure", PNAS, vol. 105, No. 10, Mar. 11, 2008, pp. 3963-3967.
Hoffmann, "Construction and Functional Analysis of Constriction Zone Mutants of *Mycobacterium smegmatis* Porin A (MspA)", Thesis, University of Erlangen-Nuremberg, Oct. 2005, 115 pages.
Hornblower et al., "Single-Molecule Analysis of DNA-Protein Complexes Using Nanopores", Nature Methods, vol. 4, No. 4, Apr. 2007, pp. 315-317.
Howorka et al., "Probing Distance and Electrical Potential Within a Protein Pore With Tethered DNA", Biophysical Journal, vol. 83, No. 6, Dec. 2002, pp. 3202-3210.
Howorka et al., "Sequence-Specific Detection of Individual DNA Strands Using Engineered Nanopores", Nature Biotechnology, vol. 19, No. 7, 2001, pp. 636-639.
Huff et al., "Functions of the Periplasmic Loop of the Perin MspA From *Mycobacterium smegmatis*", Journal of Biological Chemistry, vol. 284, No. 15, Apr. 2009, pp. 10223-10231.
Jain et al., "Improved Data Analysis for the MiniON Nanopore Sequencer", Nature Methods, vol. 12, No. 4, Apr. 2015, pp. 351-356.
Jayasinghe et al., "The Leukocidin Pore: Evidence for an OctamerWith Four LukF Subunits and Four LukS Subunits Alternating Around a Central Axis", Protein Science, vol. 14, No. 10, Oct. 2005, pp. 2550-2561.
Jetha et al., "Forming an α-Hemolysin Nanopore for Single-Molecule Analysis", Micro and Nano Technologies in Bioanalysis, Methods in Molecular Biology, vol. 544, 2009, pp. 113-127.
Kalita et al., "Enhancing the Water Solubility of Nanoparticles (CdSe, Au, Au/Fe) by Ligand Exchange and Subsequent Binding to a Cysteine Mutant of the Mycobacterial Perin MspA", Abstract 217, presented Friday, the 41st Midwest Regional Meeting, Available Online at: http://acs.confex.com/acs/mwrm06/techprogram/MEETING.HTM, Oct. 27, 2006, 1 page.
Karow, "AGBT: Oxford Nanopore to Begin Selling Two Low-Cost DNA Strand Sequencing Instruments This Year", Available Online at: www.genomeweb.com, Feb. 21, 2012, pp. 1-4.
Kasianowicz et al., "Characterization of Individual Polynucleotide Molecules Using a Membrane Channel", Proceedings of the National Academy of Sciences, vol. 93, No. 24, Nov. 1996, pp. 13770-13773.
Laszlo et al., "Nanopore Sequencing of the Phi X 174 Genome", University of Washington, Cited in U.S.D.C., Southern District of California, Case No. 3:16-cv-00477-LAB-MDD, as exhibit 16, and cited in ITC, Investigation No. 337-3123, as exhibit 32, Jun. 17, 2014, 39 pages.

(56) References Cited

OTHER PUBLICATIONS

Litchtinger et al., "Evidence for a Small Anion-Selective Channel in the Cell Wall of *Mycobacterium bovis* BCG Besides a Wide Cation-Selective Pore", FEBS Letters, vol. 454, No. 3, Jul. 1999, pp. 349-355.
Lu et al., "Thermal Motion of DNA in an MspA Pore", Harvard University, cited in U.S.D.C., Southern District of California, Case No. 3:16-cv-00477-LAB-MDD, as exhibit 29, and cited in ITC, Investigation No. 337-3123, as exhibit 96, Jun. 2015, pp. 1-16.
Maglia et al., "Enhanced Translocation of Single DNA Molecules Through α-Hemolysin Nanopores by Manipulation of Internal Charge", Proceedings of the National Academy of Science USA, vol. 105, No. 50, Dec. 16, 2008, pp. 19720-19725.
Mahfoud et al., "Topology of the Perin MspA in the Outer Membrane of *Mycobacterium smegmatis*", Journal of Biological Chemistry, vol. 281, No. 9, Mar. 2006, pp. 5908-5915.
Manrao et al., "Nucleotide Discrimination with DNA Immobilized in the MspA Nanopore", PloS one, vol. 6, No. 10, Oct. 4, 2011, pp. 1-7.
Meller et al., "Rapid Nanopore Discrimination Between Single Polynucleotide Molecules", PNAS, vol. 97, No. 3, Feb. 2000, pp. 1079-1084.
Meller et al., "Single Molecule Measurements of DNA Transport Through a Nanopore", Electrophoresis, vol. 23, No. 16, Aug. 2002, pp. 2583-2591.
Meller et al., "Voltage-Driven DNA Translocations Through a Nanopore", Physical Review Letters, vol. 86, No. 15, Apr. 2001, pp. 3435-3438.
Minier et al., "Techniques: Use of Concatenated Subunits for the Study of Ligand-Gated Ion Channels", Trends in Pharmacological Sciences, vol. 25, No. 9, Sep. 2004, pp. 499-503.
Movileanu, "Interrogating Single Proteins Through Nanopores: Challenges and Opportunities", Trends in Biotechnology, vol. 27, No. 6, Jun. 2009, pp. 333-341.
Myers, "PNAS Editorial Staff Member", Patent Owners' Supplemental Response for U.S. Patent Trial and Appeal Board, Case No. IPR2014-00513, Jun. 29, 2015, 6 pages.
Nakane et al., "Nanopore Sensors for Nucleic Acid Analysis", Journal of Physics: Condensed Matter, vol. 15, No. 32, Aug. 2003, pp. R1365-R1393.
Niederweis, "Cloning of the mspA Gene Encoding a Porin From *Mycobacterium smegmatis*", Molecular Microbiology, vol. 33, No. 5, Sep. 1999, pp. 933-945.
Niederweis, "Mycobacterial Porins—New Channel Proteins in Unique Outer Membranes", Molecular Microbiology, vol. 49, No. 5, Sep. 2003, pp. 1167-1177.
Pavlenok et al., "MspA Nanopores from Subunit Dimers", Plos One, vol. 7, No. 6, Jun. 18, 2012, pp. 1-12.
PCT/US2009/057915, "International Patent Application No.", Exhibit cited in U.S. Patent Trial and Appeal Board Case No. IPR2015-00057, Sep. 22, 2009, 143 pages.
PCT/US2009/057915, "International Search Report and Written Opinion", Aug. 18, 2010, 13 pages.
PCT/US2015/026239, "International Preliminary Report on Patentability", Nov. 17, 2016, 8 pages.
PCT/US2015/026239, "International Search Report and Written Opinion", Nov. 3, 2016, 10 pages.
Pennisi, "Genome Sequencing: Search for Pore-Fection", Science, vol. 336, No. 6081, May 4, 2012, pp. 534-537.
Rhee et al., "Nanopore Sequencing Technology: Nanopore Preparations", Trends in Biotechnology, vol. 25, No. 4, Apr. 2007, pp. 174-181.
Rhee et al., "Nanopore Sequencing Technology: Research Trends and Applications", Trends in Biotechnology, vol. 24, No. 12, Dec. 2006, pp. 580-586.
Rieβ et al., "Study of the Properties of a Channel-Forming Protein of the Cell Wall of the Gram-Positive Bacterium *Mycobacterium phlei*", Journal of Membrane Biology, vol. 182, No. 2, Jul. 2001, pp. 147-157.
Stahl et al., "MspA Provides the Main Hydrophilic Pathway Through the Cell Wall of *Mycobacterium smegmatis*", Molecular Microbiology, vol. 40, No. 2, Apr. 2001, pp. 451-464.
Stefureac, "Transport of α-Helical Peptides through α-Hemolysin and Aerolysin Pores", Biochemistry, vol. 45, No. 30, 2006, pp. 9172-9179.
Stephan et al., "The Growth Rate of *Mycobacterium smegmatis* Depends on Sufficient Porin-Mediated Influx of Nutrients", Molecular Microbiology, vol. 58, No. 3, Nov. 2005, pp. 714-730.
Stoddart et al., "Single-Nucleotide Discrimination in Immobilized DNA Oligonucleotides With a Biological Nanopore", Proceedings of the National Academy of Sciences USA, vol. 106, No. 19, May 12, 2009, pp. 7702-7707.
Szabo et al., "DNA Translocation Across Planar Bilayers Containing Bacillus Subtilis Ion Channels", Journal of Biological Chemistry, vol. 272, No. 40, 1997, pp. 25275-25282.
Szabo et al., "Double-Stranded DNA Can Be Translocated Across a Planar Membrane Containing Purified Mitochondrial Perin", FASEB, vol. 12, Apr. 1, 1998, pp. 495-502.
Tamm et al., "Folding and Assembly of β-Barrel Membrane Proteins", Biochimica et Biophysica Acta, vol. 1666, Nos. 1-2, Nov. 3, 2004, pp. 250-263.
Timp et al., "Think Small: Nanopores for Sensing and Synthesis", IEEE Access, vol. 2, Nov. 20, 2014, pp. 1396-1408.
Trias et al., "Characterization of the Channel Formed by the Mycobacterial Porin in Lipid Bilayer Membranes", Journal of Biological Chemistry, vol. 268, No. 9, Mar. 1993, pp. 6234-6240.
Trias et al., "Permeability of the Cell Wall of *Mycobacterium smegmatis*", Molecular Microbiology, vol. 14, No. 2, Oct. 1994, pp. 283-290.
Trias et al., "Porins in the Cell Wall of Mycobacteria", Science, vol. 258, No. 5087, Nov. 27, 1992, pp. 1479-1481.
Venkatesan et al., "Nanopore Sensors for Nucleic Acid Analysis", Nature Nanotechnology, vol. 6, No. 10, Oct. 2011, pp. 615-624.
Vercouture et al., "Discrimination Among Individual Watson-Crick Base Pairs at the Termini of Single DNA Hairpin Molecules", Nucleic Acids Research, vol. 31, No. 4, Feb. 2003, pp. 1311-1318.
Vercouture et al., "Rapid Discrimination Among Individual DNA Hairpin Molecules at Single-Nucleotide Resolution Using an Ion Channel", Nature Biotechnology, vol. 19, No. 3, Mar. 2001, pp. 248-252.
Wang et al., "DNA Heterogeneity and Phosphorylation Unveiled by Single-Molecule Electrophoresis", Proceedings of the National Academy of Science, (PNAS), vol. 101, No. 37, Sep. 14, 2004, pp. 13472-13477.
Wang et al., "Nanopores With a Spark for Single-Molecule Detection", Nature Biotechnology, vol. 19, No. 7, Jul. 2001, pp. 622-623.
Wong, "Engineering *Mycobacterium smegmatis* Porin A (MspA) for DNA Analysis", University of Washington Summer Research Poster Session, Pamphlet Cover, Program Description, Schedule of Events, Abstract and Poster, Aug. 16, 2007, 5 pages.
Worner et al., "Characterization of Nanostructured Surfaces Generated by Reconstitution of the Perin MspA From *Mycobacterium smegmatis*", Small, vol. 3, No. 6, Jun. 2007, pp. 1084-1097.
Zhou et al., "Human α4β2 Acetylcholine Receptors Formed from Linked Subunits", Journal of Neuroscience, vol. 23, No. 27, Oct. 8, 2003, pp. 9004-9015.

FIG. 1

MSP NANOPORES AND USES THEREOF

CROSS REFERENCE TO RELATED APPLICATIONS

This application is a continuation of U.S. application Ser. No. 17/674,140 filed Feb. 17, 2022, which is a continuation of U.S. application Ser. No. 16/997,032 filed Aug. 19, 2020, now issued U.S. Pat. No. 11,292,817, which is a divisional of U.S. application Ser. No. 15/304,183 filed Oct. 14, 2016, now issued U.S. Pat. No. 10,781,237, which is a U.S. national stage application under 35 USC § 371 of PCT/US2015/026239 filed Apr. 16, 2015, which claims the benefit of U.S. Provisional Application No. 61/980,415 filed Apr. 16, 2014 and U.S. Provisional Application No. 61/980,393 filed Apr. 16, 2014, which are hereby incorporated herein in their entireties by this reference.

STATEMENT OF GOVERNMENT RIGHTS

This invention was made with government support under Grant No. R01HG005115 awarded by the National Institutes of Health. The government has certain rights in the invention.

SEQUENCE LISTING

The instant application contains a Sequence Listing in XML format. The Sequence Listing, named UAB-160US4-035979-1410399-ST26.xml, which was created on Sep. 28, 2023, is 16 Kilobytes in size, and is hereby incorporated by reference in its entirety.

BACKGROUND

Identification and characterization of analytes often involve expensive and time-consuming methodology. For example, current technologies require expensive custom-made reagents and/or detection methods to determine nucleic acid sequences. Similarly, methods for determining protein sequences, for example, peptide fingerprinting by mass spectrometry technologies, can be laborious and costly. Therefore, efficient methods of detecting and analyzing nucleic acids, proteins and other analytes are necessary.

SUMMARY

Provided herein are nucleic acid sequences encoding a mutant single-chain *Mycobacterium smegmatis* porin (Msp). The nucleic acid sequence optionally comprises a first and second nucleotide sequence, wherein the first nucleotide sequence encodes a first Msp monomer sequence and the second nucleotide sequence encodes a second Msp monomer sequence; and a third nucleotide sequence encoding an amino acid linker sequence. In some of the mutant single-chain Msps provided herein, at least one of the first and second Msp monomer sequences is a mutant Msp monomer sequence that comprises a mutation at position 97. In other mutant single-chain Msps provided herein, at least one of the first and second Msp monomer sequences is a mutant Msp monomer sequence comprising one or more mutations at any of the following amino acid positions: I68, S73, S116, P123 or V128.

Optionally, the nucleic acid sequence encoding the mutant single-chain Msp comprises a first, second, third, fourth, fifth, sixth, seventh, and eighth nucleotide sequence or any subset thereof, and the first, second, third, fourth, fifth, sixth, seventh, and eighth nucleotide sequences encode a first, second, third, fourth, fifth, sixth, seventh, and eighth Msp monomer sequence, respectively. The nucleic acid sequence further comprises a ninth nucleotide sequence encoding an amino acid linker sequence which is optionally present at multiple sites (e.g., between the Msp monomer sequences). The first Msp monomer sequence can be a mutant Msp monomer sequence that comprises one or more mutations at any of the following amino acid positions: I68, S73, S116, P123 or V128 or a mutant Msp monomer sequence that comprises a mutation at position 97.

Further provided herein is a nucleic acid encoding a mutant Msp monomer. The Msp monomer comprises a mutation at one or more of the following positions: I68, S73, P97, S116, P123 or V128.

Further provided are polypeptides comprising the mutant Msps described herein and polypeptides encoded by the nucleic acids described herein. Also provided herein is a system comprising a mutant Msp described herein, wherein the Msp has a vestibule and a constriction zone that define a tunnel, wherein the tunnel is positioned between a first conductive liquid medium and a second conductive liquid medium, wherein at least one conductive liquid medium comprises an analyte, and wherein the system is operative to detect the analyte, when the system is subjected to an electric field sufficient to translocate the analyte from one conductive liquid medium to the other.

Further provided are methods for detecting the presence of an analyte. The methods include applying an electric field sufficient to translocate an analyte from a first conductive medium to a second conductive medium in liquid communication through a mutant Msp described herein and measuring an ion current, wherein a reduction in the ion current indicates the presence of the analyte in the first medium.

DESCRIPTION OF THE DRAWINGS

FIG. 1 shows an alignment of the MspA, MspB, MspC and MspD monomers of *Mycobacterium smegmatis*. The numbering of each protein starts with the first amino acid of the mature portion of the sequence. The MspA, MspB, MspC and MspD monomer sequences without a signal/leader sequence are provided as SEQ ID NO: 1, SEQ ID NO: 2, SEQ ID NO: 3 and SEQ ID NO: 4, respectively.

Figure 4:
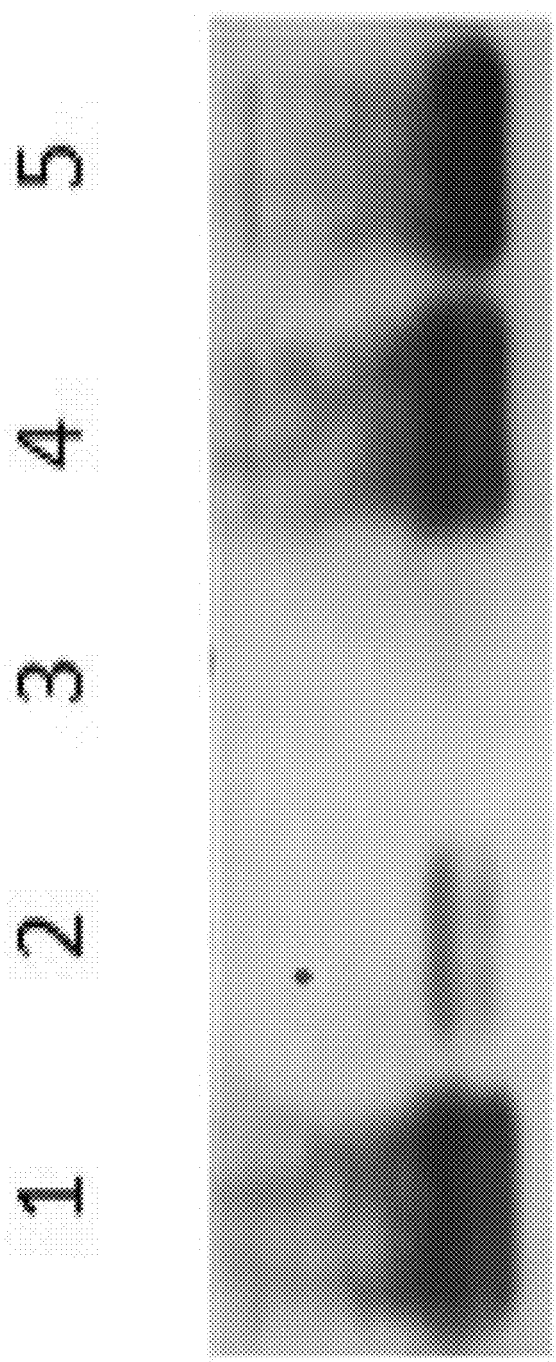

FIG. 4 is a Western blot of Msp porin expression in *M. smegmatis* porin gene deletion mutants. Msp porins were extracted with 0.5% octylpolyethyleneoxide and 10 µl were loaded in each lane. Proteins were separated on 8% SDS-PAGE and detected by Western blot using a polyclonal antibody against MspA. Lanes: 1, SMR5 (wt; expression of mspA); 2, ML16 (triple porin deletion mutant; mspB expression); 3, ML712/pMS2 (quadruple porin deletion mutant; empty vector); 4, ML712/pMN016 (+mspA expression plasmid); 5, ML712/pML904 (+M1 mspA expression plasmid).

Figure 5:
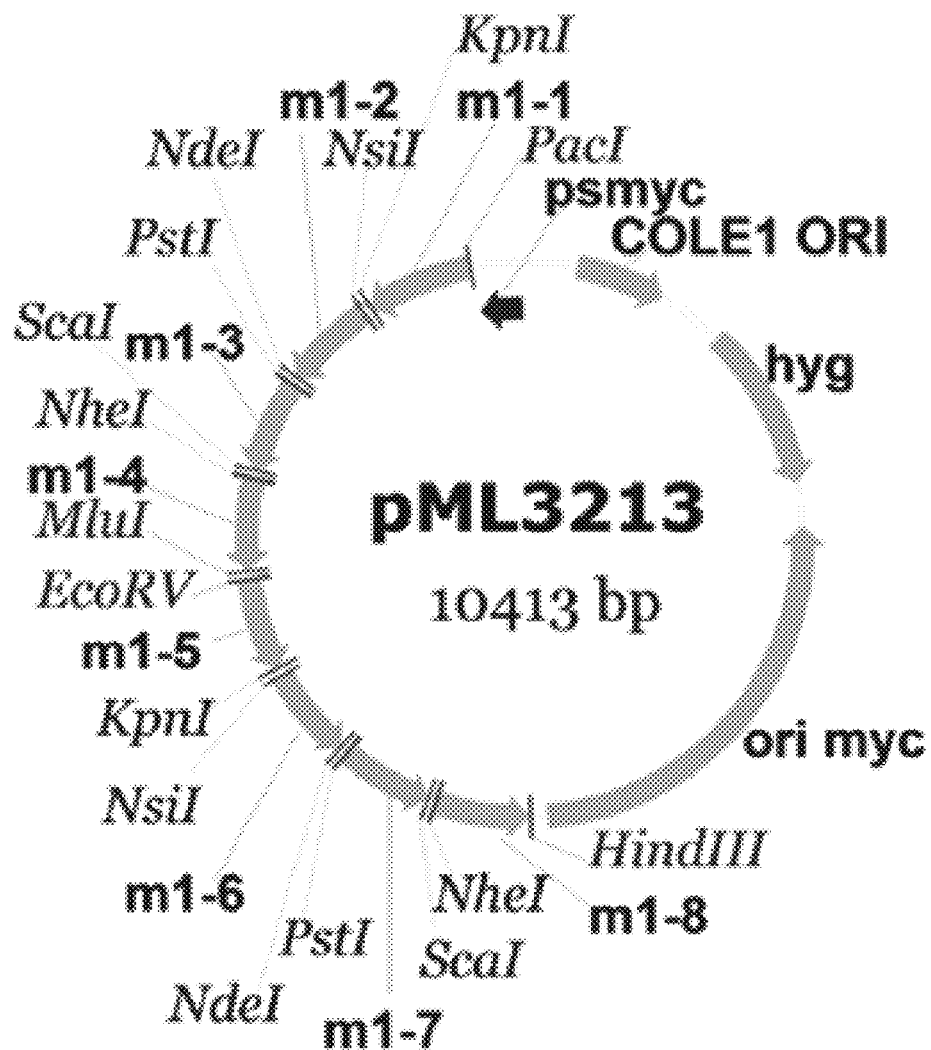

FIG. 5 is a schematic representation of the mycobacterial expression plasmid pML3213 encoding single-chain $M1_8$-MspA. The plasmid comprises the following: hyg, hygromycin resistance gene; ory myc, a mycobacterial origin of replication; COLE1 ORI, an *E. coli* origin of replication; psmyc, constitutive mycobacterial promoter; m1-1, m1-2, etc., m1 mspA genes with an index number corresponding to position in the single-chain gene construct. Tetrad A is flanked by PacI at the beginning of the first m1-mspA and by MluI at the end of the fourth m1-mspA; tetrad B is flanked by EcoRV at the beginning of the fifth m1-mspA and by HindII at the end of the eighth m1-mspA. Individual m1-mspA genes within the tetrads are flanked by KpnI, NsiI, NdeI, PstI, ScaI, NheI. Connecting $(GGGGS)_3$ (SEQ ID NO: 5) linkers are located between restriction sites, but are not shown.

Figure 6:
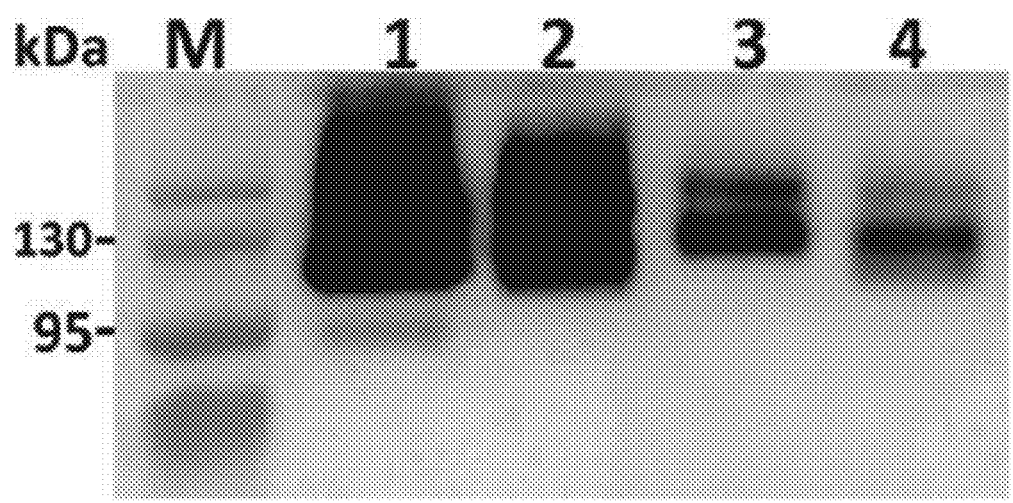

FIG. 6 is a Western blot showing the analysis of single-chain MspA expression in *M. smegmatis* ML714. Msp porins were extracted with 0.5% octylpolyethyleneoxide and 10 µl were loaded in each lane. Proteins were separated in 10% SDS-PAGE followed by transfer onto PVDF membrane, and probed with αMspA monoclonal antibodies. The lanes are marked as follows: M, protein ladder; 1, expression wt MspA (SMR5); 2, $M1_2$-MspA; 3, $M1_4$-MspA; 4, $M1_8$-MspA (single-chain M1-MspA) The amount of MspA was determined by quantitative image analysis.

Figure 7:
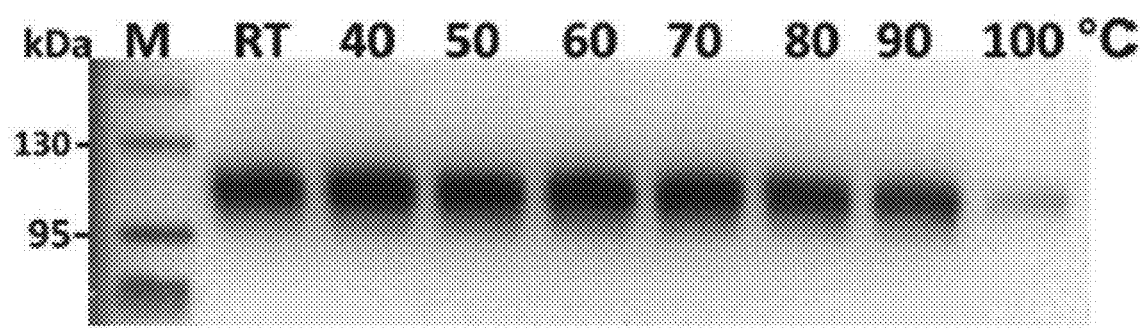

FIG. 7 shows the thermal stability of single-chain $M1_8$-MspA. Single-chain M1 MspA porins were extracted with 0.5% n-octylpolyethyleneoxide. 15 µl of the sample were incubated in a buffer containing 2% SDS for 15 min at temperatures indicated above each lane. Proteins were separated in 8% SDS PAGE followed by transfer onto PVDF membrane and probed with αMspA polyclonal antibodies. The lanes are marked as follows: M, protein ladder; RT, room temperature; 40, 50, etc. indicate incubation temperature. Equal amounts of the protein samples were loaded onto each lane.

Figure 8A:
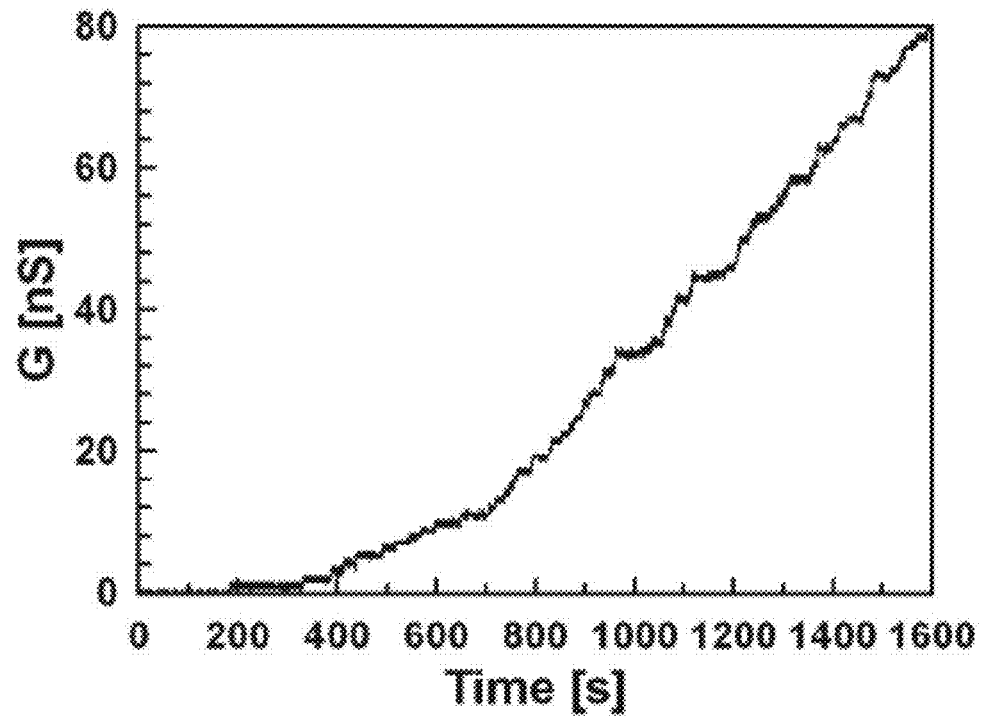

FIG. 8A shows the results of lipid bilayer experiments with $M1_8$-MspA. Approximately 70 ng of protein were added to the bilayer chamber. Current traces of $M_{1-8}$-MspA in a diphytanoylphosphatidylcholine lipid bilayer were recorded in IM KCl at a potential of −10 mV. This resulted in the step-wise increase in the current across the lipid bilayer indicating the insertion of $M1_8$-MspA channels into the membrane.

Figure 8B:
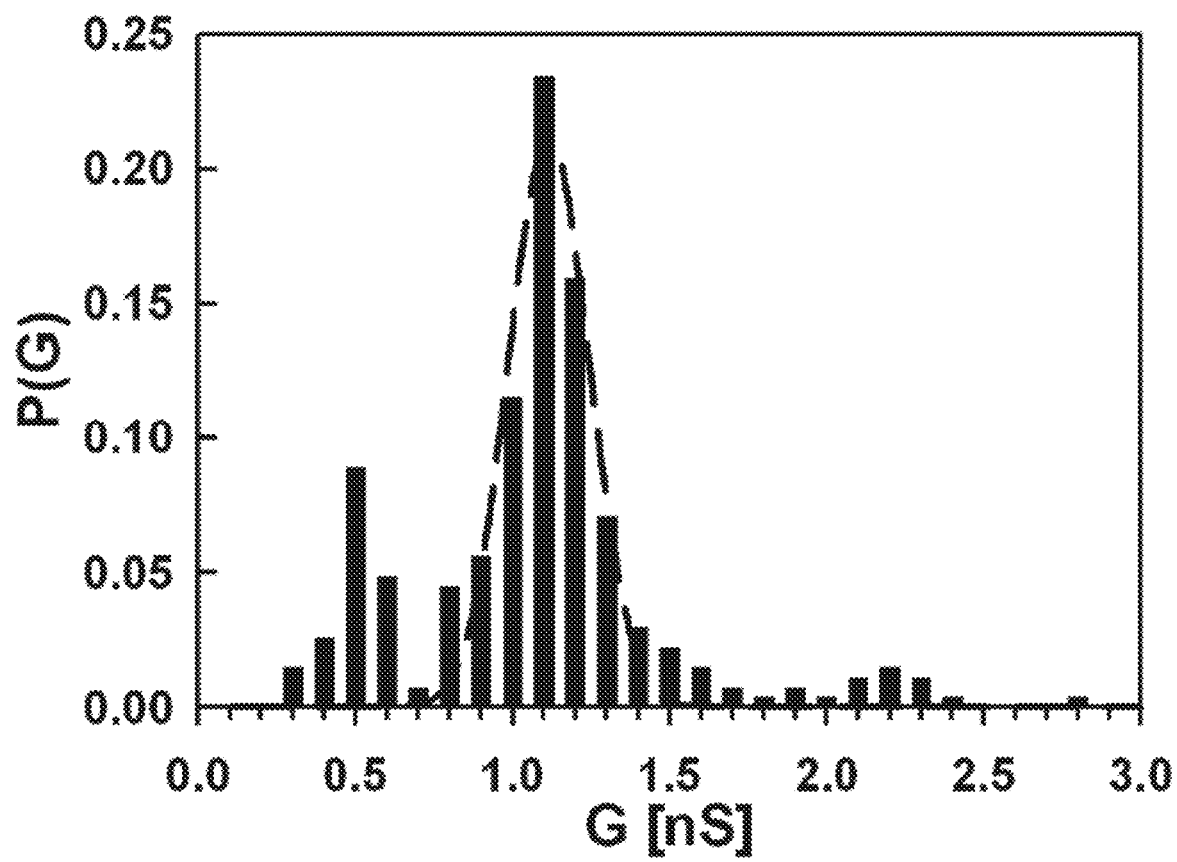

FIG. 8B is a histogram of the conductance of $M1_8$-MspA. 269 pores in four different membranes were analyzed. Single-chain $M_{1-8}$-MspA showed a predominant conductance peak at 1.1 nS.

Figure 9:
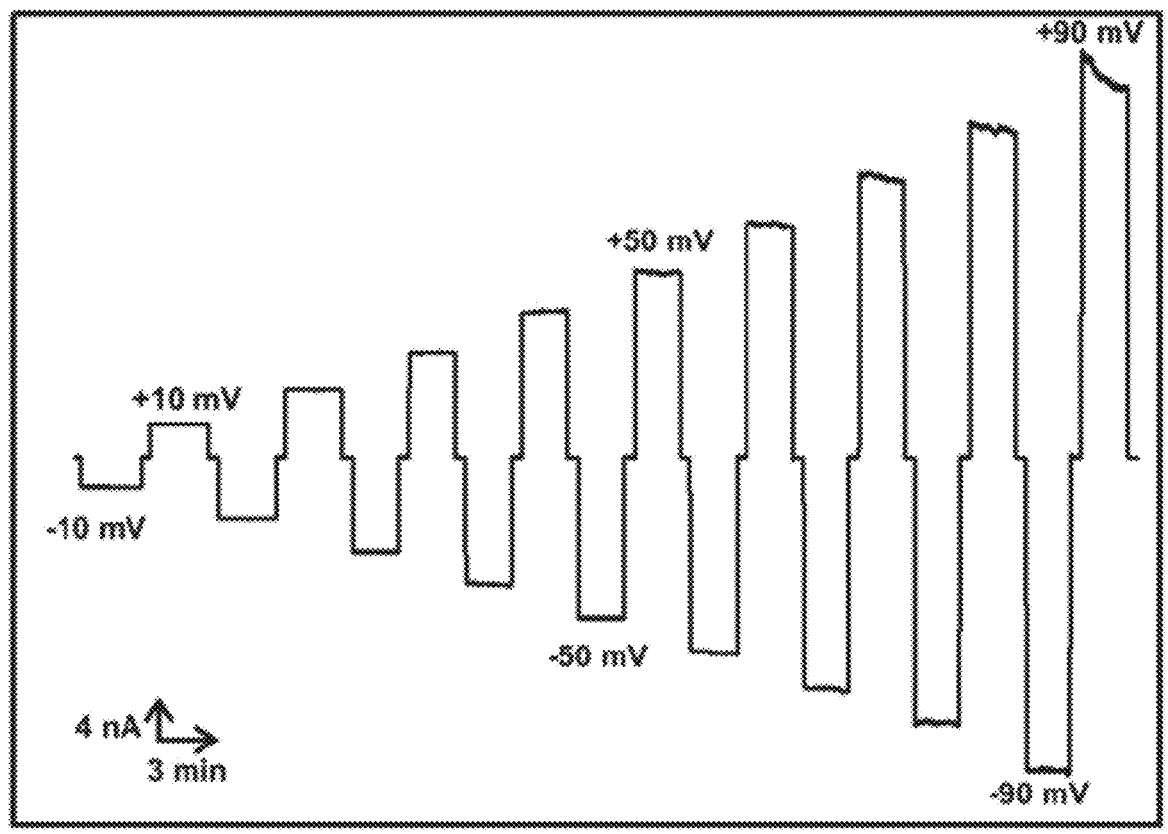

FIG. 9 shows the results of voltage gating experiments. $M1_8$-MspA was added to the cis-side of a diphytanoylphosphatidylcholine membrane. Increasingly positive (upper traces) and negative (lower traces) voltages were applied to the membrane when ~220 channels were reconstituted into the membrane. The membrane current was recorded at each applied voltage. The critical voltage at which the channels began to close (Vc) was determined as the voltage when the conductance of the lipid bilayer decreased after its initial maximal value. The critical voltage Vc of $M1_8$-MspA was +90 mV. The $M1_8$-MspA channel was stable at all applied negative voltages.

Figure 10A:
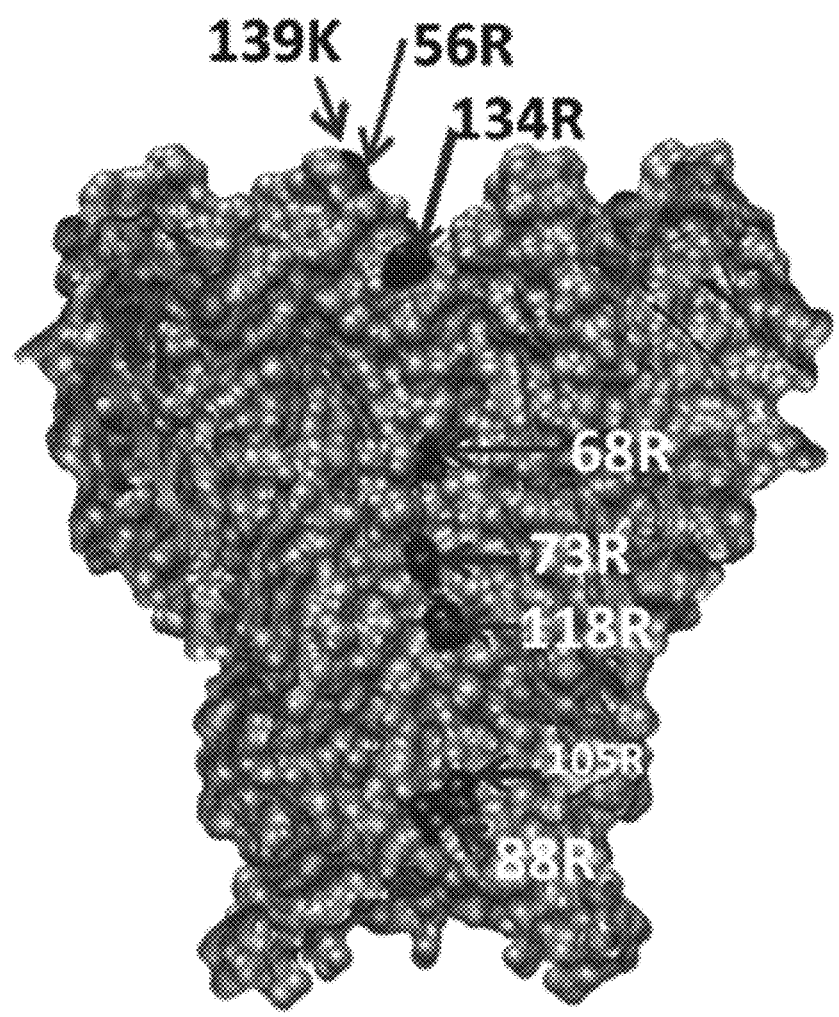

FIG. 10A shows an example of a positive ramp created in a single-chain Msp comprising a first mutant Msp monomer that comprises mutations at positions D56, I68, S73, D118, D134 and E139 and a seventh mutant Msp monomer that comprises a mutation at positions L88 and I105.

Figure 10B:
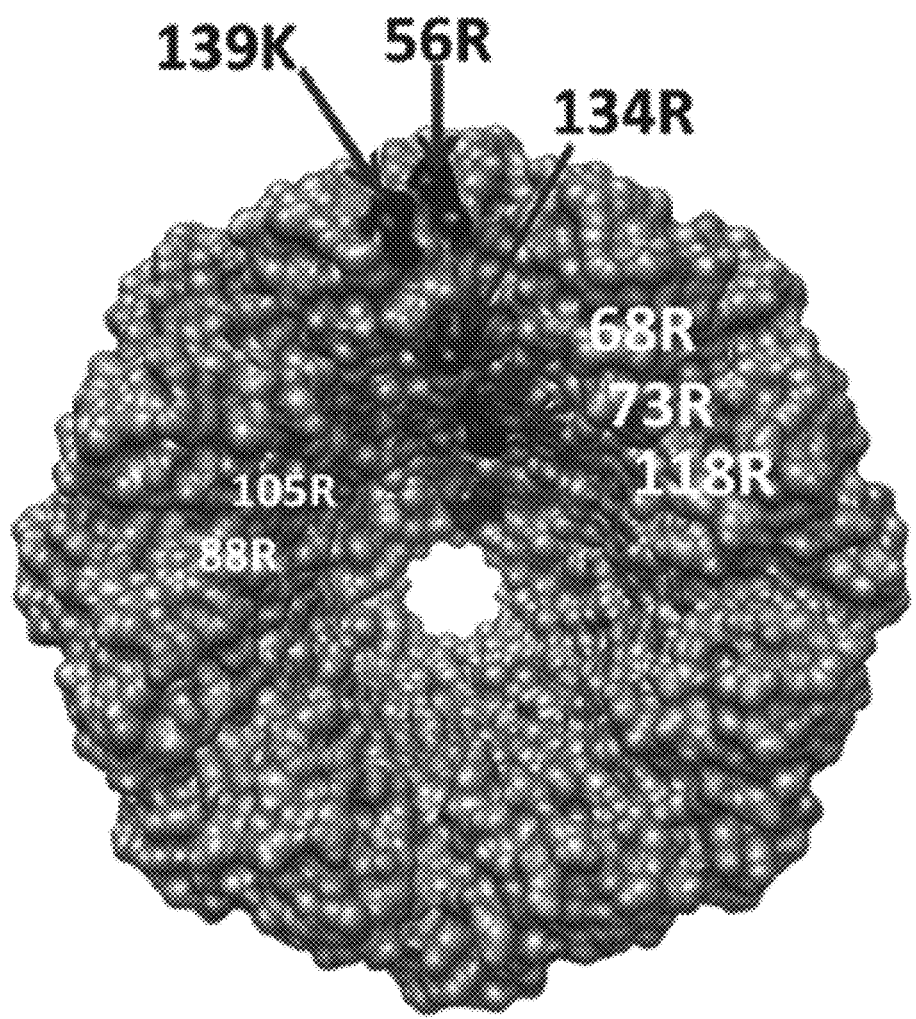

FIG. 10B shows a top view of a positive ramp created in a single-chain Msp comprising a first mutant Msp monomer that comprises mutations at positions D56, I68, S73, D118, D134 and E139 and a seventh mutant Msp monomer that comprises a mutation at positions L88 and I105.

Figure 10C:
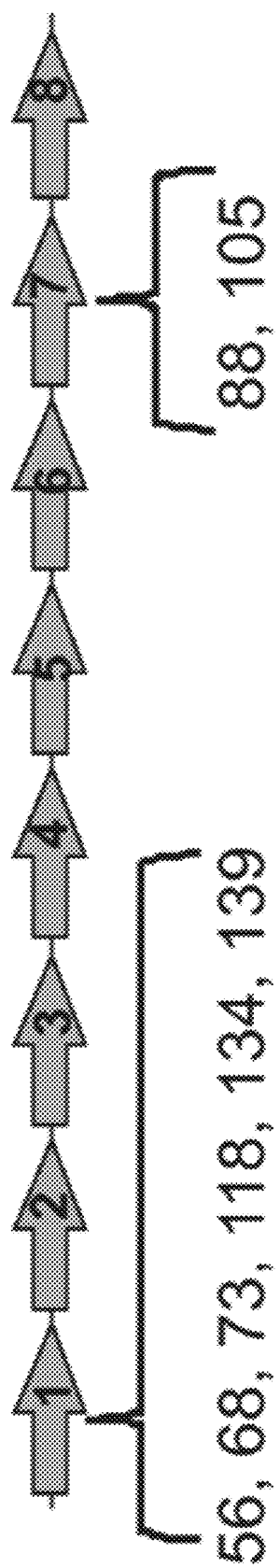

FIG. 10C is a schematic of a single-chain Msp. Numbers under subunits #1 and #7 represent locations of the positive ramp.

Figure 11:
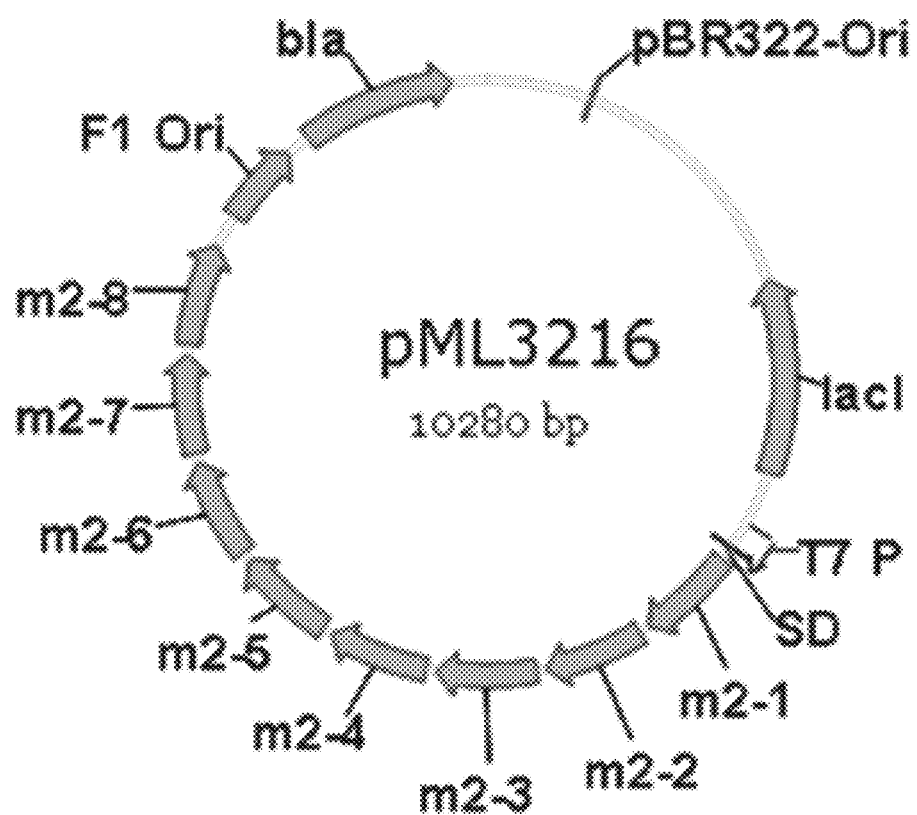

FIG. 11 is a schematic representation of plasmid pML3216, for the expression of single-chain m2-mspA in *E. coli*. bla, ampicillin resistance gene; pBR322-Ori, *E. coli* origin of replication; lacI, lac repressor protein; T7 P, T7 promoter; SD, Shine-Dalgarno sequence; m2-1-m2-8, m2 mspA codon.

Figure 12:
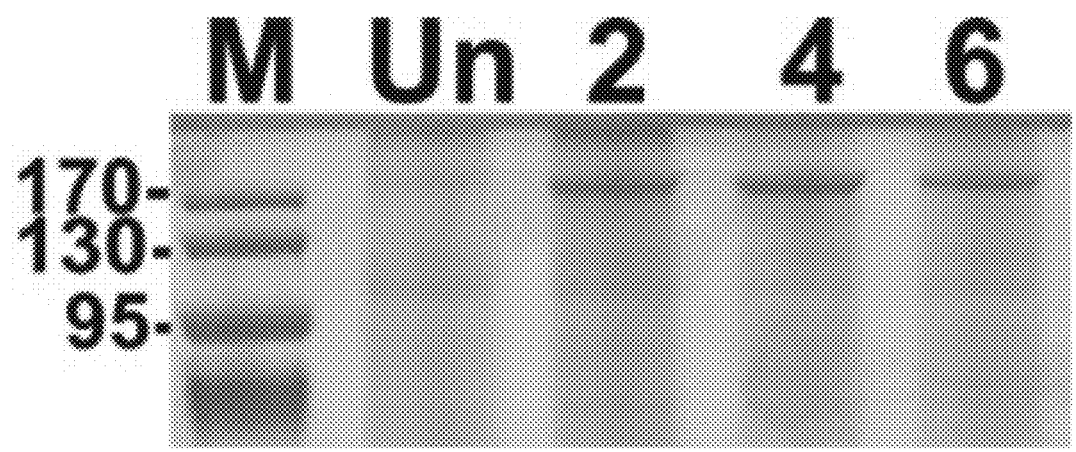

FIG. 12 shows that scm2-mspA can be produced in *E. coli*. *E. coli* Omp8 cells were induced with 1.5 mM IPTG at OD600 of 0.5. At different time points, cells were collected and lysed. Equal amounts of protein sample were loaded onto 10% polyacrylamide gel. After electrophoresis, the gel was stained with Coomassie and scanned for quantification by LabWorks software (Waltham, Massachusetts). Lanes: M, molecular weight marker with masses indicated on the left (kDa); Un, non-induced cells; 2, 4 and 6 hours after induction with IPTG.

Figure 13:
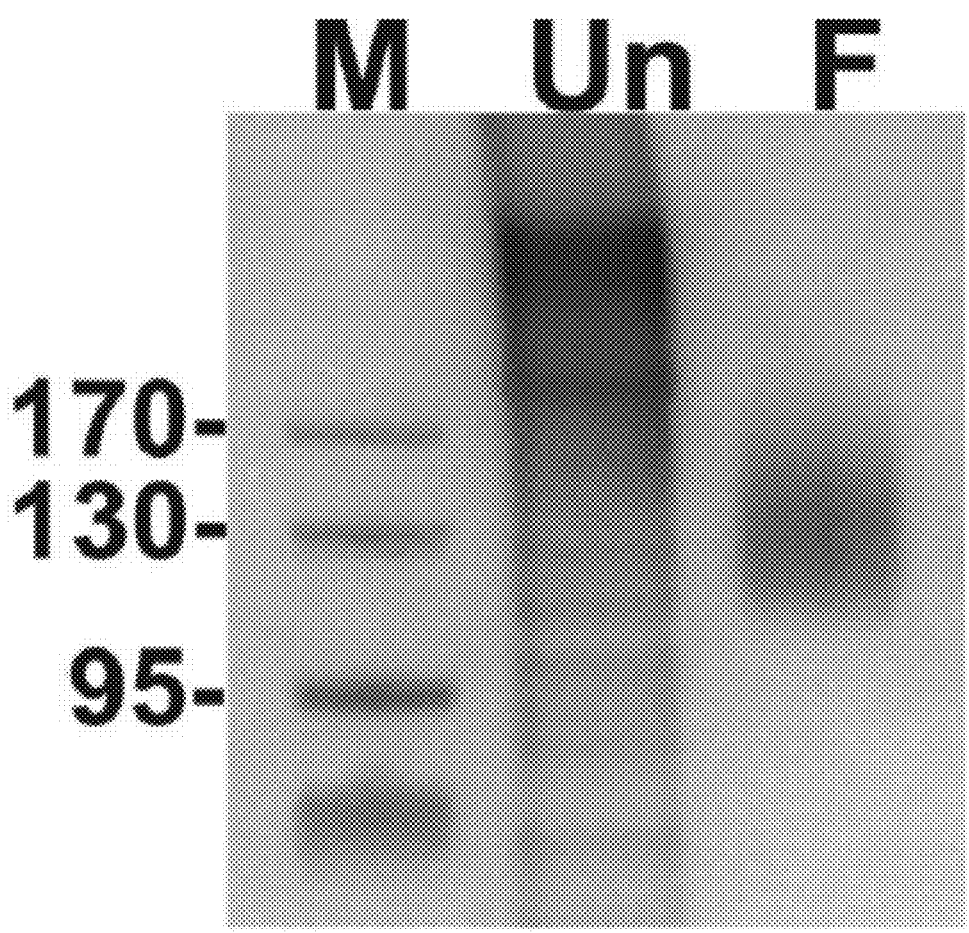

FIG. 13 shows a Western blot of scMspA M2 refolding. Samples before and after refolding were loaded onto 8% polyacrylamide gel followed by overnight transfer onto PVDF membrane. The membrane was stained with MspA-specific rabbit antibodies. Lanes: M, molecular weight marker with masses indicated on the left (kDa); Un, unfolded sample after anion exchange chromatography; F, folded scMspA M2.

Figure 3:
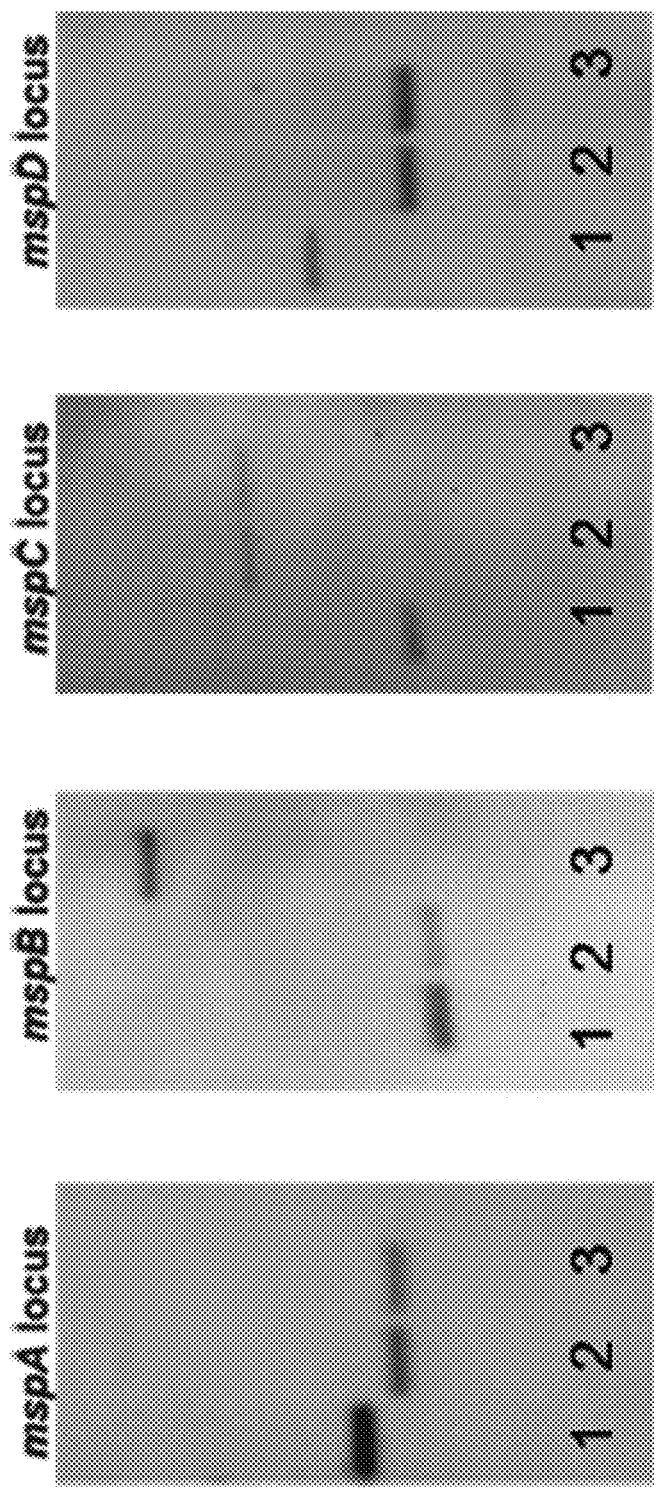
FIG. 3 is a Southern blot of msp loci in *M. smegmatis* strains. Chromosomal DNA was isolated from SMR5 (1), ML16 (2), and ML712 (3) *M. smegmatis* strains. DNA fragments were separated on 1% agarose gel, blotted onto a nitrocellulose membrane, and detected using specific probes labeled with digoxigenin. The sizes of the DNA fragments that hybridized with the probe were consistent with predicted values. Expected fragment sizes: mspA locus: 1-1500 bp, 2,3-1250 bp; mspB locus: 1,2-1140 bp, 3-1850 bp; mspC locus: 1-1200 bp, 2,3-2100 bp; mspD locus: 1-1730 bp, 2,3-1090 bp.
Figure 14A:
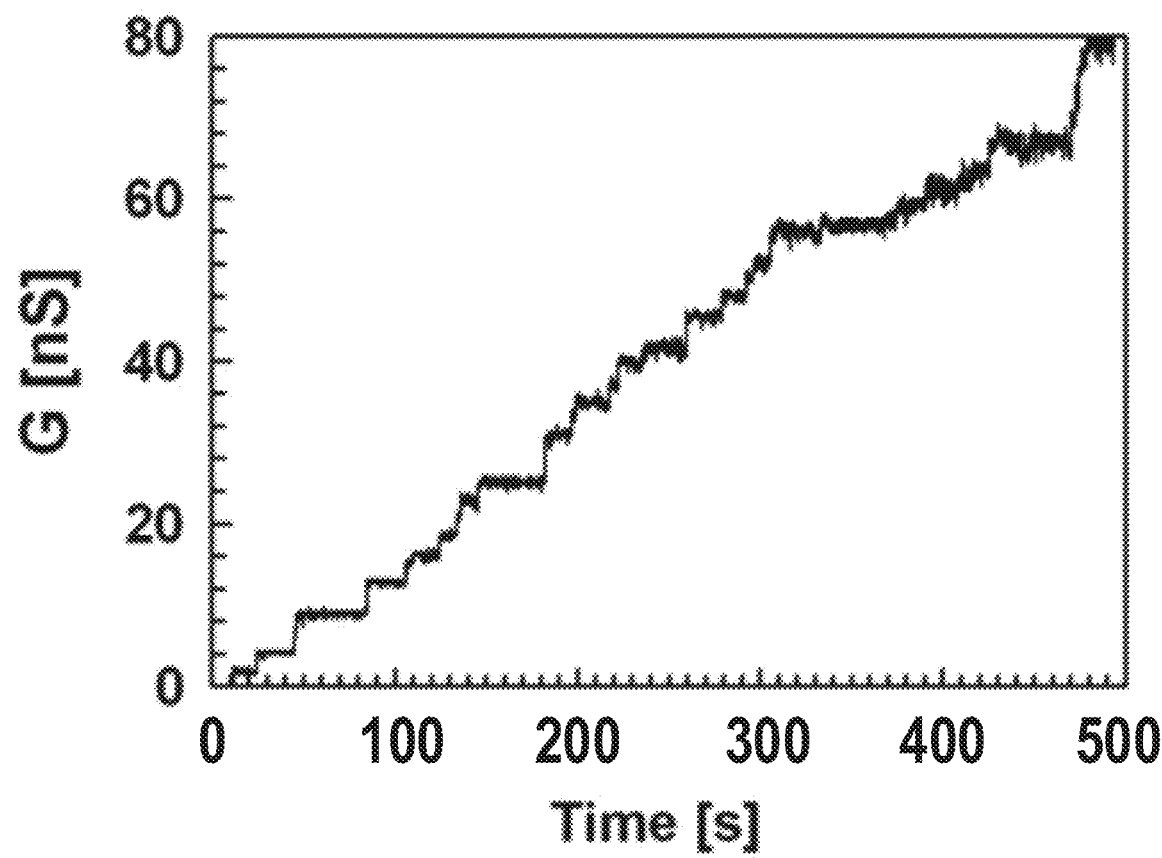
Figure 14B:
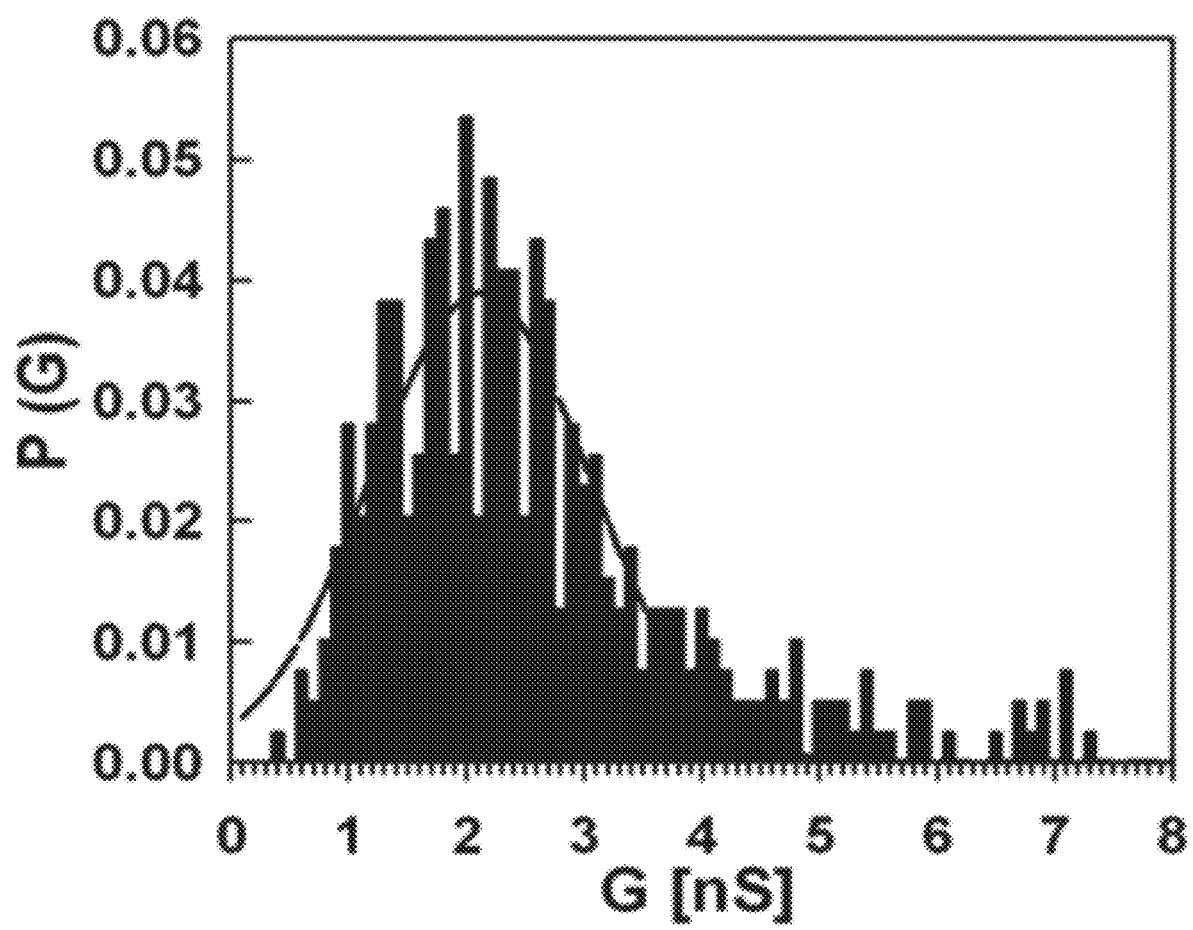

FIG. 14A and FIG. 14B show the channel-forming properties of scMspA M2. FIG. 14A shows a-current trace recording of scMspA M2 in planar lipid bilayer. After addition of refolded scMspA M2 protein as shown in FIG. 3 step-wise current increase is observed indicative of channel insertions. FIG. 14B shows a histogram of single-channel conductance distribution. A total of 392 channels from 8 membranes were analyzed. The dotted line represents a Gaussian fit of the data distribution. The major conductance of scMspA M2 is 2.3 nS.

Figure 15:
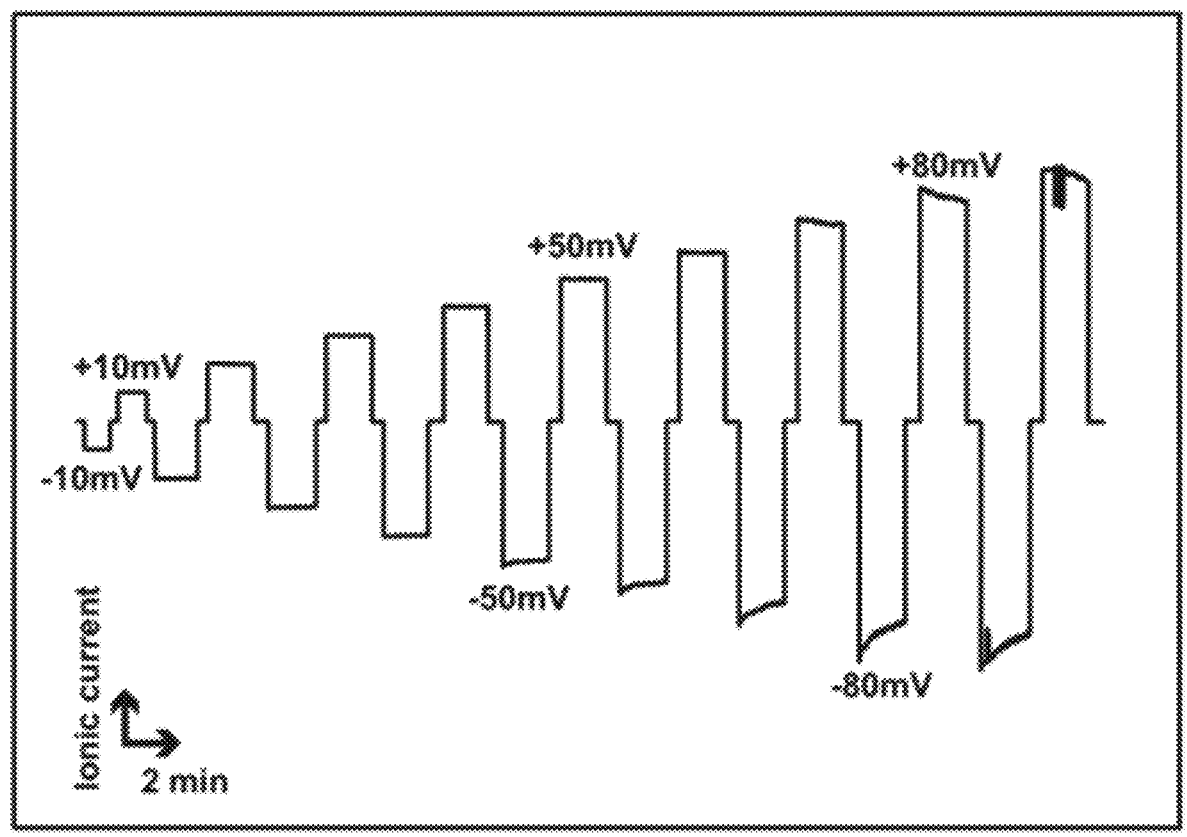

FIG. 15 shows voltage-dependent channel closure of scMspA M2. Protein was added to the cis-side of the cuvette. After insertion of approximately 200 pores, positive or negative voltage was increased in 10 mV increments and current was recorded for 2 minutes. A flat line represents open pores, whereas a sloping line represents closing of the pores. Critical voltages for scMspA M2 were determined to be about +80 mV/−70 mV.

Figure 16:
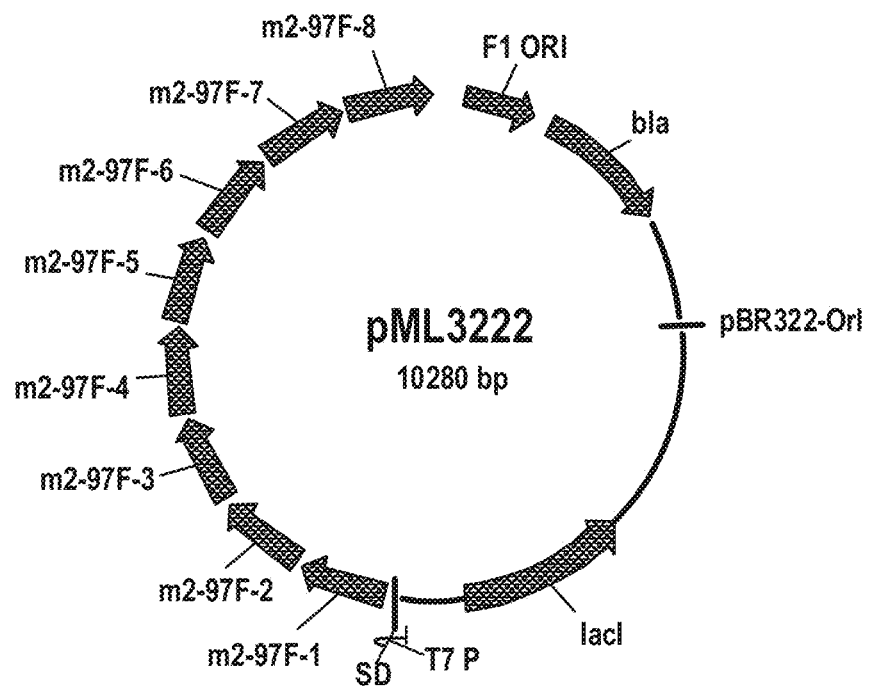

FIG. 16 shows a schematic representation of plasmid pML3222, for the expression of single-chain semspA PN1 (semspA PN1) in *E. coli*. bla, ampicillin resistance gene; pBR322-Ori, *E. coli* origin of replication; lacI, lac repressor protein; T7 P, T7 promoter; SD, Shine-Dalgarno sequence; m2-97-1-m2-97-8, codon optimized genes of m2 mspA with a P97F mutation.

Figure 17:
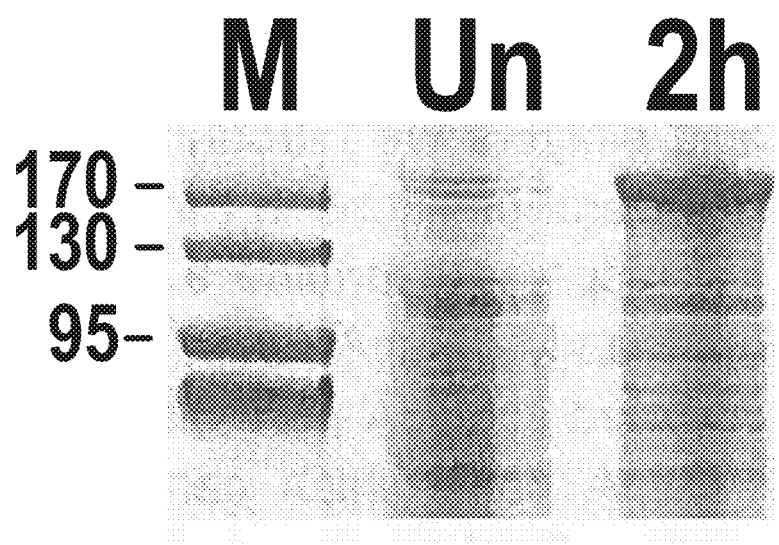

FIG. 17 shows that semspA PN1 can be produced in *E. coli*. *E. coli* Omp8 cells were induced with 1.5 mM IPTG at $OD_{600}$ of 0.5. At 2 hours post induction cells were collected and lysed. Equal amounts of protein sample were loaded onto 8% polyacrylamide gel. After electrophoresis, the gel was stained with Coomassie and scanned for quantification by LabWorks software (Waltham, Massachusetts). Lanes: M, molecular weight marker with masses indicated on the left (kDa); Un, non-induced cells; 2 hours after induction with IPTG.

Figure 18:
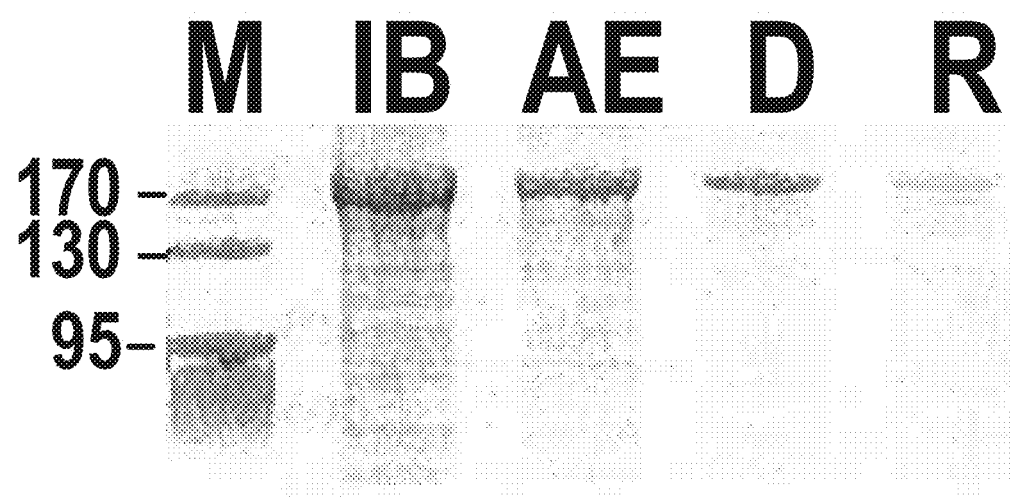

FIG. 18 shows a Western blot of scMspA PN1 refolding. Samples were loaded onto 8% polyacrylamide gel followed by staining with Coomassie and scanned for quantification by LabWorks software. Lanes: M, molecular weight marker with masses indicated on the left (kDa); IB, inclusion bodies purified from Omp8 *E. coli*; AE, sample after anion exchange chromatography; D, sample after dialysis; R, folded scMspA PN1 protein.

Figure 19:
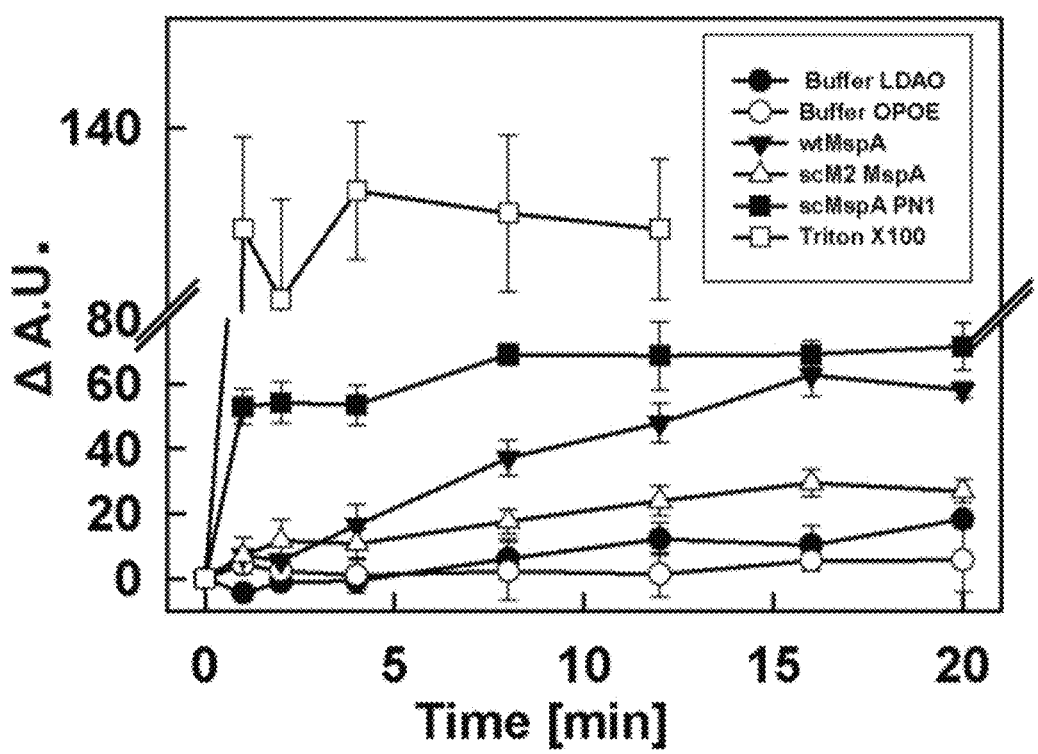

FIG. 19 shows that scMspA PN1 is inserted into lipid membranes. DPhPC liposomes were loaded with 30 mM carboxyfluorescein dye. Dye release was monitored at 517 nm emission (492 nm excitation) using Varian Cary fluorimeter (Palo Alto, CA). Symbols: open squares—Triton X-100 (0.1% v/v); closed circles—LDAO (0.1% v/v); open circles—OPOE (0.5% v/v); closed triangles—wtMspA (60 ng/ml); closed squares—scMspA PN1 (60 ng/ml), open triangles—scMspA M2 (120 ng/ml). No significant dye release was observed when liposomes where only in PBS buffer.

Figure 20:
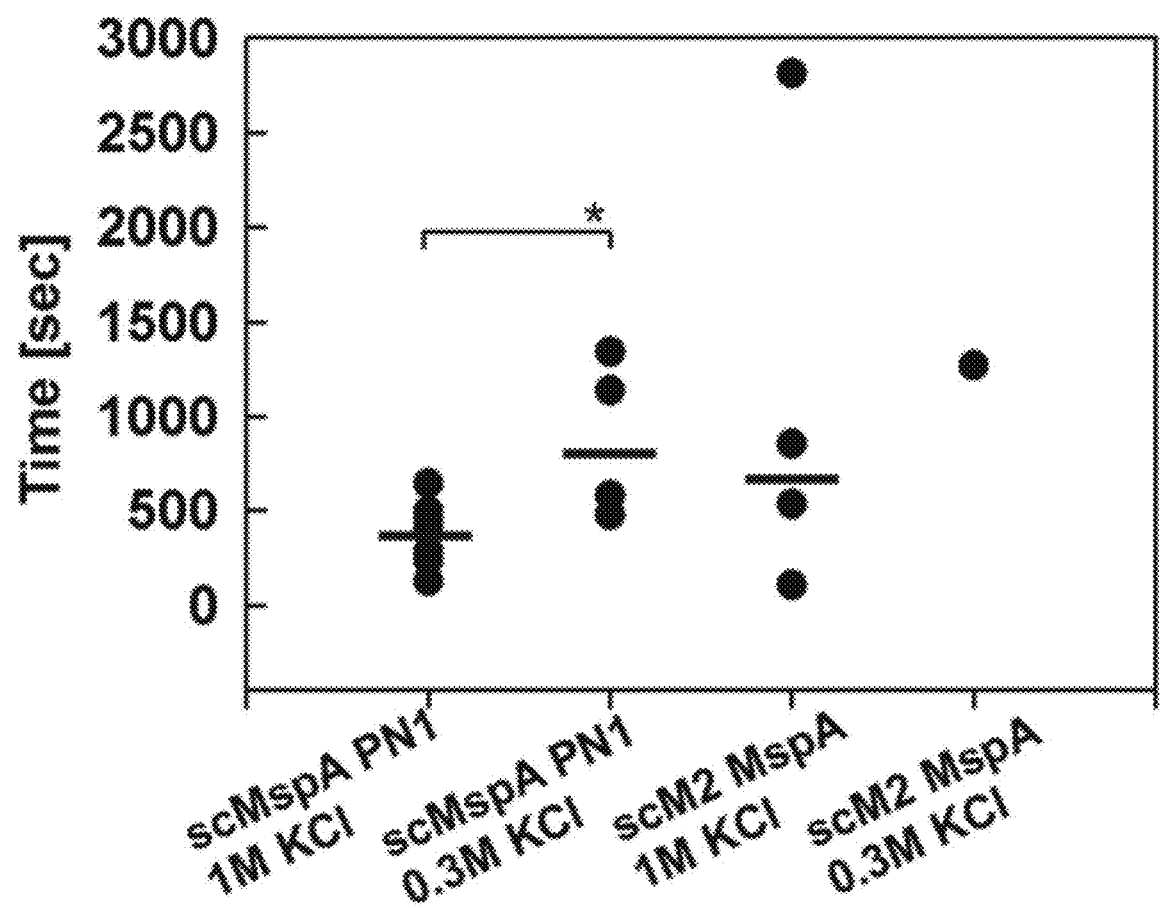
Figure 21A:
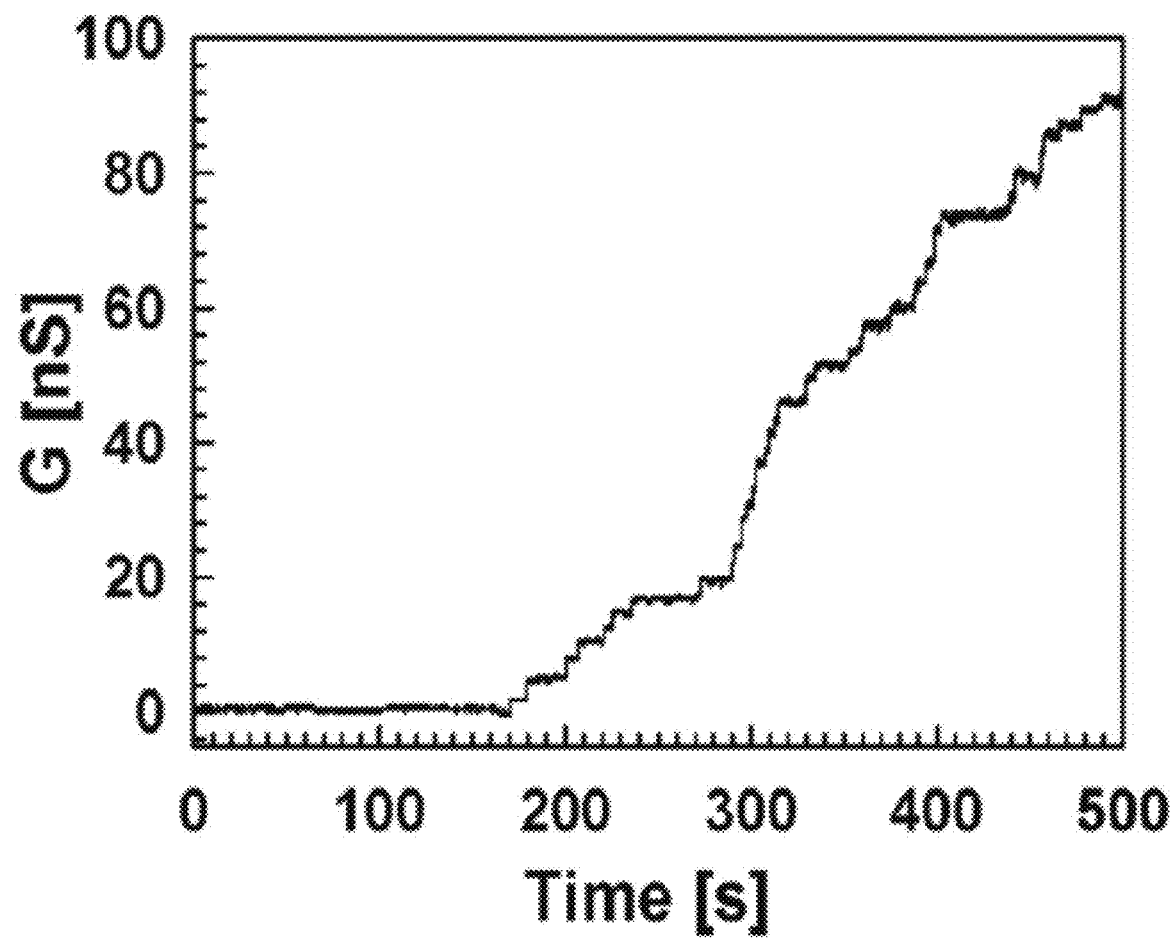
Figure 21B:
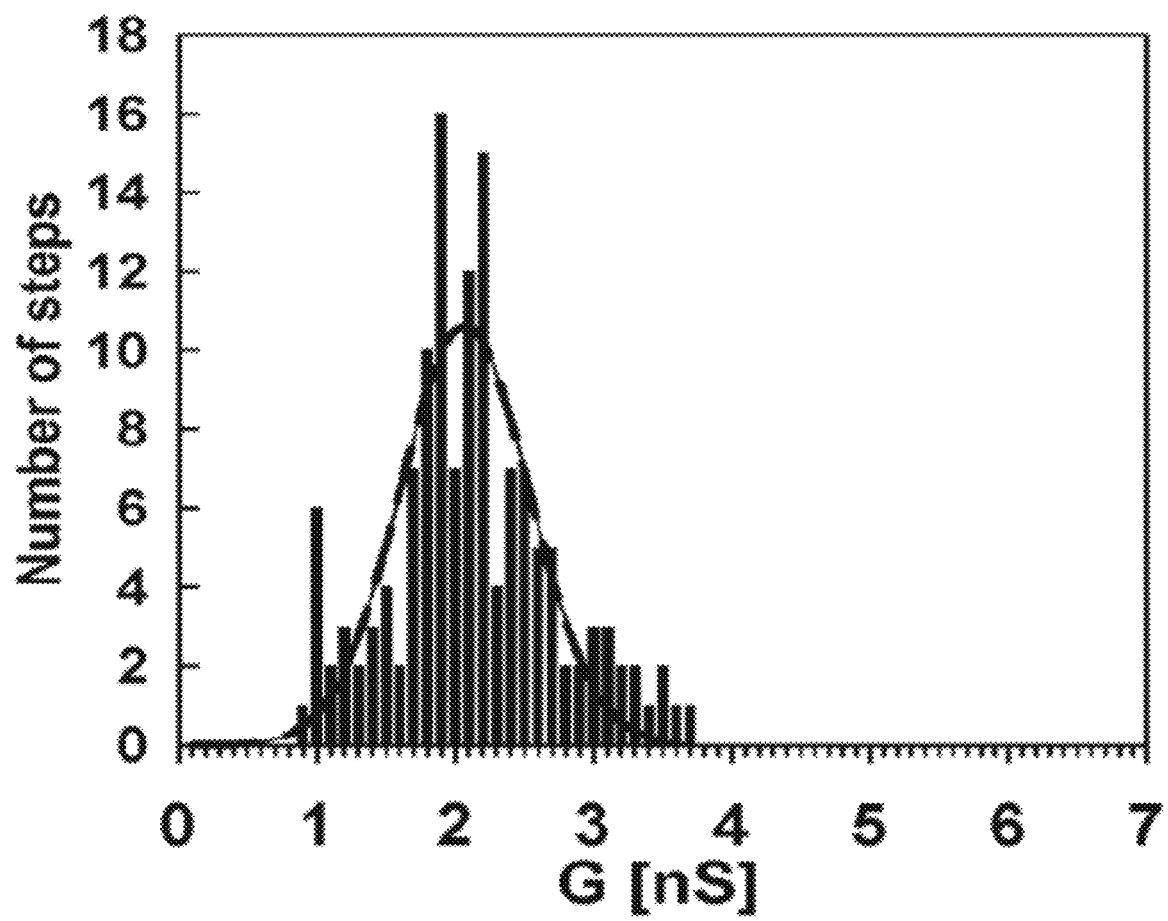
Figure 21C:
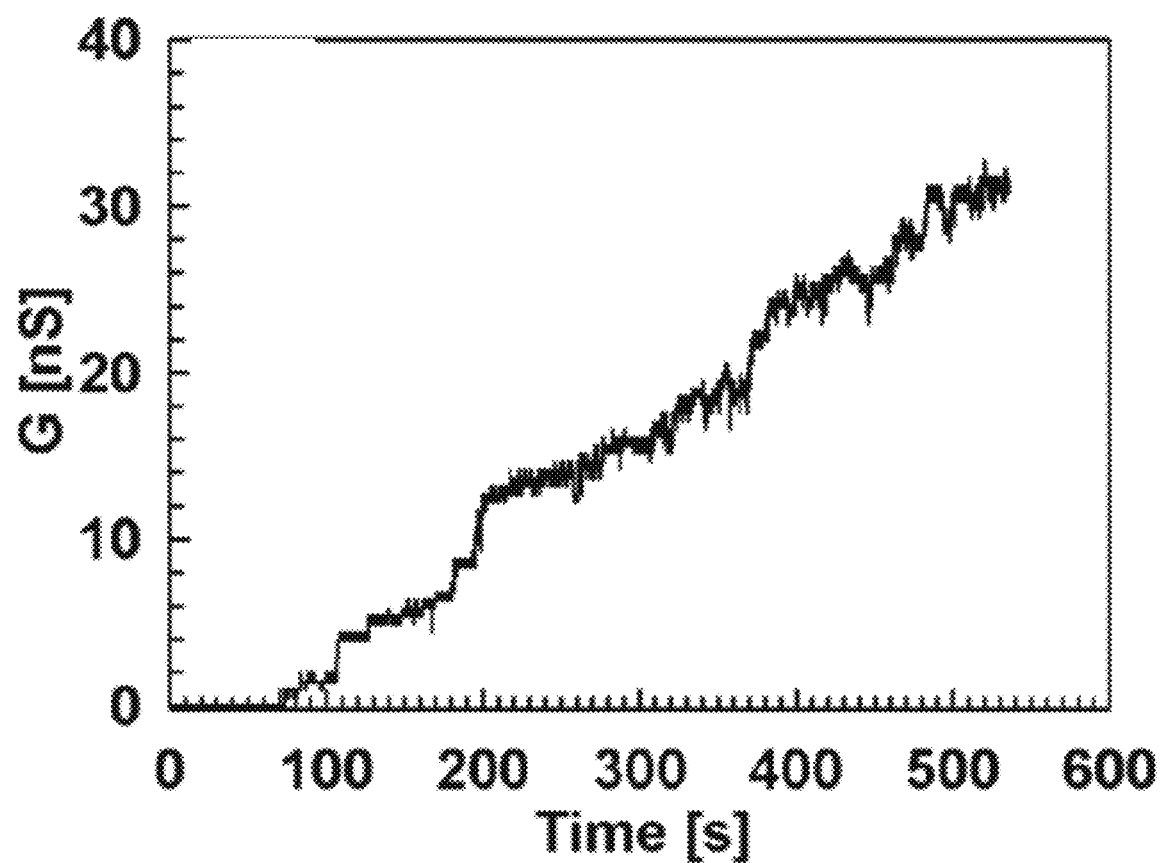
Figure 21D:
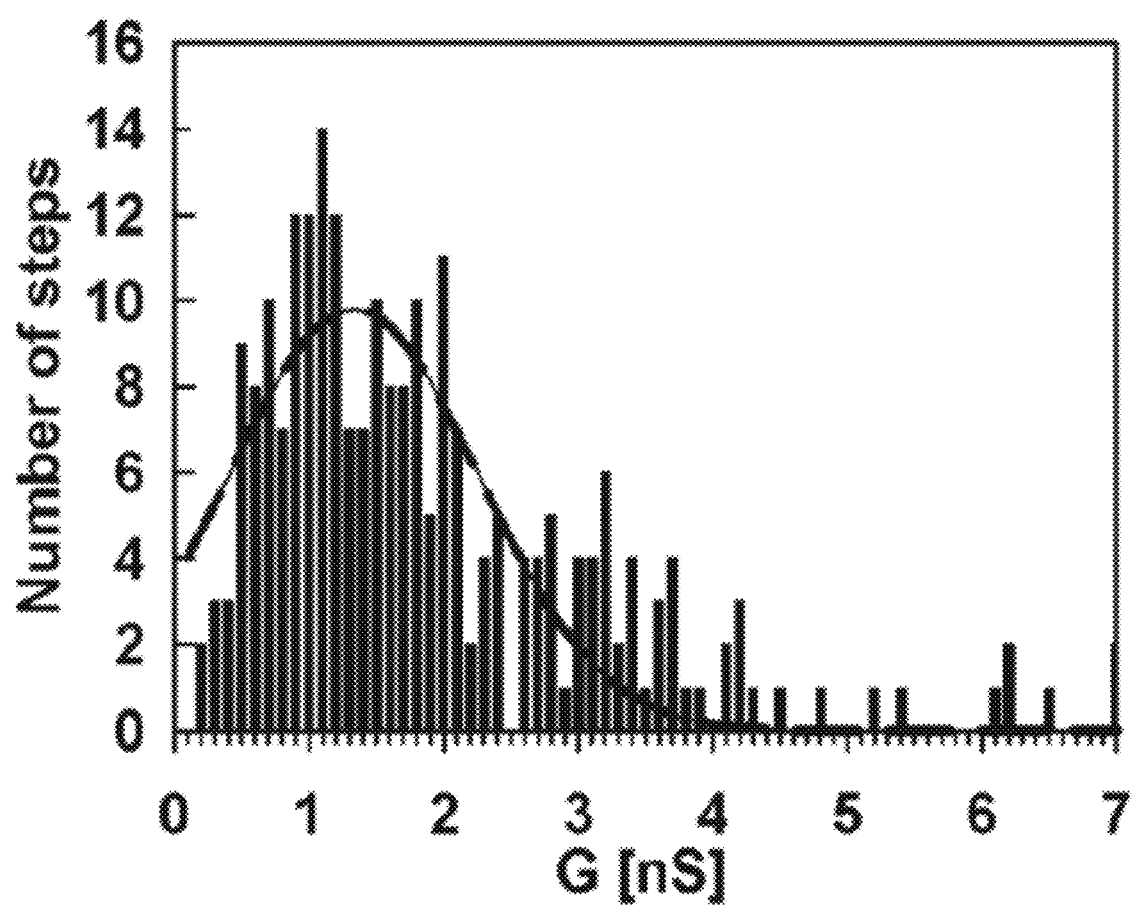

FIG. 20 shows the distribution of pores' reconstitution time into artificial DPhPC membrane. A cuvette was filled with KCl in the indicated concentrations. Protein samples of 100 ng/ml final were added to the both sides. −10 mV potential was applied and the data were recorded with TestPoint software. Each dot represents time of the first pore insertion. Median insertion time for scMspA PN1 in 1M KCl was 399 seconds (9 membranes with 89% successful insertion events analyzed). Median insertion time for scMspA PN1 in 0.3 MKCl was 859 seconds (8 membranes with 50% successful insertion events analyzed). Median insertion time for scMspA M2 in 1M KCl was 695 seconds (10 membranes with 40% successful insertion events analyzed). In 0.3M KCl scMspA M2 had insertion time of 1270 seconds (8 membranes, 12% successful insertion). *-P=0.028 as determined by Mann-Whitney Rank Sum test.

FIGS. 21(A-D) show single-channel conductances of scMspA PN1 and scMspA M2 in 1.0M KCl. FIG. 21A shows a current trace recording of scMspA PN1 in planar lipid bilayer. After addition of refolded scMspA PN1 protein a step-wise current increase is observed indicative of channel insertions. FIG. 21B shows a histogram of single-channel conductance distribution. A total of 137 channels from 4 membranes were analyzed. The dotted line represents a Gaussian fit of the data distribution. The major conductance of scMspA PN1 is 2.0 nS. FIG. 21C shows a current trace recording of scMspA M2 in planar lipid bilayer. FIG. 21D shows a histogram of single-channel conductance distribution. A total of 238 channels from 6 membranes were analyzed. The dotted line represents a Gaussian fit of the data distribution. The major conductance of scMspA M2 is 1.3 nS.

Figure 22:
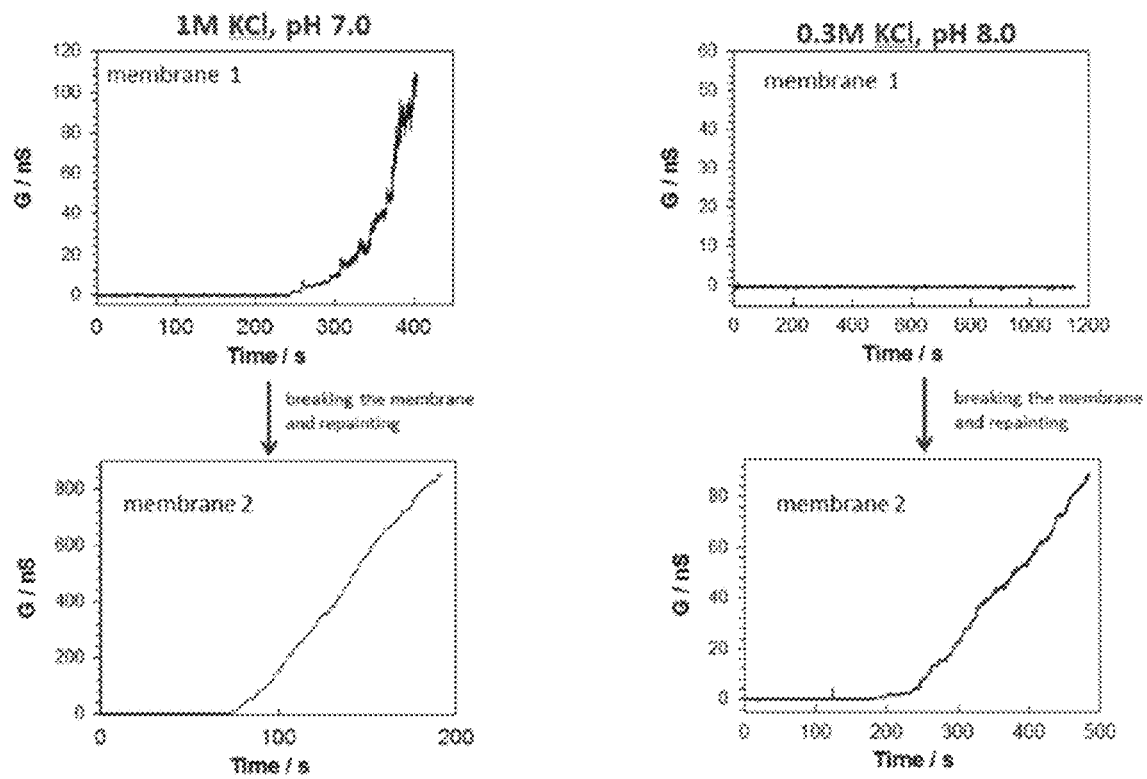

FIG. 22 shows single channel conductance of single-chain MspA PN1 at 0.3M KCl and 1.0M KCl and the increase of channel insertions of scMspA PN1 into membranes at 0.3M KCl after it was in contact with membranes.

DETAILED DESCRIPTION

Figure 1:
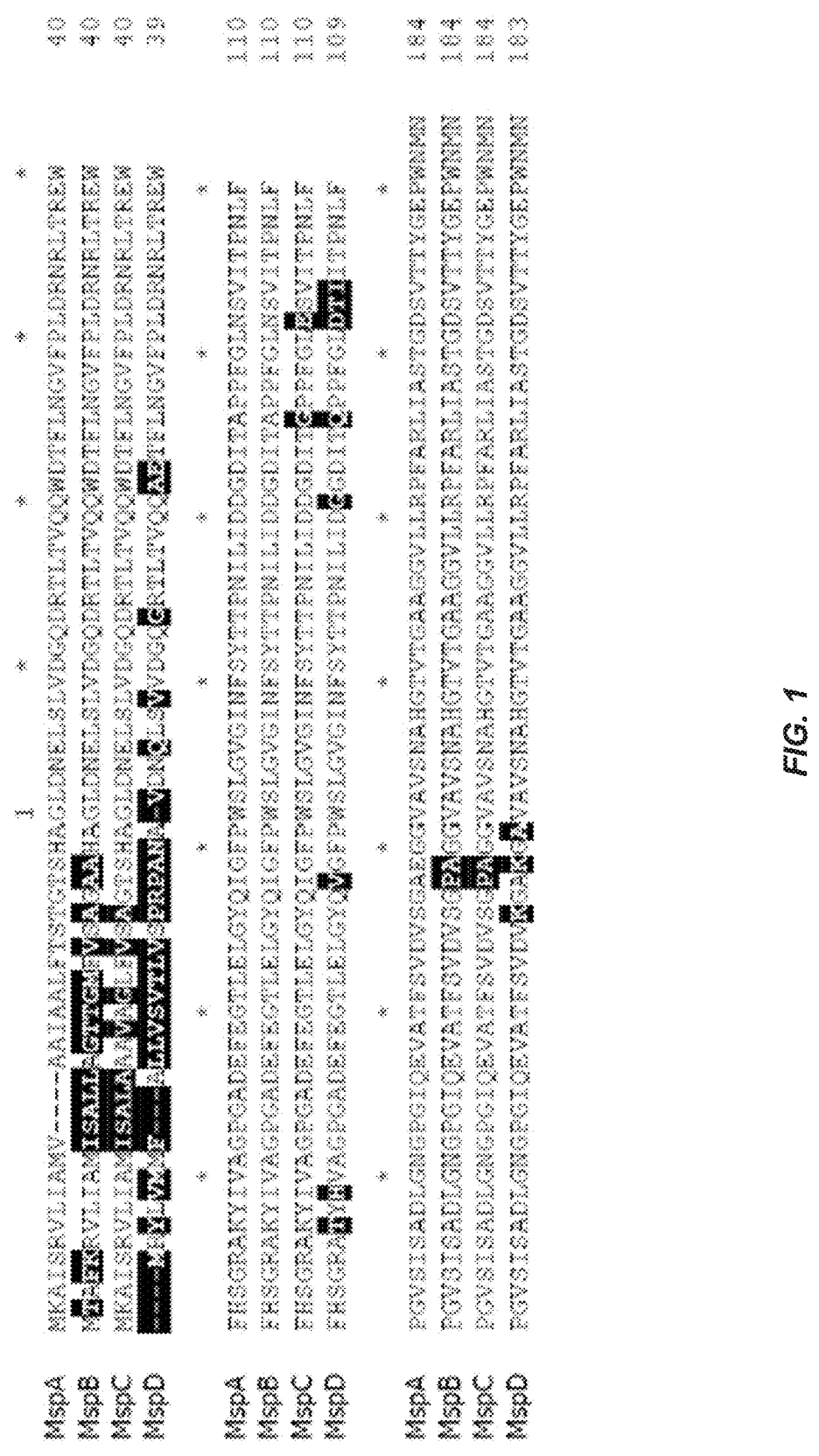

Provided herein are mutant *Mycobacterium smegmatis* porins (Msp). A mutant Msp can be a multimer complex comprised of two or more Msp monomers, wherein at least one of the monomers is a mutant Msp monomer. An Msp monomer is encoded by a gene in *Mycobacterium smegmatis*. *Mycobacterium smegmatis* has four identified Msp genes, denoted MspA, MspB, MspC, and MspD. An alignment of the wild-type polypeptide sequences for the MspA, MspB, MspC and MspD monomers of *Mycobacterium smegmatis* is shown in FIG. 1. The numbering of each protein starts with the first amino acid of the mature portion of the sequence, as indicated by the number "1" above the first amino acid of the mature amino acid sequence. The amino acid sequences for a MspA, MspB, MspC and a MspD monomer without a signal sequence, i.e., the mature portion of the sequence, are provided as SEQ ID NO: 1, SEQ ID NO: 2, SEQ ID NO: 3 and SEQ ID NO: 4, respectively. The amino acid sequences for a MspA, MspB, MspC and a MspD monomer with a signal/leader sequence are provided as SEQ ID NO: 6, SEQ ID NO: 7, SEQ ID NO: 8 and SEQ ID NO: 9, respectively.

Further, sequences of wild-type Msp monomers that can be modified are disclosed in GenBank, and these sequences and others are herein incorporated by reference in their entireties as are individual subsequences or fragments contained therein. For example, the nucleotide and amino acid sequences of a wild-type MspA monomer can be found at GenBank Accession Nos. AJ001442 and CAB56052, respectively. The nucleotide and amino acid sequences of a wild-type MspB monomer can be found, for example, at GenBank Accession Nos. NC_008596.1 (from nucleotide 600086 to 600730) and YP 884932.1, respectively. The nucleotide and amino acid sequences of a wild-type MspC monomer can be found, for example, at GenBank Accession Nos. AJ299735 and CAC82509, respectively. The nucleotide and amino acid sequences of a wild-type MspD monomer can be found, for example, at GenBank Accession Nos. AJ300774 and CAC83628, respectively.

A mutant Msp monomer can be a full-length monomer or a functional fragment thereof encoded by a MspA, MspB, MspC or MspD-encoding nucleic acid, for example, an mRNA or a genomic sequence encoding MspA, MspB, MspC or MspD, wherein the monomer comprises one or more modifications.

Optionally, a mutant Msp is a mutant single-chain Msp or is a multimer of several single-chain Msps, wherein the multimer comprises at least one mutant single-chain Msp. A mutant Msp can also be a multimer of several Msp monomers wherein at least one Msp monomer is a mutant Msp monomer.

A single-chain Msp can, for example, comprise a multimer formed by two or more Msp monomers (e.g., eight monomers) connected by one or more amino acid linker peptides. A partial single-chain Msp refers to a single-chain multimer complex that dimerizes, trimerizes, or the like to form a porin. A full single-chain Msp porin refers to a single-chain multimer complex that forms a porin without the need to dimerize, trimerize or the like to form a porin. Stated differently, the single-chain folds to form a porin, but all components are in one amino acid chain, as compared to a porin that must associate with other partial single-chain Msp(s) or monomeric Msp monomers to form a porin.

Mutant Single-Chain Msps and the Nucleic Acids Encoding Them

Provided herein are nucleic acid sequences encoding mutant single-chain Msps. For example, the nucleic acid sequence encoding a mutant single-chain Msp comprises: (a) a first and second nucleotide sequence, wherein the first nucleotide sequence encodes a first Msp monomer sequence and the second nucleotide sequence encodes a second Msp monomer sequence; and (b) a third nucleotide sequence encoding an amino acid linker sequence, wherein at least one of the first and second Msp monomer sequences is a mutant Msp monomer sequence has a mutation at position P97. Optionally, the mutant Msp monomer sequence can comprise a mutation at P97, wherein the mutation is not a P97S mutation or a P97C mutation. Optionally, the mutant Msp monomer sequence can comprise a P97F mutation. As shown in the Examples, additional hydrophobic residues, for example, phenylalanine, located in loop 6 of scMspA (amino acids 91-103) promote faster and more efficient insertion of the pores into lipid bilayers. For a description of loop 6 of MspA and residues contained therein, see Huffe et al., *J. Biol. Chem.* 284: 10223-10231 (2009), which is hereby incorporated in its entirety by this reference. Therefore, provided herein is a single chain Msp comprising one or more hydrophobic substitutions in loop 6 (amino acids 91-103) of Msp.

For example, provided herein is a nucleic acid sequence encoding a mutant single-chain *Mycobacterium smegmatis* porin (Msp), wherein the nucleic acid sequence comprises (a) a first and second nucleotide sequence, wherein the first nucleotide sequence encodes a first Msp monomer sequence and the second nucleotide sequence encodes a second Msp monomer sequence and (b) a third nucleotide sequence encoding an amino acid linker sequence, wherein at least one of the first and second Msp monomer sequences is a mutant Msp monomer sequence comprising one or more mutations at any of amino acid positions D91, G92, D93, I94, T95, A96, P97, P98, F99, G100, L101, N102 or S103, wherein one or more of D91, G92, D93, I94, T95, A96, P97, P98, F99, G100, L101, N102 or S103 is substituted with a hydrophobic amino acid. For example, hydrophobic amino acids can be selected from the group consisting of alanine, valine, leucine, isoleucine, proline, phenylalanine, methionine, tyrosine, tryptophan, proline and glycine. By way of example, and not to be limiting, a mutant Msp monomer sequence can comprise (i) a D90N, a D91N and a D93N mutation; and one or more of (ii) a G92F, T95F, A96F, P97F, P98F, G100F, L101F, N102F or S103F mutation. As set forth above, substitutions at position G92, T95, A96, P97, P98, G100, L101, N102 or S103 are not limited to phenylalanine, as one or more of these amino acids can be replaced with another hydrophobic residue, for example, alanine, valine, leucine, isoleucine, proline, methionine, tyrosine, tryptophan, proline and glycine. One or more of G92, T95, A96, P97, P98, G100, L101, N102 or S103 can be substituted with the same hydrophobic amino acid or different hydrophobic amino acids.

As used throughout, a mutation at a specific amino acid is indicated by the single letter code for the amino acid at a position, followed by the number of the amino acid position in an Msp polypeptide sequence (for example, an amino acid position in SEQ ID NO: 1), and the single letter code for the amino acid substitution at this position. Therefore, it is understood that a P97 mutation is a proline to phenylalanine substitution at amino acid 97 of SEQ ID NO: 1. Similarly, a D90N mutation is an aspartic acid to arginine substitution at amino acid 90 of SEQ ID NO: 1, a D91N mutation is an aspartic to arginine substitution at amino acid 91 of SEQ ID NO: 1, etc. It is also understood that amino acids corresponding to positions in SEQ ID NO: 1 are also provided herein (See FIG. 1). For example, and not to be limiting, one of skill in the art would understand that, the corresponding amino acid for E139 of SEQ ID NO: 1 in MspB (SEQ ID NO:2), MspC (SEQ ID NO: 3) and MspD (SEQ ID NO: 4) is A139, A139 and K138, respectively.

Optionally, any mutant Msp monomer sequence described herein can further comprise a mutation at amino acid position D118, a mutation at position D134 or a mutation at position E139. Optionally, a mutation at position E139 can be an E to R (arginine) or an E to K (lysine) substitution. Optionally, a mutation at position D118 can be a D to R substitution or a D to K substitution. Optionally, a mutation at position D134 can be a D to R substitution or a D to K substitution. For example, any mutant Msp monomer sequence described herein can comprise one or more mutations selected from the group consisting of: a D118R mutation, a D134R mutation and a E139K mutation. Optionally, any mutant Msp monomer sequence described herein can further comprise at least one of (i) a mutation at position 93 and (ii) a mutation at position D90, position D91 or both positions D90 and D91. Optionally, the amino acid at position 90, 91 or 93 is substituted with arginine, lysine, histidine, glutamine, methionine, threonine, phenylalanine, tyrosine or tryptophan. Optionally, any mutant Msp monomer sequence described herein can further comprise a D90N, a D91N and a D93N mutation.

For example, a mutant Msp monomer sequence comprising a mutation at position 97 can further comprise (i) a mutation at amino acid position D118, D134 and/or E139 (ii) a mutation at position D93, and/or (iii) a mutation at position D90, position D91 or both positions D90 and D91. For example, a mutant MspA monomer sequence can comprise a D90N mutation, a D91N mutation, a D93N mutation, a P97F mutation, a D118R mutation, a D134R mutation and a E139K mutation. The mutant MspA monomer sequence can also comprise a D90N mutation, a D91N mutation, a D93N mutation, a P97F mutation, a D118R mutation, a D134R mutation and a E139K mutation.

Also provided herein is a nucleic acid sequence encoding a mutant single-chain Msp which comprises (a) a first and second nucleotide sequence, wherein the first nucleotide sequence encodes a first Msp monomer sequence and the second nucleotide sequence encodes a second Msp monomer sequence, and (b) a third nucleotide sequence encoding an amino acid linker sequence, wherein at least one of the first and second Msp monomer sequences is a mutant Msp monomer sequence comprising one or more mutations at any of the following amino acid positions: I68, S73, S116, P123 or V128. Provided herein is a nucleic acid encoding a mutant single-chain Msp, wherein the mutant Msp monomer sequence comprises one or more mutations at any of I68, S73, S116, P123 or V128, wherein the mutation is not a I68V mutation or a S73C mutation.

Provided herein is a mutant Msp monomer sequence comprising one or more mutations at I68, S73, S116, P123 and/or V128 further comprising (i) a mutation at amino acid position D118, (ii) a mutation at position D93, and/or (iii) a mutation at position D90, position D91 or both positions D90 and D91. For example, a mutant MspA monomer sequence can comprise one or more mutations at amino acid positions I68, S73, S116, P123 or V128, a mutation at D93, a mutation at D118, a mutation at D134 and a mutation at E139 or any subset thereof. In another example, a mutant MspA monomer sequence can comprise one or more mutations at amino acid positions I68, S73, S116, P123 or V128, a mutation at amino acid position D118, a mutation at D134, a D90N mutation and/or a D91N mutation. In yet another example, a mutant MspA monomer sequence can comprise one or more mutations at amino acid positions I68, S73, S116, P123 or V128, a mutation at amino acid position D118, a mutation at D134 and a mutation at E139, a D90N mutation, a D91N mutation and a D93N mutation. Provided herein is a nucleic acid encoding a mutant single-chain Msp, wherein the mutant Msp monomer sequence comprises one or more mutations at any of I68, S73, S116, P123 or V128, wherein the mutation is not a I68V mutation or a S73C mutation. In any of the mutant single-chain Msps provided herein, the mutant Msp monomer sequence can comprise one or more mutations at any of I68, S73, S116, P123 or V128, wherein the mutation is not a I68V mutation or a S73C mutation.

Optionally, any of the mutant Msp monomer sequences described herein can further comprise one or more mutations at any of the following amino acid positions: D13, A55, D56, E57, F58, E63, S136, G137 or D172. Optionally, one or more of D13, A55, D56, E57, F58, E63, S136, G137 or D172 in a mutant Msp monomer sequence provided herein can be substituted with lysine or arginine. Optionally, any mutant Msp monomer sequence described herein comprising one or more mutations at D13, A55, D56, E57, F58, E63, S136, G137 or D172 can further comprise one or more mutations at the following positions: D118, D134 or E139. Optionally, any mutant Msp monomer sequence described herein comprising one or more mutations at D13, A55, D56, E57, F58, E63, S136, G137 or D172 can further comprise a mutation at position 93, and/or a mutation at position 90, position 91 or both positions 90 and 91.

Therefore, provided herein is a nucleic acid sequence encoding a mutant single-chain *Mycobacterium smegmatis* porin (Msp), wherein the nucleic acid sequence comprises (a) a first and second nucleotide sequence, wherein the first nucleotide sequence encodes a first Msp monomer sequence and the second nucleotide sequence encodes a second Msp monomer sequence, and (b) a third nucleotide sequence encoding an amino acid linker sequence, wherein at least one of the first and second Msp monomer sequences is a mutant Msp monomer sequence comprising one or more mutations at any of the following amino acid positions: D13, A55, D56, E57, F58, E63, S136, G137 or D172. Optionally, the third nucleotide sequence encoding the linker is located between the first and second nucleotide sequence.

Also provided is a nucleic acid sequence encoding a mutant single-chain *Mycobacterium smegmatis* porin (Msp), wherein the nucleic acid sequence comprises: (a) a first and second nucleotide sequence, wherein the first nucleotide sequence encodes a first Msp monomer sequence and the second nucleotide sequence encodes a second Msp monomer sequence, and (b) a third nucleotide sequence encoding an amino acid linker sequence, wherein at least one of the first and second Msp monomer sequences is a mutant Msp monomer sequence comprising (i) a mutation at position 93, and/or (ii) a mutation at position 90, position 91 or both positions 90 and 91 and (iii) one or more mutations at any of the following amino acid positions: D13, A55, D56, E57, F58, E63, S136, G137 or D172.

Further provided is a nucleic acid encoding a mutant Msp monomer, wherein the Msp monomer comprises a mutation at one or more of the following positions: D13, A55, D56, E57, F58, E63, S136, G137 or D172. Optionally, a mutant Msp monomer sequence comprising one or more mutations at D13, A55, D56, E57, F58, E63, S136, G137 or D172 can further comprise a mutation at position 93 and/or a mutation at position 90, position 91 or both positions 90 and 91. Optionally, a mutant Msp monomer sequence comprising one or more mutations at positions D13, A55, D56, E57, F58, E63, S136, G137 or D172 can further comprise a D90N, a D91N and a D93N mutation.

In the mutant single-chain mutant Msps provided herein, the first monomer sequence can be any mutant monomer sequence described herein. For example, the mutant monomer sequence can be a mutant MspA sequence. The second monomer can be selected from the group consisting of a wildtype Msp monomer, a second mutant Msp monomer, a wild-type Msp paralog or homolog monomer, and a mutant Msp paralog or homolog monomer. It is understood that the second mutant Msp monomer can be the same or different than the first mutant Msp monomer. These include, but are not limited to, MspA/Msmeg0965, MspB/Msmeg0520, MspC/Msmeg5483, MspD/Msmeg6057, MppA, PorM1, PorM2, PorM1, Mmcs4296, Mmcs4297, Mmcs3857, Mmcs4382, Mmcs4383, Mjls3843, Mjls3857, Mjls3931 Mjls4674, Mjls4675, Mjls4677, Map3123c, Mav3943, Mvan1836, Mvan4117, Mvan4839, Mvan4840, Mvan5016, Mvan5017, Mvan5768, MUL_2391, Mflv1734, Mflv1735, Mflv2295, Mflv1891, MCH4691c, MCH4689c, MCH4690c, MAB1080, MAB1081, MAB2800, RHAI ro08561, RHA1 ro04074, and RHA1 ro03127. A wild-type MspA paralog or homolog monomer may be a wild-type MspB monomer. Wild-type MspA paralog and homolog monomers are well-known in the art. Table 1 provides a non-limiting list of such paralogs and homologs.

TABLE 1

Wild-type MspA and Wild-type MspA paralogs and homolog monomers

| Protein# | Organism | Identity/ Similarity to MspA (%) | Length (aa) | Reference |
|---|---|---|---|---|
| MspA/Msmeg0965 | *M. smegmatis* | 100/100 | 211 | gb\|ABK74363.1\|, (Stahl et al., 2001)* |
| MspB/Msmeg0520 | *M. smegmatis* | 94/95 | 215 | gb\|ABK73437.1\|, (Stahl et al., 2001)* |
| MspC/Msmeg5483 | *M. smegmatis* | 93/95 | 215 | gb\|ABK74976.1\|, (Stahl et al., 2001)* |
| MspD/Msmeg6057 | *M. smegmatis* | 82/89 | 207 | gb\|ABK72453.1\|, (Stahl et al., 2001)* |

TABLE 1-continued

Wild-type MspA and Wild-type MspA paralogs and homolog monomers

| Protein# | Organism | Identity/ Similarity to MspA (%) | Length (aa) | Reference |
|---|---|---|---|---|
| MppA | M. phlei | 100/100 | 211 | AJ812030, (Dorner et at., 2004)** |
| PorM1 | M. fortuitum | 95/96 | 211 | emb\|CAI54228.1\| |
| PorM2 | M. fortuitum | 91/93 | 215 | emb\|CAL29811.1\| |
| PorM1 | M. peregrinum | 94/96 | 211 | emb\|CAI54230.1\| |
| Mmcs4296 | Mycobacterium sp. MCS | 85/91 | 216 | gb\|ABG10401.1\| |
| Mmcs4297 | Mycobacterium sp. MCS | 85/91 | 216 | gb\|ABG10402.1\| |
| Mmcs3857 | Mycobacterium sp. MCS | 30/44 | 235 | gb\|ABG09962.1\| |
| Mmcs4382 | Mycobacterium sp. MCS | 85/91 | 216 | gb\|ABL93573.1\| |
| Mmcs4383 | Mycobacterium sp. MCS | 85/91 | 216 | gb\|ABL93574.1\| |
| Mjls3843 | Mycobacterium sp. JLS | 26/40 | 235 | gb\|ABN99619.1\| |
| Mjls3857 | Mycobacterium sp. JLS | 26/40 | 235 | gb\|ABG09962.1\| |
| Mjls3931 | Mycobacterium sp. JLS | 26/40 | 235 | gb\|ABL93123.1\| |
| Mjls4674 | Mycobacterium sp. JLS | 85/89 | 216 | gb\|ABO00440.1\| |
| Mjls4675 | Mycobacterium sp. JLS | 83/89 | 216 | gb\|ABO00441.1\| |
| Mjls4677 | Mycobacterium sp. JLS | 84/89 | 216 | gb\|ABO00443.1\| |
| Map3123c | M. avium paratuberculosis | 24/39 | 220 | gb\|AAS05671.1\| |
| Mav3943 | M. avium | 24/39 | 227 | gb\|ABK66660.1\| |
| Mvan1836 | M. vanbaalenii PYR-1 | 82/88 | 209 | gb\|ABM12657.1\| |
| Mvan4117 | M. vanbaalenii PYR-1 | 32/43 | 239 | gb\|ABM14894.1\| |
| Mvan4839 | M. vanbaalenii PYR-1 | 83/88 | 209 | gb\|ABM15612.1\| |
| Mvan4840 | M. vanbaalenii PYR-1 | 83/89 | 209 | gb\|ABM15613.1\| |
| Mvan5016 | M. vanbaalenii PYR-1 | 30/41 | 238 | gb\|ABM15788.1\| |
| Mvan5017 | M. vanbaalenii PYR-1 | 25/35 | 227 | gb\|ABM15789.1\| |
| Mvan5768 | M. vanbaalenii PYR-1 | 21/32 | 216 | gb\|ABM16533.1\| |
| MUL_2391 | M. ulcerans Agy99 | 21/34 | 233 | gb\|ABL04749.1\| |
| Mflv1734 | M. gilvum PYR-GCK | 21/32 | 225 | gb\|ABP44214.1\| |
| Mflv1735 | M. gilvum PYR-GCK | 32/41 | 226 | gb\|ABP44215.1\| |
| Mflv2295 | M. gilvum PYR-GCK | 25/40 | 250 | gb\|ABP44773.1\| |
| Mflv1891 | M. gilvum PYR-GCK | 84/90 | 217 | gb\|ABP44371.1\| |
| MCH4691c | M. chelonae | 70/80 | 223 | gb\|ACV04474.1\| |
| MCH4689c | M. chelonae | 66/78 | 223 | gb\|ACV04472.1\| |
| MCH4690c | M. chelonae | 72/81 | 217 | gb\|ACV04473.1\| |
| MAB1080 | M. abscessus | 69/79 | 223 | emb\|CAM61170.1\| |
| MAB1081 | M. abscessus | 68/78 | 222 | emb\|CAM61171.1\| |
| MAB2800 | M. abscessus | 27/44 | 246 | emb\|CAM62879.1\| |
| RHA1 ro08561 | Rhodococcus jostii RHA1 | 34/51 | 233 | gb\|ABG99605.1\| |
| n.d. | Rhodococcus opacus B4 | 34/51 | 233 | gbj\|BAH52196.1\| |
| RHA1 ro04074 | Rhodococcus sp. RHA1 | 34/50 | 233 | gb\|ABG95871.1\| |
| RHA1 ro03127 | Rhodococcus sp. RHA1 | 34/50 | 233 | gb\|ABG94930.1\| |
| n.d. | Rhodococcus erythropolis PR4 | 35/50 | 229 | gbj\|BAH30938.1\| |

Only proteins with significant amino acid similarities over the full length of the protein were included. Data were obtained by PSI-Blast algorithm (BLOSUM62 matrix) using the NIH GenBank database on the world wide web at ncbi.nlm.nih.gov/blast/Blast.cgi.
n.d.: "not determined"
*Stahl etal., Mol. Microbial. 40:451 (2001)
**Dorner et al., Biochim. Biophys. Acta. 1667:47-55 (2004)

As used herein, a mutant single-chain Msp is a polypeptide comprising at least two Msp monomers, or functional fragments thereof, connected by one or more amino acid linker peptides wherein at least one of the Msp monomers is a mutant Msp monomer. For example, the mutant single-chain Msp can comprise two, three, four, five, six, seven, eight, nine, ten, eleven, twelve, or more Msp monomers connected by one or more amino acid linker peptides, wherein at least one of the Msp monomers is a mutant Msp monomer. As set forth above, a single-chain mutant Msp can form a porin, for example, by folding, without the need to dimerize, trimerize or the like to form a porin. Alternatively, a mutant single-chain Msp can be a partial single-chain mutant Msp comprising at least two Msp monomers or fragments thereof connected by one or more amino acid linked peptides, that can dimerize, trimerize or the like to form a porin.

Optionally, a Msp porin comprising a mutant single-chain Msp can, for example, comprise two or more single-chain Msp porin dimers, two or more single-chain Msp porin trimers, two or more single-chain Msp porin quadrimers, two or more single-chain Msp porin pentamers, one or more single-chain Msp porin hexamers, one or more single-chain Msp porin septamers, one or more single-chain Msp porin octamers, or combinations thereof. For example, a Msp porin can comprise a single-chain Msp porin dimer and two single-chain Msp porin trimers. By way of another example, a Msp porin can comprise a single-chain Msp porin quadrimer and two single-chain Msp porin dimers.

Amino acid linker sequences are described herein. In any single-chain Msp described herein, a linker sequence can, for example, comprise 10 to 20 amino acids. For example, an amino acid linker sequence comprises 15 amino acids. Optionally, the amino acid linker sequence comprises a (GGGGS)$_3$ (SEQ ID NO: 5) peptide sequence. The same or different nucleic acid encoding linker sequence can be provided between nucleic acid sequences encoding more than two Msp monomers. Optionally, a linker sequence can be provided between all or some of the nucleic acid sequences encoding Msp monomers in the single chain Msps provided herein.

Further provided is a nucleic acid sequence encoding a mutant single-chain Msp, wherein the nucleic acid sequence comprises (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence, wherein the first Msp monomer sequence is a mutant Msp monomer sequence that comprises a mutation at position P97.

The mutant Msp monomer sequence can comprise a mutation at P97, wherein the mutation is not a P97S mutation or a P97C mutation. The mutant Msp monomer sequence can comprise a P97F mutation. As set forth above, any mutant Msp monomer sequence described herein can further comprise a mutation at amino acid position D118, a mutation at position D134 or a mutation at position E139. For example, any mutant Msp monomer sequence described herein can comprise a D118R mutation, a D134R mutation and/or a E139K mutation. Any mutant Msp monomer sequence described herein can further comprise (i) a mutation at position 93 and/or (ii) a mutation at position D90, position D91 or both positions D90 and D91. Optionally, the amino acid at position 90, 91 or 93 is substituted with arginine, lysine, histidine, glutamine, methionine, threonine, phenylalanine, tyrosine or tryptophan. Any mutant Msp monomer sequence described herein can further comprise a D90N, a D91N and a D93N mutation. For example, provided herein is a nucleic acid sequence encoding a mutant single-chain Msp, wherein the nucleic acid sequence comprises (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence, wherein the first Msp monomer sequence is a mutant Msp monomer sequence that comprises a mutation at position P97 can further comprise (i) a mutation at amino acid position D118, D134 and/or E139 (ii) a mutation at position D93, and/or (iii) a mutation at position D90, position D91 or both positions D90 and D91. For example, the first Msp monomer sequence can be a mutant Msp monomer sequence that comprises a D90N mutation, a D91N mutation, a D93N mutation, a P97F mutation, a D118R mutation, a D134R mutation and a E139K mutation.

Further provided is a nucleic acid sequence encoding a mutant single-chain Msp, wherein the nucleic acid sequence comprises (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence, wherein the first Msp monomer sequence is a mutant Msp monomer sequence that comprises one or more mutations at any of the following amino acid positions: I68, S73, S116, P123 or V128.

The first Msp monomer sequence can also be a mutant Msp monomer sequence that comprises one or more mutations at any of the following amino acid positions: I68, S73, S116, P123 or V128 and further comprises a mutation at amino acid position D118, optionally with (i) a mutation at position 93, and/or (ii) a mutation at position D90, position D91 or both positions D90 and D91. In any of the mutant Msp monomer sequences described herein, the amino acid at position 91 or the amino acid at position 90 can be substituted with arginine, lysine, histidine, glutamine, methionine, threonine, phenylalanine, tyrosine or tryptophan. The mutant Msp monomer sequence can further comprise a D90N, a D91N and a D93N mutation. The mutant Msp monomer comprising one or more mutations at amino acids I68, S73, S116, P123 or V128 can further comprise a mutation in one or more of the amino acids at positions D13, A55, D56, E57, F58, E63, S136, D134, G137, E139 or D172. In the mutant Msp monomer sequences described herein, D13, A55, D56, E57, F58, E63, S136, D134, G137, E139 or D172 can be substituted with lysine or arginine. Therefore, a mutant Msp monomer comprising one or more mutations at amino acids I68, S73, S116, P123 or V128, for example, can further comprise (i) a mutation at amino acid position D118, (ii) a mutation at position D93, (iii) a mutation at position D90, position D91 or both positions D90 and D91, (iv) a D90N, a D91N and a D93N mutation and/or (v) a mutation in one or more of the amino acids at positions D13, A55, D56, E57, F58, E63, S136, D134, G137, E139 or D172.

For example, and not to be limiting, a first mutant Msp monomer can be a mutant Msp monomer comprising a mutation at positions D56, I68, S73, D118, D134 and E139. Optionally, the mutant Msp monomer can further comprise a D90N, a D91N and D93N mutation. Optionally, one or more of the amino acids selected from the group consisting of D56, I68, S73, D118, D134 and E139 can be substituted with lysine or arginine.

Further provided is a nucleic acid sequence encoding a mutant single-chain Msp, wherein the nucleic acid sequence comprises: (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence, wherein the first Msp monomer sequence is a mutant Msp monomer sequence that comprises one or more mutations at any of the following amino acid positions: I68, S73, S116, P123 or V128; and wherein one or more of the first, second, third, fourth, fifth, sixth, seventh, and eighth nucleotide sequence encodes a mutant Msp monomer sequence comprising a mutation at one or more of the following positions: T83, N86, L88, I105, D90, D91, G92, D93 or A96. For example, and not to be limiting, the seventh nucleotide can encode a mutant Msp monomer sequence comprising a mutation at one or more of the following positions: T83, N86, L88, I105, D90, D91, G92, D93 or A96.

It is understood that the first nucleotide sequence and the seventh nucleotide sequence can be arranged, but are not necessarily arranged as the first nucleotide sequence and the seventh nucleotide sequence in the nucleic acid sequence that comprises a first, second, third, fourth, fifth, sixth, seventh, and eighth nucleotide sequence in that order. In this context, the first nucleotide sequence is a nucleotide sequence encoding the first or starting monomer of a single-chain Msp, and can be the first, second, third, fourth, fifth, sixth, seventh, or eighth nucleotide sequence of the single-chain Msp. The starting nucleotide sequence is referred to as the first nucleotide sequence no matter where it occurs in the single-chain Msp. For example, if the starting subunit of the single-chain Msp is the first Msp monomer (first nucleotide sequence), then the seventh Msp monomer (seventh nucleotide sequence) comprises a mutation at one or more of the following positions: T83, N86, L88, I105, D90, D91, G92, D93 or A96. In another example, if the starting subunit of the single-chain Msp is the second Msp monomer (first nucleotide sequence), then the eighth Msp monomer (seventh nucleotide sequence) comprises a mutation at one or more of the following positions: T83, N86, L88, I105, D90, D91, G92, D93 or A96. In another example, if the starting subunit of the single-chain Msp is the third Msp monomer (first nucleotide sequence), then the first Msp monomer (seventh nucleotide sequence) comprises a mutation at one or more of the following positions: T83, N86, L88, I105, D90, D91, G92, D93 or A96. In another example, if the starting subunit of the single-chain Msp is the fourth Msp monomer (first nucleotide sequence), then the second Msp monomer (seventh nucleotide sequence) comprises a mutation at one or more of the following positions: T83, N86, L88, I105, D90, D91, G92, D93 or A96. In another example, if the starting subunit of the single-chain Msp is the fifth Msp monomer (first nucleotide sequence), then the third Msp monomer (seventh nucleotide sequence) comprises a mutation at one or more of the following positions: T83, N86, L88, I105, D90, D91, G92, D93 or A96. In another example, if the starting subunit of the single-chain Msp is the sixth Msp monomer (first nucleotide sequence), then the fourth Msp monomer (seventh nucleotide sequence) comprises a mutation at one or more of the following positions: T83, N86, L88, I105, D90, D91, G92, D93 or A96. In another example, if the starting subunit of the single-chain Msp is the seventh Msp monomer (first nucleotide sequence), then the fifth Msp monomer (seventh nucleotide sequence) comprises a mutation at one or more of the following positions: T83, N86, L88, I105, D90, D91, G92, D93 or A96. In another example, if the starting subunit of the single-chain Msp is the eighth Msp monomer (first nucleotide sequence), then the sixth Msp monomer (seventh nucleotide sequence) comprises a mutation at one or more of the following positions: T83, N86, L88, I105, D90, D91, G92, D93 or A96.

For example, and not to be limiting, the first Msp monomer can be a mutant Msp monomer that comprises a mutation at positions D56, I68, S73, D118, D134 and E139 and the seventh monomer can be a mutant Msp monomer that comprises a mutation at positions L88 and I105. Optionally, each of the amino acid positions at positions D56, I68, S73, D118, D134 and E139 of the first mutant Msp monomer can be substituted with lysine or arginine. Optionally, each of the amino acid positions at positions D56, I68, S73, D118, D134 and E139 of the first mutant Msp monomer can be substituted with phenylalanine, tryptophan, histidine or tyrosine. Optionally, each of the amino acid positions at positions L88 and I105 of the seventh mutant Msp monomer can be substituted with lysine or arginine. Optionally, each of the amino acid positions at positions L88 and I105 of the seventh mutant Msp monomer can be substituted with phenylalanine, tryptophan, histidine or tyrosine. Substitution of D56, I68, S73, D118, D134, E139, L88 and/or I105 with aromatic amino acids, such as, phenylalanine, tryptophan, histidine or tyrosine can promote p-stacking interactions with an analyte, for example, nucleotides, to decrease translocation velocity. Optionally, the first, second, third, fourth, fifth, sixth, seventh, and eighth Msp monomer sequence, or a subset thereof can comprise a D90N, a D91N and a D93N mutation.

FIGS. 10A and 10B show a non-limiting example of a positive ramp created in a single-chain Msp comprising a first mutant Msp monomer that comprises a mutation at positions D56, I68, S73, D118, D134 and E139 and a seventh mutant Msp monomer that comprises a mutation at positions L88 and I105. This positively charged ramp inside the vestibule of the MspA guides single-stranded nucleic acids, for example DNA, through the Msp. The electrostatic interactions between the nucleic acid and the ramp enable controlled translocation of DNA through the pore. This reduces Brownian motion of the nucleic acid and the translocation rate. This also increases the precision and the interaction between the nucleic acid bases and the amino acids in the constriction zone. FIG. 10C is a schematic of a single-chain Msp. Numbers under subunits #1 and #7 represent locations of the positive ramp.

In any of the mutant single-chain Msps set forth herein, the constriction zone can be modified to increase the nucleobase, protein or analyte recognition properties of MspA. Modifications to the constriction zone can create a reading head that increases, for example, base-specific interactions. A reading head can be created by introducing an amino acid with a longer side chain that protrudes into the path of DNA or another analyte. For example, and not to be limiting, in order to create one or more reading heads, the amino acid at position 90 and/or 91 in any of the mutant Msp monomers of the single-chain Msps described herein can be substituted with arginine, lysine, histidine, glutamine, methionine, threonine, phenylalanine, tyrosine, tryptophan or an unnatural amino acid. Positioning heads can also be created to increase the efficiency of one or more reading heads. For example, amino acids with longer side chains, preferably hydrophobic or negatively charged, can be introduced, opposite to the reading head, in order to reduce escape motions of DNA or another analyte in the constriction zone. Amino acids that are suitable, include but are not limited to, aspartate, glutamate, valine, leucine, isoleucine, phenylalanine, tyrosine, tryptophan and unnatural amino acids. In order to further slow down translocation rates, a stacking slide can be created by mutating one or more of the amino acids at positions 83, 86, 88 and 105. For example, and not to be limiting, one or more of the amino acids at positions 83, 86, 88 and 105 can be substituted with tryptophan, tyrosine or phenylalanine. Optionally, the stacking slide is positioned such that it is located in proximity to a positive ramp.

One or more of the second, third, fourth, fifth, sixth, seventh, and eighth Msp monomer sequence or any subset thereof, can be independently selected from the group consisting of a wildtype MspA monomer, a mutant MspA monomer, a wild-type MspA paralog or homolog monomer, and a mutant MspA paralog or homolog monomer. It is understood that, when the second, third, fourth, fifth, sixth, seventh and/or eight Msp monomer sequence is a mutant MspA monomer sequence, the mutant MspA monomer sequence can be the same or different than the first mutant MspA monomer sequence. Optionally, the second, third, fourth, fifth, sixth, seventh, and eighth Msp monomer sequence, or any subset thereof, is a wild-type MspA paralog or homolog monomer. These include, but are not limited to, MspA/Msmeg0965, MspB/Msmeg0520, MspC/Msmeg5483, MspD/Msmeg6057, MppA, PorM1, PorM2, PorM1, Mmcs4296, Mmcs4297, Mmcs3857, Mmcs4382, Mmcs4383, Mjls3843, Mjls3857, Mjls3931 Mjls4674, Mjls4675, Mjls4677, Map3123c, Mav3943, Mvan1836, Mvan4117, Mvan4839, Mvan4840, Mvan5016, Mvan5017, Mvan5768, MUL_2391, Mflv1734, Mflv1735, Mflv2295, Mflv1891, MCH4691c, MCH4689c, MCH4690c, MAB1080, MAB1081, MAB2800, RHA1 ro08561, RHAI ro04074, and RHA1 ro03127. A wild-type MspA paralog or homolog monomer may be a wild-type MspB monomer.

Mutant Msp Monomers and the Nucleic Acids Encoding Them

Further provided is a nucleic acid encoding a mutant Msp monomer, wherein the Msp monomer comprises a mutation at position 97. Optionally, the mutant Msp monomer can comprise a mutation at P97, wherein the mutation is not a P97S mutation or a P97C mutation. Optionally, the mutant Msp monomer can comprise a P97F mutation. Optionally the mutant Msp monomer can further comprise a mutation at amino acid position D118, a mutation at position D134 or a mutation at position E139. For example, the mutant Msp monomer comprising a mutation at position 97 can further comprise a D118R mutation, a D134R mutation and/or a E139K mutation. Optionally, the mutant Msp monomer comprising a mutation at position 97 can further comprise (i) a mutation at position 93 and/or (ii) a mutation at position D90, position D91 or both positions D90 and D91. Optionally, the amino acid at position 90 or 91 is substituted with arginine, lysine, histidine, glutamine, methionine, threonine, phenylalanine, tyrosine or tryptophan. Optionally, the mutant Msp monomer can further comprise a D90N, a D91N and a D93N mutation. For example, and not to be limiting, a mutant MspA monomer sequence can comprise a D90N mutation, a D91N mutation, a D93N mutation, a P97F mutation, a D118R mutation, a D134R mutation and a E139K mutation.

Further provided is a nucleic acid encoding a mutant Msp monomer, wherein the Msp monomer comprises a mutation at one or more of the following positions: I68, S73, S116, P123 or V128. Optionally, the mutant monomer further comprises a mutation at amino acid position D118. Optionally, the Msp monomer further comprises a mutation at position D90, position D91 or both positions D90 and D91. Optionally, the amino acid at position 91 or the amino acid at position 90 can be substituted with arginine, lysine, histidine, glutamine, methionine, threonine, phenylalanine, tyrosine or tryptophan. Optionally, the mutant Msp monomer sequence can further comprise a D90N, a D91N and a D93N mutation. Optionally, the mutant Msp monomer sequence can further comprise a mutation in one or more of the amino acids at positions D13, A55, D56, E57, F58, E63, S136, D134, G137, E139 or D172. Optionally, one or more of D13, A55, D56, E57, F58, E63, S136, D134, G137, E139 or D172 can be substituted with lysine or arginine.

Further provided is a nucleic acid encoding a mutant Msp monomer, wherein the Msp monomer comprises a mutation at one or more of the following positions: T83, N86, G92 or A96. Optionally, the mutant Msp monomer sequence further comprises a mutation at position L88 or I105. Optionally, the mutant monomer further comprises a mutation at amino acid positions D118. Optionally, the Msp monomer further comprises a mutation at position D90, position D91 or both positions D90 and D91. Optionally, the amino acid at position 91 or the amino acid at position 90 can be substituted with arginine, lysine, histidine, glutamine, methionine, threonine, phenylalanine, tyrosine or tryptophan. Optionally, the mutant Msp monomer sequence can further comprise a D90N, a D91N and a D93N mutation.

As used herein, a mutant Msp monomer refers to an Msp monomer that has at least or at most 70, 75, 80, 85, 90, 95, 98, or 99 percent or more identity, or any range derivable therein, but less than 100% identity, as compared to a wild-type Msp monomer, and retains tunnel-forming capability when associated with one or more other Msp monomers (wild-type or mutant). Therefore, in addition to the mutations described herein, any mutant Msp provided herein can further comprise additional modifications such as substitutions, insertions, deletions, and/or additions, as long as the mutant Msp monomer has at least or at most 70, 75, 80, 85, 90, 95, 98, or 99 percent or more identity, or any range derivable therein, but less than 100%, to a wild-type Msp monomer, and retains tunnel-forming capability when associated with one or more other Msp monomers.

Any mutant Msp described herein can comprise 2-15 Msp monomers that are the same or different, wherein at least one of the Msp monomers is a mutant Msp monomer. Optionally, a mutant Msp comprises 7-9 Msp monomers that are the same or different. Optionally, at least a second monomer is selected from the group consisting of a wildtype Msp monomer, a second mutant Msp monomer, a wild-type Msp paralog or homolog monomer, and a mutant Msp paralog or homolog monomer, wherein the second mutant Msp monomer may be the same or different than the first mutant Msp monomer. For example, any mutant Msp described herein can comprise 2-15 Msp monomers wherein at least one of the Msp monomers is a mutant MspA monomer. Optionally, at least a second monomer is selected from the group consisting of a wildtype MspA monomer, a second mutant MspA monomer, a wild-type MspA paralog or homolog monomer, and a mutant MspA paralog or homolog monomer, wherein the second mutant MspA monomer can be the same or different than the first mutant MspA monomer. Optionally, the second monomer is a wild-type MspA paralog or homolog monomer.

For example, a mutant Msp can comprise one or more Msp monomers comprising a mutation at position 97. In another example, a mutant Msp can comprise one or more Msp monomers comprising a mutation at one or more of I68, S73, S116, P123 or V128 and one or more Msp monomers comprising a mutation at one or more of the following positions: T83, N86, L88, I105, D90, D91, G92, D93 or A96. In another example, a mutant Msp can comprise one or more Msp monomers with mutations at positions D56, I68, S73, D118, D134 and E139 and one or more Msp monomers with mutations at positions L88 and I105.

Modifications in amino acid sequence may arise as allelic variations (e.g., due to genetic polymorphism), may arise due to environmental influence (e.g., due to exposure to ultraviolet radiation), or other human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to about 6 residues are deleted at any one site within the protein molecule. Amino acid substitutions are typically of single residues, but can occur at a number of different locations at once; insertions usually will be on the order of about from 1 to about 10 amino acid residues; and deletions will range from about 1 to about 30 residues. Deletions or insertions preferably are made in adjacent pairs, i.e., a deletion of 2 residues or insertion of 2 residues. Substitutions, deletions, insertions or any combination thereof can be combined to arrive at a final construct. The mutations may or may not place the sequence out of reading frame and may or may not create complementary regions that could produce secondary mRNA structure. Substitutional modifications are those in which at least one residue has been removed and a different residue inserted in its place.

Modifications, including the specific amino acid substitutions disclosed herein, are made by known methods. By way of example, modifications are made by site specific mutagenesis of nucleotides in the DNA encoding the protein, thereby producing a DNA encoding the modification, and thereafter expressing the DNA in recombinant cell culture to produce the Msp monomers or single chain multimers. Techniques for making substitution mutations at predetermined sites in DNA having a known sequence are well known, for example M13 primer mutagenesis and PCR mutagenesis.

The amino acids in the Msp proteins described herein can be any of the 20 naturally occurring amino acids, D-stereoisomers of the naturally occurring amino acids, unnatural amino acids and chemically modified amino acids. Unnatural amino acids (that is, those that are not naturally found in proteins) are also known in the art, as set forth in, for example, Williams et al., Mol. Cell. Biol. 9:2574 (1989); Evans et al., J. Amer. Chem. Soc. 112:4011-4030 (1990); Pu et al., J. Amer. Chem. Soc. 56:1280-1283 (1991); Williams et al., J. Amer. Chem. Soc. 113:9276-9286 (1991); and all references cited therein. B and y amino acids are known in the art and are also contemplated herein as unnatural amino acids.

As used herein, a chemically modified amino acid refers to an amino acid whose side chain has been chemically modified. For example, a side chain can be modified to comprise a signaling moiety, such as a fluorophore or a radiolabel. A side chain can also be modified to comprise a new functional group, such as a thiol, carboxylic acid, or amino group. Post-translationally modified amino acids are also included in the definition of chemically modified amino acids.

Also contemplated are conservative amino acid substitutions. By way of example, conservative amino acid substitutions can be made in one or more of the amino acid residues of any Msp monomer provided herein. One of skill in the art would know that a conservative substitution is the replacement of one amino acid residue with another that is biologically and/or chemically similar. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Nonconservative substitutions, for example, substituting a proline with glycine are also contemplated.

Those of skill in the art readily understand how to determine the identity of two polypeptides or nucleic acids. For example, the identity can be calculated after aligning the two sequences so that the identity is at its highest level. Another way of calculating identity can be performed by published algorithms. Optimal alignment of sequences for comparison can be conducted using the algorithm of Smith and Waterman, *Adv. Appl. Math.* 2: 482 (1981); by the alignment algorithm of Needleman and Wunsch, *J. Mol. Biol.* 48: 443 (1970); by the search for similarity method of Pearson and Lipman, *Proc. Natl. Acad. Sci. U.S.A.* 85: 2444 (1988); by computerized implementations of these algorithms (GAP, BESTFIT, FASTA, and TFASTA in the Wisconsin Genetics Software Package, Genetics Computer Group, 575 Science Dr., Madison, WI; the BLAST algorithm of Tatusova and Madden FEMS Microbiol. Lett. 174: 247-250 (1999) available from the National Center for Biotechnology Information (http://www.ncbi.nlm.nih.gov/blast/bl2seq/bl2. html); or by inspection.

The same types of identity can be obtained for nucleic acids by, for example, the algorithms disclosed in Zuker, *Science* 244:48-52, 1989; Jaeger et al. *Proc. Natl. Acad. Sci. USA* 86:7706-7710, 1989; Jaeger et al. *Methods Enzymol.* 183:281-306, 1989 that are herein incorporated by this reference for at least material related to nucleic acid alignment. It is understood that any of the methods typically can be used and that, in certain instances, the results of these various methods may differ, but the skilled artisan understands if identity is found with at least one of these methods, the sequences would be said to have the stated identity.

For example, as used herein, a sequence recited as having a particular percent identity to another sequence refers to sequences that have the recited identity as calculated by any one or more of the calculation methods described above. For example, a first sequence has 80 percent identity, as defined herein, to a second sequence if the first sequence is calculated to have 80 percent identity to the second sequence using the Zuker calculation method even if the first sequence does not have 80 percent identity to the second sequence as calculated by any of the other calculation methods. As yet another example, a first sequence has 80 percent identity, as defined herein, to a second sequence if the first sequence is calculated to have 80 percent identity to the second sequence using each of calculation methods (although, in practice, the different calculation methods will often result in different calculated identity percentages).

Further, any Msp or Msp monomer can also be chemically or biologically modified. For example, one can modify an Msp or Msp monomer with chemicals to produce disulfide bridges, as is known by those of skill in the art.

An Msp can comprise a nucleotide binding site. As used herein, a nucleotide binding site refers to a site in an Msp where a nucleotide stays in contact with, or resides at, an amino acid for a period of time that is longer than attributable to diffusion movement, such as greater than one picosecond or one nanosecond. Molecular dynamics calculations can be employed to assess these temporary resting times.

Polypeptides encoded by nucleic acids described herein are also provided. Therefore polypeptides comprising a mutant Msp monomer or functional fragment thereof, are provided. Non-limiting examples of mutant Msp monomers include but are not limited to, polypeptides comprising SEQ ID NO: 1, SEQ ID NO: 2, SEQ ID NO: 3 and SEQ ID NO: 4 comprising any of the mutations described herein. Further provided is a Msp monomer comprising an amino acid sequence that has least 50%, 55%, 60%, 65%, 70%, 75%, 80%, 85%, 90%, 95%, 99% identity or any percentage in between to a polypeptide comprising SEQ ID NO: 1, SEQ ID NO: 2, SEQ ID NO: 3 and SEQ ID NO: 4, wherein the polypeptide comprises any of the mutations described herein. Also provided are polypeptides comprising a mutant single-chain Msp or functional fragment thereof. Also provided are polypeptides comprising a mutant single-chain Msp comprising any of the mutant Msp monomers described herein, or a fragment thereof.

Non-limiting examples of mutant Msp monomers comprising mutations set forth herein are provided in Table 2. Each exemplary mutant Msp monomer comprises all of the mutations listed for each monomer. For example, D90N/D91N/D93N/P97F indicates that all four mutations are present. Single chain Msps comprising any of the exemplary mutant Msp monomer sequences provided in Table 2 are also provided herein. It is understood that amino acids listed in parentheses are listed as alternatives for subsitutions at that position. For example, P97 (A/V/L/IF/M/Y/W or G) means that P97 can be substituted with A, V, L, I, F, M, Y W or G.

TABLE 2

D90N/D91N/D93N/P97(A/V/L/I/F/M/Y/W or G)
D90N/D91N/D93N/P97F/D118R/D134R/E139K
D90N/D91N/D93N/P97F
D90N/D91N/D93N/G92(A/V/L/I/P/F/M/Y or W)
D90N/D91N/D93N/I94(A/V/L/P/F/M/Y/W or G)
D90N/D91N/D93N/T95(A/V/L/P/F/M/Y/W or G)
D90N/D91N/D93N/A96(V/L/P/F/I/M/Y/W or G)
D90N/D91N/D93N/P98(A/V/L/F/I/M/Y/W or G)
D90N/D91N/D93N/F99(A/V/L/P/I/M/Y/W or G)
D90N/D91N/D93N/G100(A/V/L/P/F/I/M/Y or W)
D90N/D91N/D93N/L101(A/V/I/F/M/Y/W or G)
D90N/D91N/D93N/N102((AN/L/I/P/F/M/Y/W or G)
D90N/D91N/D93N/S103((A/V/L/I/P/F/M/Y/W or G)
D90N/G92F/D91N/D93N/P97F
D90N/T95F/D91N/D93N/P97F
D90N/A96F/D91N/D93N/P97F
D90N/A96F/D91N/D93N/P97F/P98F
D90N/G92F/D91N/D93N/P97F/D118R/D134R/E139K
I68(R/K/F/W/Y or H)/D90N/D91N/D93N
I68(R/K/F/W/Y or H)/D90N/D91N/D93N/D118R/D134R/E139K
I68(K/R/F/W/Y or H)/D90N/D91N/D93N
I68(K/R/F/W/Y or H)/D90N/D91N/D93N/D118R/D134R/E139K
S73 (K/R/F/W/Y or H)/D90N/D91N/D93N
S73 (K/R/F/W/Y or H)/D90N/D91N/D93N/D118R/D134R/E139K
S73 (K/R/F/W/Y or H)/D90N/D91N/D93N
S73 (K/R/F/W/Y or H)/D90N/D91N/D93N/D118R/D134R/E139K
D90N/D91N/D93N/S116R
D90N/D91N/D93N/S116R/D118R/D134R/E139K
D90N/D91N/D93N/S116K
D90N/D91N/D93N/S116K/D118R/D134R/E139K
D90N/D91N/D93N/P123R
D90N/D91N/D93N/P123R/D118R/D134R/E139K
D90N/D91N/D93N/P123K
D90N/D91N/D93N/P123K/D118R/D134R/E139K
D90N/D91N/D93N/L88(K/R/F/W/H or Y)
D90N/D91N/D93N/I105(K/R/F/W/H or Y)
D90N/D91N/D93N/L88(K/R/F/W/H or Y)/D118R/D134R/E139K
D90N/D91N/D93N/I105(K/R/F/W/H or Y)/D118R/D134R/E139K
D90N/D91N/D93N/L88(K/R/F/W/H or Y)/I105(K/R/F/W/H or Y)
D90N/D91N/D93N/L88(K/R/F/W/H or Y)/I105(K/R/F/W/H or Y)/D118R/D134R/E139K
D90N/D91N/D93N/L88(K/R/F/W/H or Y)
D90N/D91N/D93N/T83(K/R/F/W/H or Y)/D118R/D134R/E139K
D90N/D91N/D93N/T83(K/R/F/W/H or Y)
D90N/D91N/D93N/N86(K/R/F/W/H or Y)
D90N/D91N/D93N/N86(K/R/F/W/H or Y)/D118R/D134R/E139K

Tunnel-Forming Proteins

Methods of determining whether a protein is a tunnel-forming protein are well known in the art. One can determine if an Msp forms a tunnel by determining whether the protein inserts into a bilayer, such as described in Example 2 of U.S. Patent Publication No. 20120055792, incorporated herein in its entirety by this reference. All of the methods of making and using porins described in U.S. Patent Publication No. 20120055792 can be employed to make and use the Msp porins described herein. If the protein inserts into the bilayer, then the porin is a tunnel-forming protein. Typically, tunnel formation is detected by observing a discrete change in conductivity. See, U.S. Patent Publication No. 20120055792, and Niederweis et al., *Mol. Microbiol.* 33:933 (1999), both of which are incorporated herein by reference.

Bilayers are described herein. An Msp will typically be able to be inserted in a lipid bilayer or other thin film, which are each well-known in the art. An example of inserting a mutant MspA into a lipid bilayer is provided in U.S. Patent Publication No. 20120055792; this technique can be applied to other Msp proteins as well. In addition, U.S. Pat. No. 6,746,594, incorporated herein by reference, describes a variety of lipid bilayers and thin films, including inorganic materials, that can be employed with respect to the Msps discussed herein. Methods, apparatuses, and techniques described in U.S. Pat. No. 6,267,872, incorporated herein by reference in its entirety, are also employable with respect to Msps discussed herein. Moreover, more than one Msp can be comprised in a lipid bilayer. For example, 2 3, 4, 5, 10, 20, 200, 2000, or more can be comprised in a lipid bilayer. Optionally, anywhere from 2 to $10^{10}$ Msps can be employed in methods described herein. Such a plurality of Msps can be in the form of clusters of Msps. Clusters can be randomly assembled or can adopt a pattern. As used herein, a cluster refers to molecules that are grouped together and move as a unit, but are not covalently bound to one another.

Optionally, Msps do not gate spontaneously. As used herein, to gate or gating refers to the spontaneous change of electrical conductance through the tunnel of the protein that is usually temporary (e.g., lasting for as few as 1-10 milliseconds to up to a second). Long lasting gating events can often be reversed by changing the polarity. Under most circumstances, the probability of gating increases with the application of higher voltages. Gating and the degree of conductance through the tunnel change are highly variable among Msps, depending on, for example, the make-up of the vestibule and constriction zone as well as the properties of the liquid medium in which the protein is submerged. Typically, the protein becomes less conductive during gating, and conductance can permanently stop (i.e., the tunnel may permanently shut) as a result, such that the process is irreversible. Optionally, gating refers to the conductance through the tunnel of a protein spontaneously changing to less than 75% of its open state current.

Various conditions such as light and liquid medium, including its pH, buffer composition, detergent composition, and temperature, can affect the behavior of an Msp, particularly with respect to its conductance through the tunnel as well as the movement of an analyte with respect to the tunnel, either temporarily or permanently.

As used throughout, a tunnel refers to the central, empty portion of an Msp that is defined by the vestibule and the constriction zone, through which a gas, liquid, ion, or analyte can pass. As used herein, "cis" refers to the side of an Msp tunnel through which an analyte enters the tunnel or across the face of which the analyte moves. As used herein, "trans" refers to the side of an Msp tunnel through which an analyte (or fragments thereof) exits the tunnel or across the face of which the analyte does not move.

Any mutant Msp described herein, for example a mutant MspA, can comprise a vestibule and a constriction zone that define a tunnel. Further, the diameter of a mutant Msp or mutant Msp paralog or homolog can be less than the diameter of the constriction zone of a corresponding wild-type Msp or wild-type Msp paralog or homolog. A mutant Msp or mutant Msp paralog or homolog can have a mutation in the vestibule or the constriction zone that permits an analyte to translocate, electrophoretically or otherwise, through the tunnel of the mutant Msp or mutant Msp paralog or homolog with a translocation velocity or an average translocation velocity that is less than the translocation velocity or average translocation velocity at which the analyte translocates through the tunnel of a wild-type Msp or wild-type Msp paralog or homolog. Also, any mutant Msp described herein can comprise a vestibule having a length from about 2 to about 6 nm and a diameter from about 2 to about 6 nm, and a constriction zone 5 having a length from about 0.3 to about 3 nm and a diameter from about 0.3 to about 3 nm, wherein the vestibule and constriction zone together define a tunnel. It is understood that, one or more mutations, can be made in the vestibule or the constriction zone of any of the Msp described herein in order to increase or decrease conductance through the tunnel of an Msp. For example, any of the mutant Msps described herein can further comprise a deletion, substitution or insertion of an amino acid in the vestibule and/or the constriction zone in order to modify conductance.

As used throughout, a vestibule refers to the cone-shaped portion of the interior of an Msp whose diameter generally decreases from one end to the other along a central axis, where the narrowest portion of the vestibule is connected to the constriction zone. A vestibule can also be referred to as a goblet. The vestibule and the constriction zone together define the tunnel of an Msp. When referring to a diameter of the vestibule, it is understood that because the vestibule is cone-like in shape, the diameter changes along the path of a central axis, where the diameter is larger at one end than the opposite end. The diameter can range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis can range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to diameter herein, one can determine a diameter by measuring center-to-center distances or atomic surface-to-surface distances.

As used throughout, a constriction zone refers to the narrowest portion of the tunnel of an Msp, in terms of diameter, that is connected to the vestibule. The length of the constriction zone can range from about 0.3 nm to about 2 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone can range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein.

Any Msp discussed herein can be comprised in a lipid bilayer. Optionally, an analyte electrophoretically or otherwise translocates from the cis side through a tunnel to the trans side. Optionally, an analyte electrophoretically or otherwise translocates from the trans side through a tunnel to the cis side. Optionally, an analyte is electrophoretically or otherwise driven from the cis side or the trans side into a tunnel and stays in the tunnel or then retracts to the cis side or the trans side, respectively. It is understood that analytes can translocate through the tunnel in the presence or absence of an electric field.

Single-chain Msps function at a wide range of electrolyte concentration, for example from about 0.3-1M KCl (see FIG. 22). To optimize channel activity, lipid association can be performed prior to insertion of Msp in a membrane or lipid bilayer. In a non-limiting example, FIG. 22 shows that no channel activity was observed in a buffer containing only 0.3 M KCl at pH 8.0. However, breaking the membrane and subsequent repainting of the membrane leads to increased channel activity of scMspA PN1 in the electrolyte containing 0.3 M KCl at pH 8.0. Therefore, in any of the methods set forth herein, an Msp can be contacted or preincubated with one or more lipids to optimize channel activity.

Vectors and Cells

A vector comprising a nucleic acid encoding a polypeptide described herein is also provided. The vector can further comprise a promoter sequence, for example, a constitutive promoter or an inducible promoter. Examples of constitutive promoter include, but are not limited to, the psmyc promoter and Phsp60. Examples of inducible promoters include, but are not limited to, an acetamide-inducible promoter and a tetracycline inducible promoter.

Cultured cells transfected with any vector described herein, or progeny thereof, wherein the cell is capable of expressing a Msp (either as a single-chain Msp, an Msp comprising Msp monomers or an Msp monomer, are also provided). A *Mycobacterium smegmatis* strain comprising any vector described herein is also provided. A *Mycobacterium smegmatis* strain free of endogenous porins is also contemplated and can further comprise any vector described herein. By "free" is meant that an endogenous porin cannot be detected in an immunoblot when using an appropriate Msp-specific antiserum, or comprising less than 1% endogenous porins.

Any of the Msp monomers or single-chain Msps disclosed herein can be produced by transforming a mutant bacterial strain comprising a deletion of a wild-type MspA, a wild-type MspB, a wild-type MspC, a wildtype MspD, with a vector comprising an inducible promoter operably linked to a nucleic acid sequence encoding the Msp monomer or single-chain Msp porin; and purifying the Msp monomer or single-chain Msp porin (See, for example, U.S. Pat. No. 6,746,594 incorporated herein by reference). Optionally, the mutant bacterial strain comprises a deletion of a recA gene. Optionally, the vector comprises any of the nucleic acids encoding an Msp monomer or single-chain Msp described herein. The bacterial strain can further comprise *M. smegmatis* strain ML16, ML714 or ML712.

Systems and Methods of Use

Also provided is a system comprising a mutant Msp described herein having a vestibule and a constriction zone that define a tunnel, wherein the tunnel is positioned between a first liquid medium and a second liquid medium, wherein at least one liquid medium comprises an analyte, and wherein the system is operative to detect a property of the analyte. A system can be operative to detect a property of any analyte comprising subjecting an Msp to an electric field such that the analyte interacts with the Msp. A system can be operative to detect a property of the analyte comprising subjecting the Msp to an electric field such that the analyte electrophoretically translocates through the tunnel of the Msp. Also provided is a system comprising an Msp having a vestibule and a constriction zone that define a tunnel, wherein the tunnel is positioned in a lipid bilayer between a first liquid medium and a second liquid medium, and wherein the only point of liquid communication between the first and second liquid media occurs in the tunnel. Moreover, any system described herein can comprise any mutant Msp described herein.

The first and second liquid media can be the same or different, and either one or both can comprise one or more salts, detergents, or buffers. In fact, any liquid media described herein can comprise one or more of a salt, a detergent, or a buffer. Optionally, at least one liquid medium is conductive. Optionally, at least one liquid medium is not conductive. Any liquid medium described herein can comprise a viscosity-altering substance or a velocity-altering substance. The liquid medium can comprise any analyte described herein.

A property of an analyte can be an electrical, chemical, or physical property. An Msp can be comprised in a lipid bilayer in a system or any other embodiment described herein. A system can comprise a plurality of Msps. A system can comprise any Msp described herein, such as a single-chain mutant MspA or a mutant Msp comprising at least 2-15 monomers, wherein at least one of the monomers is a mutant MspA monomer. A mutant Msp comprised in a system can comprise a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel.

Any Msp described herein, including an Msp comprised in a system, can further comprise a molecular motor. The molecular motor in a system is capable of moving an analyte into or through a tunnel with a translocation velocity or an average translocation velocity that is less than the translocation velocity or average translocation velocity at which the analyte translocates into or through the tunnel in the absence of the molecular motor. The molecular motor can be, for example, an enzyme, such as a polymerase, an exonuclease, or a helicase such as DnaB or a phage nucleic acid packing motors (see, for example, *Serwer Viruses* 3(7): 1249-80 (2011)). Any system described herein can further comprise a patch-clamp amplifier or a data acquisition device. A system can further comprise one or more temperature regulating devices in communication with the first liquid medium, the second liquid medium, or both. Any system described herein can be operative to translocate an analyte through an Msp tunnel either electrophoretically or otherwise.

The mutant MspA can have a mutation in the vestibule or the constriction zone that permits an analyte to translocate, e.g., electrophoretically, through the tunnel with an average translocation velocity of less than 0.5 nm/µs or less than 0.05 nm/µs. The analyte can be selected from the group consisting of a nucleotide(s), a nucleic acid, amino acid(s), a peptide, a protein, a polymer, a drug, an ion, a biological warfare agent, a pollutant, a nanoscopic object, or a combination or cluster thereof. Optionally, the analyte is further defined as a nucleic acid. The nucleic acid can translocate, electrophoretically or otherwise, through the tunnel with an average translocation velocity of less than 1 nucleotide/µs, or less than 0.1 nucleotide/µs. A nucleic acid can be further defined as ssDNA, dsDNA, RNA, or a combination thereof.

As used herein, electrophoretically translocating an analyte, refers to applying an electric field to an Msp porin that is in contact with one or more solutions (e.g., immersed in a solution), such that current flows through the Msp tunnel. The electric field moves an analyte such that it interacts with the tunnel. As used herein, "interacts" means that the analyte moves into and, optionally, through the tunnel, where "through the Msp tunnel" (or "translocates") means to enter one side of the tunnel and move to and out of the other side of the tunnel. It is specifically contemplated that any analyte discussed herein can translocate through an Msp tunnel, either electrophoretically or otherwise, in any embodiment discussed herein. In this regard, it is specifically contemplated that any embodiment herein comprising translocation can refer to electrophoretic translocation or nonelectrophoretic translocation, unless specifically noted. Optionally, methods that do not employ electrophoretic translocation are contemplated.

As used throughout, a liquid medium includes aqueous, organic-aqueous, and organic-only liquid media. Organic media include, e.g., methanol, ethanol, dimethylsulfoxide, and mixtures thereof. Liquids employable in methods described herein are well-known in the art. Descriptions and examples of such media, including conductive liquid media, are provided in U.S. Pat. No. 7,189,503, for example, which is incorporated herein by reference in its entirety. Salts, detergents, or buffers may be added to such media. Such agents can be employed to alter pH or ionic strength of the liquid medium. Viscosity-altering substances, such as glycerol or various polymers (e.g., polyvinylpyrrolidone, polyethylene glycol, polyvinyl alcohol, cellulose polymers), and mixtures thereof, can be included in liquid media. Methods of measuring viscosity are well-known in the art.

Any agent that can be added to a liquid medium can also alter the velocity of an analyte that is being studied. As such, a velocity-altering agent may be a salt, a detergent, a buffer, a viscosity-altering substance, or any other agent added to a liquid medium that increases or decreases the velocity of an analyte. Typically, an analyte employed herein is soluble or partially soluble in at least one liquid medium that is in contact with an Msp described herein.

As used herein, nucleic acid refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides, such as peptide nucleic acids (PNAs) and phosphorothioate DNA. Unless otherwise indicated, a particular nucleic acid sequence includes the complementary sequence thereof. Nucleotides include, but are not limited to, ATP, dATP, CTP, dCTP, GTP, dGTP, UTP, TTP, dUTP, 5-methyl-CTP, 5-methyldCTP, ITP, diTP, 2-amino-adenosine-TP, 2-amino-deoxyadenosine-TP, 2-thiothymidine triphosphate, pyrrolo-pyrimidine triphosphate, and 2-thiocytidine, as well as the alphathiotriphosphates for all of the above, and 2'-0-methyl-ribonucleotide triphosphates for all the above bases. Modified bases include, but are not limited to, 5-Br-UTP, 5-BrdUTP, 5-F-UTP, 5-F-dUTP, 5-propynyl dCTP, and 5-propynyl-dUTP.

As used herein, a drug refers to any substance that may alter a biological process of a subject. Drugs can be designed or used for or in the diagnosis, treatment, or prevention of a disease, disorder, syndrome, or other health affliction of a subject. Drugs can be recreational in nature, that is, used simply to alter a biological process and not used for or in the diagnosis, treatment, or prevention of a disease, disorder, syndrome, or other health affliction of a subject. Biologics, which refer to substances produced by biological mechanisms involving recombinant DNA technology, are also encompassed by the term drug. Drugs include, for example, antibacterials, anti-inflammatoires, anticoagulants, antivirals, antihypertensives, antidepressants, antimicrobials, analgesics, anesthetics, beta-blockers, bisphosphonates, chemotherapeutics, contrast agents, fertility medications, hallucinogens, hormones, narcotics, opiates, sedatives, statins, steroids, and vasodilators. Non-limiting examples of drugs can also be found in the Merck Index: an Encyclopedia of Chemicals, Drugs, and Biologicals, $15^{th}$ ed. New Jersey: Merck, 2013. Antibacterial drugs used in the treatment of tuberculosis, for example, include isoniazid, rifampicin, pyrazinamide, and ethambutol. Methods employing a drug as an analyte can further comprise drug screening. For example, uptake of a drug into a cell or an organism can be investigated using an Msp by observing ion current blockades. Specific Msp porin constriction zones and/or vestibules with various sizes, electrostatic properties, and chemical properties can be constructed to closely emulate the desired pathway for drugs to enter or exit a cell or organism. These methods could greatly accelerate screening for drugs as well as drug design (see, for example, Pagel et al., *J. Bacteriology* 189:8593 (2007)).

As used herein, a biological warfare agent refers to any organism or any naturally occurring, bioengineered, or synthesized component of any such microorganism capable of causing death or disease in plants or animals (including humans) or degradation of food or water supplies, or degradation of the environment. Non-limiting examples include Ebola viruses, Marburg virus, *Bacillus anthracis* and *Clostridium botulinum, Variola major, Variola minor*, anthrax, and ricin.

As used herein, a pollutant refers to a material that pollutes air, water, or soil. Non-limiting examples of pollutants include fertilizers, pesticides, insecticides, detergents, petroleum hydrocarbons, smoke, and heavy metal-containing substances, such as those containing zinc, copper, or mercury (e.g., methylmercury).

Any analyte can be used herein, including, for example, a nucleotide(s), a nucleic acid, an amino acid(s), a peptide, a protein, a polymer, a drug, an ion, a biological warfare agent, a pollutant, a nanoscopic object, or any other molecule comprising one of these analytes or a combination of thereof. An analyte can be a cluster of molecules (e.g. 2-10 nucleotides or amino acids), in that the cluster as a whole is considered an analyte. Typically, an analyte's size will not be so great such that it cannot enter a tunnel of an Msp. In other words, a typical analyte will be smaller in size than the opening of a tunnel of an Msp. However, an analyte having a size larger than the opening of a tunnel can be employed, and it can be determined that the analyte's size is too large to enter the tunnel. Optionally, the molecular weight of the analyte is less than one million Da. Optionally, the molecular weight of the analyte is about, at most about, or at least about 1,000,000, 950,000, 900,000, 850,000, 800,000, 750,000, 700,000, 650,000, 600,000, 550,000, 500,000, 450,000, 400,000, 350,000, 300,000, 250,000, 200,000, 150,000, 100,000, 75,000, 50,000, 25,000, 20,000, 15,000, 10,000, 7,500, 5,000, 2,500, 2,000, 1,500, 1,000, or 500 Da or less, or any range derivable therein.

An analyte can also be a nanoscopic object, which is an object that is smaller than 100 nm in two of its dimensions.

As used herein, an analyte can further comprise a magnetic bead. A magnetic bead can be further defined as a streptavidin-coated magnetic bead. An analyte can further comprise an optical bead. Any analyte described herein can be an ion or can be neutral. An analyte can comprise biotin.

Beads that can be employed include magnetic beads and optical beads. For example, one can use streptavidin-coated magnetic beads to apply an opposing force to the electrostatic forces that pull DNA through the tunnel of an Msp. In this latter technique a magnetic bead is attached to biotinylated DNA, and a force comparable to the electrostatic driving force (~10 pN) would be applied using a strong magnetic field gradient. See Gosse and Croquette, *Biophys. J.* 82:3314 (2002). In this way, the blockade-current readout would be unaffected, but the forces on the DNA could be independently controlled. Tens or hundreds of complete, independent reads of each DNA could then be correlated and assembled to reconstruct an accurate DNA sequence.

Optical beads manipulated by "optical tweezers" are also known in the art, and such methods can be applied to the Msps described herein. Optical tweezers are a common tool used to exert a force on a nanoscopic object. An analyte is attached on one end of the bead, while the other end can be inserted into the tunnel of the porin. The position and force of the bead is controlled and measured with the optical tweezers. Such methods control the passage of the analyte into the tunnel and allow for more control of the reading of the analyte, such as the reading of the units of a polymer. See, e.g., Trepagnier et al., *Nano Lett.* 7:2824 (2007) for a description of such methods in the context of artificial nanopores. U.S. Pat. No. 5,795,782, incorporated herein by reference, also discusses the use of optical tweezers.

Fluorescence resonance energy transfer (FRET), a well-known technique, can be employed in analytical methods described herein. For example, a fluorescent FRET acceptor or FRET-donor molecule can be incorporated into an Msp. The analyte is then labeled with a matching FRET-donor or FRET-acceptor. When the matching FRET donor is within the Forster distance to the FRET acceptor, energy transfer will likely occur. The resulting signal could be used for analytical purposes instead of or in addition to methods using ion current as described herein. Accordingly, methods of detection, identification, or sequencing can comprise FRET technology. Other optical methods that can be employed include introducing optically active molecules into the interior of an Msp (such as the vestibule or the constriction zone). External light would be applied to affect the interior of the protein. Such methods could be used to affect the translocation velocity of an analyte or could allow the analyte's entry or exit from the tunnel, offering controlled passage of the analyte. Alternatively, optical pulses focused onto the pore could be used to heat the pore to affect how it interacts with the analyte. Such control could be very fast as the heat from a small volume of a focal point would dissipate rapidly. Methods of controlling the translocation velocity of an analyte can therefore employ such optically active molecules or optical pulses. Manipulation of translocation velocity can also be accomplished by attaching an object to one end of an analyte, and the other end of the analyte then interacts with the Msp. The object can be a bead (e.g., a polystyrene bead), a cell, a large molecule such as streptavidin, neutravidin, DNA, etc., or a nanoscopic object. The object could then be subjected to a fluid flow or could be subject to passive viscous drag.

Molecular motors are well-known in the art and refer to a molecule (e.g., an enzyme) that physically interacts with an analyte, such as a polymer (e.g., a 15 polynucleotide), and is capable of physically moving the analyte with respect to a fixed location, such as the vestibule, constriction zone, or tunnel of an Msp. Although not intending to be bound by theory, molecular motors utilize chemical energy to generate mechanical force. A molecular motor can interact with each unit (or "mer") of a polymer in a sequential manner. Non-limiting examples of molecular motors include DNA polymerases, RNA polymerases, helicases, ribosomes, and exonucleases. Nonenzymatic motors are also known, such as virus motors that pack DNA. See Smith et al., Nature 413:748 (2001). A variety of molecular motors and desirable properties of such motors are described in U.S. Pat. No. 7,238,485, which is incorporated herein by reference in its entirety.

A molecular motor can be disposed on the cis side or the trans side of an Msp porin and can optionally be immobilized, such as described by the '485 patent. Methods of incorporating a molecular motor into an Msp can be performed using methods described in the '485 patent. Systems and apparatuses described in the '485 patent can be employed with respect to an Msp described herein as well. Indeed, any embodiment discussed in the '485 patent can be employed using an Msp, as described herein. Molecular motors are also discussed in, e.g., Cockroft et al., J. Amer. Chem. Soc. 130:818 (2008); Benner et al., Nature Nanotech. 2:718 (2007); and Gyarfas et al., ACS Nano 3:1457 (2009).

A molecular motor is typically employed to regulate the rate or translocation velocity at which an analyte interacts with an Msp. Any Msp described herein can comprise a molecular motor. Optionally, a molecular motor is employed to decrease the rate at which an analyte enters an Msp porin tunnel or to decrease the translocation velocity at which an analyte translocates through an Msp tunnel. Optionally, the translocation velocity or average translocation velocity is less than 0.5 nm/µs. Optionally, the translocation velocity or average translocation velocity is less than 0.05 nm/µs. Optionally, the translocation velocity or average translocation velocity is less than 1 nucleotide/µs. Optionally, the translocation velocity or average translocation velocity is less than 0.1 nucleotide/µs.

Optionally, the rate of movement of an analyte ranges from greater than 0 Hz to 2000 Hz. Here, rate refers to the number of subunits (or "mers") of a regular polymer advancing in one second (Hz). Optionally, the range is between about 50-1500 Hz, 100-1500 Hz, or 350-1500 Hz. Optionally, the rate of movement is about, at most about, or at least about 25, 75, 100, 150, 200, 250, 300, 15 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 Hz, or any range derivable therein. The rate can be controlled by the use of a molecular motor that moves an analyte at a substantially constant rate, at least for a portion of time during a characterization. In addition, the range of rate of movement can depend on the molecular motor. For example, for an RNA polymerase, a range can be 350-1500 Hz; for a DNA polymerase, a range can be 75-1500 Hz; and for ribosomes, helicases, and exonucleases, a range can be 50-1500 Hz.

Recording and detection techniques can be employed in the methods described herein. In addition, U.S. Pat. Nos. 5,795,782 and 7,189,503, incorporated herein by reference in its entirety, also describes recording methods and instrumentation that can be employed with respect to Msps, as well as methods for optimizing conductance readings. U.S. Pat. No. 6,746,594, incorporated herein by reference in its entirety, describes a support for thin films containing nanopores and methods for using such supports that can be employed with respect to the Msps described herein.

Method of Making a Single Chain Msp

The Msp pore, for example, MspA, is currently the best available channel protein for nanopore sequencing of nucleic acids. However, its composition of eight subunits makes it impossible to introduce asymmetric changes in the pore that could optimize the properties of the Msp for nucleic acid sequencing. In order to overcome this difficulty, methods of making a single chain Msp are provided herein. These methods can be used to produce a full or partial single-chain Msp. Generally, the method comprises transforming a mutant bacterial strain. The mutant strain comprises a deletion of a wild-type MspA, a wild-type MspB, a wild-type MspC, a wild-type MspD, and optionally a deletion of the recA gene. The mutant strain is transformed with a vector comprising a nucleic acid sequence encoding a single-chain Msp porin. The single-chain Msp porin is then purified from the bacteria. Optionally, the single-chain Msp porin comprises a single-chain MspA porin. Optionally, the vector comprises any of the nucleic acids described herein.

As described in the Examples, in order to combine the superior sequencing capabilities of MspA with an increased ability to adapt vestibule and constriction properties to DNA sequencing, a single-chain MspA porin octamer was constructed that allows for the optimal properties of the vestibule and the constriction zone for DNA sequencing. The MspA chain termini are close together in the MspA porin and are connected by a short peptide linker. The $(GGGGS)_3$ (SEQ ID NO:3) peptide, for example, is used to connect the carboxy-terminus of the preceding MspA monomer (or multimer) to the amino-terminus of the following MspA monomer (or multimer), which lacks signal peptide. To create a vector comprising the MspA porin sequence, each MspA monomer sequence is flanked by a unique restriction site, which allows the capability to mutate any individual monomer. To create an MspA porin sequence, each MspA sequence can be assembled stepwise to form a dimeric, tetrameric, and octameric single-chain MspA utilizing the unique restriction sites. To avoid problems of recombination in creating the single-chain MspA multimer, seven MspA genes are synthesized with different codon usages i.e., the genes encode the exact same amino acid sequence, however, the DNA sequence has been altered from the native MspA nucleotide sequence (SEQ ID NO: 10). To create the MspA porin sequence, the nucleotide sequence encoding the first Msp monomer can optionally contain a nucleic acid sequence encoding a leader sequence (e.g., amino acids 1 to 27 of SEQ ID NO: 6). Each of the seven Msp monomer sequences following the first Msp monomer sequence can comprise SEQ ID NO: 1 or SEQ ID NO: 1 with one or more mutations described herein. The vector comprising the MspA porin sequence is transformed into the quadruple porin mutant bacterial strain, as described in the Examples. Optionally, single chain Msps can be purified and subjected to a refolding procedure. For example, anion exchange chromatography in the presence of 8M urea can be used to obtain a pure fraction of a single chain Msp which is dialyzed against a buffer to remove urea. After dialysis, a refolding buffer comprising a refolding agent, for example, L-arginine and detergent, are added to the sample and purified, refolded single chain Msp is obtained. Refolding agents are known to those of skill in the art. These include, but are not limited to, arginine, arginine hydrochloride, arginineamide, glycineamide, proline, glycerol, and cyclodextrains (see, for example, Yamaguchi et al. *Biomolecules* 4: 235-251 (2014); and expression levels and oligomeric status of the MspA porin can be checked by Western blot or other immunohistochemical techniques known to those of skill in the art. The tunnel activity of the MspA porin can be determined by lipid bilayer experiments, as described in the Examples and as known to those of skill in the art.

Single chain $M1_8$-MspA pores insert much more frequently into lipid bilayers than a similar amount of octameric M1-MspA. Insertion of octameric MspA is a tedious procedure. Thus, single-chain Msps, such as those described herein facilitate setup of systems and methods of using Msp for detecting and identifying analytes, for example, for nucleic acid sequencing.

Method of Increasing Msp Insertion in a Lipid Bilayer

Provided herein is a method of increasing the number of Msp insertions in a lipid bilayer, comprising contacting any Msp described herein with a lipid to form a lipid-associated Msp and inserting the lipid-associated Msp of step into a lipid bilayer. Optionally, the contacting step comprises inserting the Msp in a lipid bilayer and disrupting the lipid bilayer to form a lipid-associated Msp. For example, an Msp can be inserted in a lipid bilayer that is subsequently disrupted. The disrupted lipid bilayer comprises Msp(s). Therefore, the Msp(s) are lipid associated. The lipid-associated Msp can then be contacted with other lipids to form another lipid bilayer that comprises the lipid-associated Msps. As used herein, a lipid bilayer is a thin membrane comprising lipid molecules, for example, phosopholipids, that can be used to insert any Msp provided herein. Therefore, in the methods provided herein, the Msp can be contacted with phospholipids, either as part of a lipid bilayer or not, in order to form lipid-associated Msp.

As set forth above, one of skill in the art can determine if an Msp inserts into a bilayer, by using techniques such as those described in Example 2 of U.S. Patent Publication No. 20120055792, incorporated herein in its entirety by this reference. All of the methods of making and using porins described in U.S. Patent Publication No. 20120055792 can be employed to make and use the Msp porins described herein. If the protein inserts into the bilayer, then the porin is a tunnel-forming protein. Typically, tunnel formation is detected by observing a discrete change in conductivity. See, U.S. Patent Publication No. 20120055792, and Niederweis et al., *Mol. Microbiol.* 33:933 (1999), both of which are incorporated herein by reference. The increase in Msp insertions can be an increase of about 10%, 20%, 30%, 40%, 50%, 60%, 70%, 80%, 90%, 100%, 200%, 300%, 400% or greater.

Detection Methods

Further provided is a method for detecting the presence of an analyte, comprising: (a) applying an electric field sufficient to translocate an analyte from a first conductive medium to a second conductive medium in liquid communication through any mutant Msp described herein; and (b) measuring an ion current, wherein a reduction in the ion current indicates the presence of the analyte in the first medium. Optionally, the first and second liquid conductive media are the same. Optionally, the first and second liquid conductive media are different. The mutant Msp porin can be any mutant Msp porin discussed herein. For example, the Msp porin can be a mutant single-chain Msp, a mutant Msp comprising 2-15 monomers or combinations thereof. As set forth above, a plurality of Msps can also be used in the methods described herein.

In the methods disclosed herein, an Msp can further comprise a molecular motor. The molecular motor can be capable of moving an analyte into or through a tunnel with a translocation velocity or an average translocation velocity that is less than the translocation velocity or average translocation velocity at which the analyte electrophoretically translocates into or through the tunnel in the absence of the molecular motor. Accordingly, in any embodiment herein comprising application of an electric field, the electric field can be sufficient to cause the analyte to electrophoretically translocate through the tunnel. Any liquid medium discussed herein, such as a conductive liquid medium, can comprise an analyte. In the methods comprising measuring an ion current, the analyte interacts with an Msp porin tunnel to provide a current pattern, wherein the appearance of a blockade in the current pattern indicates the presence of the analyte.

The methods disclosed herein can further comprise identifying the analyte. For example, such methods can comprise comparing the current pattern obtained with respect to an unknown analyte to that of a known current pattern obtained using a known analyte under the same conditions. In another example, and not to be limiting, identifying the analyte can comprise (a) measuring the ion current to provide a current pattern, wherein a reduction in the current defines a blockade in the current pattern, and (b) comparing one or more blockades in the current pattern to (i) one or more blockades in the current pattern, or (ii) one or more blockades in a known current pattern obtained using a known analyte.

The analyte can be any analyte described herein. For example, the analyte can be a nucleotide(s), a nucleic acid, an amino acid(s), a peptide, a protein, a polymer, a drug, an ion, a pollutant, a nanoscopic object, or a biological warfare agent. In the methods provided herein, optionally, at least one of the first or second conductive liquid media comprises a plurality of different analytes.

In methods where the analyte is a polymer, for example, a protein, a peptide or a nucleic acid, the method can further comprise identifying one or more units of the polymer. For example, identifying one or more units of the polymer can comprise measuring the ion current to provide a current pattern comprising a blockade for each polymer unit, and comparing one or more blockades in the current pattern to (i) one or more other blockades in the current pattern or (ii) one or more blockades in a current pattern obtained using a polymer having known units. These methods can comprise identifying sequential units of the polymer, for example, and not to be limiting, sequential or consecutive nucleotides in a nucleic acid. In another example, sequential or consecutive amino acids in a polypeptide can be identified using the methods described herein.

The methods provided herein can comprise distinguishing at least a first unit within a polymer from at least a second unit within the polymer. Distinguishing can comprise measuring the ion current produced as the first and second units separately translocate through a tunnel to produce a first and a second current pattern, respectively, where the first and second current patterns differ from each other.

The methods provided herein can further comprise sequencing a polymer. Sequencing can comprise measuring the ion current or optical signals as each unit of the polymer is separately translocated through the tunnel to provide a current pattern that is associated with each unit, and comparing each current pattern to the current pattern of a known unit obtained under the same conditions, such that the polymer is sequenced.

Further provided is a method of sequencing nucleic acids or polypeptides using any of the mutant Msps provided herein. The method comprises creating a lipid bilayer comprising a first and second side, adding a purified Msp to the first side of the lipid bilayer, applying positive voltage to the second side of the lipid bilayer, translocating an experimental nucleic acid or polypeptide sequence through the Msp porin, comparing the experimental blockade current with a blockade current standard, and determining the experimental sequence.

Any of the detection methods provided herein can further comprise determining the concentration, size, molecular weight, shape, or orientation of the analyte, or any combination thereof.

As used herein, a polymer refers to a molecule that comprises two or more linear units (also known as a "mers"), where each unit may be the same or different. Non-limiting examples of polymers include nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). Polymers include copolymers, block copolymers, and branched polymers such as star polymers and dendrimers.

Methods of sequencing polymers using Msp are described herein. In addition, sequencing methods can be performed in methods analogous to those described in U.S. Pat. No. 7,189,503, incorporated herein by reference in its entirety. See also U.S. Pat. No. 6,015,714, incorporated herein by reference in its entirety. More than one read can be performed in such sequencing methods to improve accuracy. Methods of analyzing characteristics of polymers (e.g., size, length, concentration, identity) and identifying discrete units (or "mers") of polymers are discussed in the '503 patent as well, and can be employed with respect to the present Msps. Indeed, an Msp can be employed with respect to any method discussed in the '503 patent.

At present, several types of observable signals can be used as readout mechanisms in nanopore sequencing and analyte detection. An exemplary readout method relies on an ionic blockade current or copassing current, uniquely determined by the identity of a nucleotide or other analyte occupying the narrowest constriction in the pore. This method is referred to as blockade current nanopore sequencing or BCNS. Blockade current detection and characterization of nucleic acids has been demonstrated in both the protein pore ahemolysin (aHL) and solid-state nanopores.

Blockade current detection and characterization has been shown to provide a host of information about the structure of DNA passing through, or held in, a nanopore in various contexts. In general, a blockade is evidenced by a change in ion current that is clearly distinguishable from noise fluctuations and is usually associated with the presence of an analyte molecule at the pore's central opening. The strength of the blockade will depend on the type of analyte that is present. More particularly, a blockade refers to an interval where the ionic current drops below a threshold of about 5-100% of the unblocked current level, remains there for at least 1.0 us, and returns spontaneously to the unblocked level. For example, the ionic current may drop below a threshold of about, at least about, or at most about 5%, 10%, 15%, 20%, 25%, 30%, 35%, 40%, 45%, 50%, 55%, 60%, 65%, 70%, 75%, 80%, 85%, 90%, 95%, or 100%, or any range derivable therein. Blockades are rejected if the unblocked signal directly preceding or following it has an average current that deviates from the typical unblocked level by more than twice the rms noise of the unblocked signal. Deep blockades are identified as intervals where the ionic current drops <50% of the unblocked level. Intervals where the current remains between 80% and 50% of the unblocked level are identified as partial blockades.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations may not be explicitly disclosed, each is specifically contemplated and described herein. For example, if a method is disclosed and discussed and a number of modifications that can be made to a number of compositions included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed. It is also contemplated that any embodiment discussed in this specification can be implemented with respect to any method, compound, protein, porin, peptide, polypeptide, multimer, monomer, nucleic acid, vector, strain, cultured cell, system, or composition, etc., described herein, and vice versa.

Publications cited herein and the material for which they are cited are hereby specifically incorporated by reference in their entireties.

A number of embodiments have been described. Nevertheless, it will be understood that various modifications can be made. Accordingly, other embodiments are within the scope of the following claims.

EXAMPLES

A single-chain MspA was constructed consisting of eight covalently connected monomers. As shown herein, an expression plasmid encoding single-chain M1-MspA is not stable in wild-type *M. smegmatis* but can be propagated in an *M. smegmatis* lacking the recA gene, which is required for homologous recombination. The recA gene was deleted in the quadruple porin mutant *M. smegmatis* ML712, which lacks the four known Msp porins. This strain enabled expression of single-chain M1-MspA. Tunnels made by single-chain M1-MspA had a similar conductance as octameric M1-MspA tunnels, but had drastically improved resistance to voltage gating. This unforeseen advantage of single-chain MspA is of great importance for nanopore sequencing of nucleic acids, for example, DNA.

Construction of an Msp Quadruple Deletion Mutant of *M. smegmatis*

For isolation of mutant MspA porins a triple porin deletion mutant *Mycobacterium smegmatis* ML 16 strain (ΔmspA::FRT, ΔmspC::FRT, ΔmspD::FRT) was used (see Stephan et al., Mol. Microbiol. 58: 714-730 (2005)). However, low levels of MspB could still be detected in this strain in immunoblots with MspA-specific rabbit antiserum. The presence of MspB can contribute to the heterogeneity observed in single-channel experiments and complicates data analysis. In order to overcome this problem and improve MspA preparations an M. smegmatis strain lacking all four msp genes was constructed.

Figure 2:
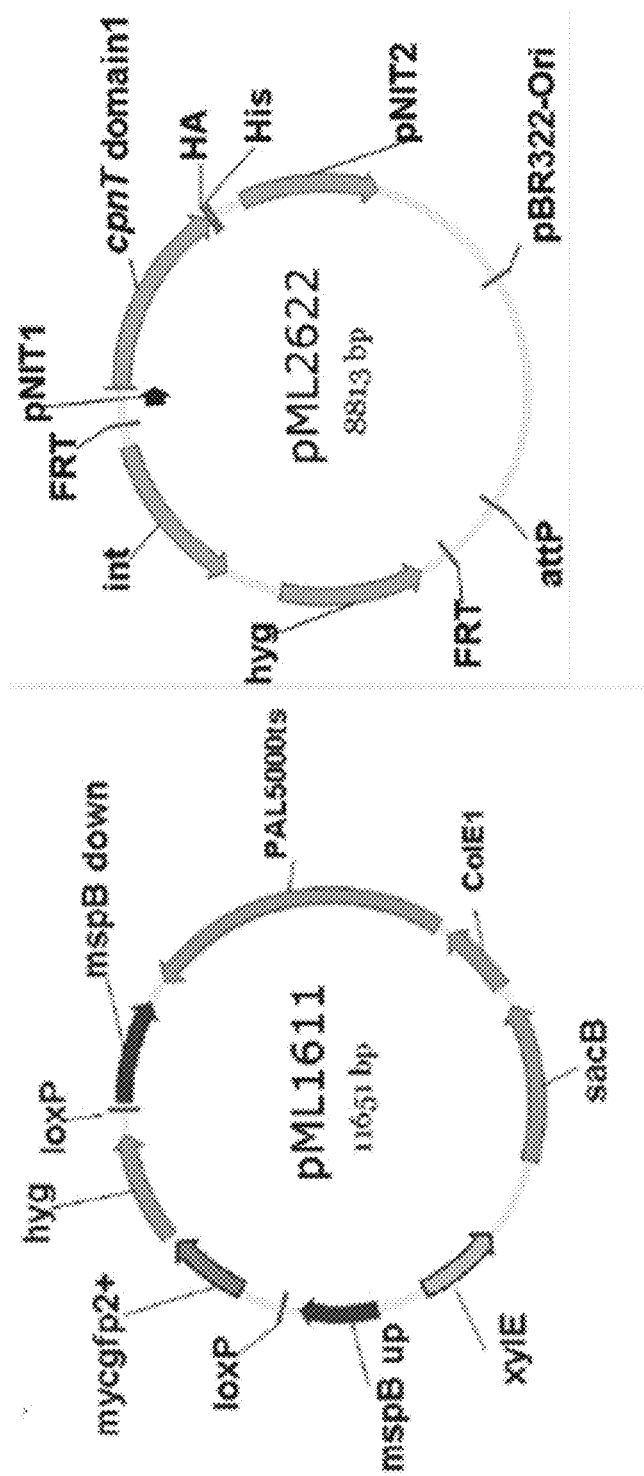
FIG. 2 shows schematic representations of the plasmids used for construction of ML712 *M. smegmatis*. pML1611—mspB is a deletion vector: mspBup, mspBdown—regions homologus upstream and downstream of to mspB chromosomal gene; loxP—recombination site for Cre recombinase, hyg—hygromycin resistance; sacB—levansucrase; xylE—catechol-2,3-dioxygenase; gfp2+—green fluorescent protein; tsPAL5000: temperature-sensitive origin of replication for mycobacteria; ColE1—*E. coli* origin of replication. pML2622—integrative plasmid for expression of the N-terminal channel-forming domain (d1) of cpnT. hyg: hygromycin resistance gene; pBR322-Ori: *E. coli* origin of replication; pNIT1 and pNIT2 are required for nitlrile-inducible expression of epnT, attP: chromosome attachment site of the phage L5; int: L5 integrase; FRT: Flp recombines site.

Since the deletion of all four msp genes of M. smegmatis is lethal, the first step was to integrate an expression cassette for the N-terminal channel-forming domain of CpnT (1) into the M. smegmatis porin triple mutant ML 16. To this end, the plasmid pML2622 was constructed, which carries the N-terminal domain of CpnT tagged with His6 and HA under the control of a nitrile-inducible promoter (FIG. 2). The N-terminal domain of CpnT formed channels in planar bilayer experiments and complemented the porin mutant M. smegmatis ML16 strain in glycerol uptake experiments. The rescue plasmid pML2622 was integrated into the mycobacteriophage L5-site in the chromosome of the porin triple mutant M. smegmatis ML16. Integration was confirmed by PCR with the sets of primers complimentary to L5 genomic region. This strain was named M. smegmatis ML709. After integration of pML2622, the plasmid backbone was excised from the chromosome by Flp recombinase as described in Stephan et al. (Gene 343: 181-190 (2004)) to remove the genes encoding hygromycin phosphotransferase and L5 integrase. This strain was named M. smegmatis ML709-234.

To delete the remaining mspB gene in M. smegmatis ML711 the mspB deletion vector pML1611 containing the two reporter genes gfp and xylE as markers for integration and allelic replacement was constructed (FIG. 2). The mspB deletion vector pML 1611 carries 863 bp and 946 bp-long upstream and downstream regions of mspB and was used to delete the mspB gene in M. smegmatis ML709-234 by allelic exchange. This Msp porin quadruple mutant was named M. smegmatis ML711. The plasmid pCreSacB containing Cre recombinase was used to excise gfp and hyg genes flanked by loxP sites from the chromosome. The deletion of all four msp genes was confirmed by PCR with chromosomal DNA using specific sets of primers and by Southern blot with chromosomal DNA using specific probe (FIG. 3). This unmarked Msp porin quadruple mutant was named M. smegmatis ML712 (relevant genotype: ΔmspA::FRT, ΔmspB::loxP, ΔmspC::FRT, ΔmspD::FRT, attB L5:: FRT-pNIT-cpnT$_{d1}$-FRT). The growth of the strain ML712 on Middlebrook 7H10 agar plates was impaired in comparison to wt and ML16 strains. Next, the expression of msp genes in the ML712 strain was assessed by extraction of M. smegmatis cells using the detergent octylpolyethyleneoxide as described in Heinz et al. (Anal. Biochem. 285: 113-120 (2000)). The Msp quadruple porin deletion mutant M. smegmatis ML712 grown in Middlebrook 7H9 medium does not produce any Msp protein in contrast to the porin triple mutant ML16 (FIG. 4). This demonstrated that deletion of all msp genes was achieved in M. smegmatis ML712. The expression levels of the MspA were similar to that of wt M. smegmatis, when wt mspA or M1 mspA were expressed in ML712 using the plasmids pMN016 and pML904, respectively (FIG. 4).

Construction of Single-Chain M1-MspA

Previously a M1$_2$-MspA subunit dimer was constructed (Pavlenok et al. PLOS One 7(6): e38726). As the next step towards single-chain MspA, four mspA-M1 genes were fused to encode a M1$_4$-MspA subunit tetramer. The resulting plasmid pML2647 was transformed into the quadruple porin deletion strain of M. smegmatis ML712 for protein production and purification. However, the tetrameric mspA plasmid was unstable. In order to avoid recombination, the recA gene was deleted in the quadruple porin mutant ML712 and the strain M. smegmatis ML714 was created.

Then, a gene encoding single-chain MspA, in which eight M1-MspA subunits are linked (M1$_8$-MspA), was cloned into E. coli. Each of the subunits has a D90N mutation, a D91N mutation and a D93N mutation. This was achieved by fusing two genes encoding tetrameric M1 MspA together (M1$_4$-MspA) using pML2647 as a template. The individual MspA subunits are separated by (GGGGS)$_3$ linkers. In the resulting plasmid pML3213, the two tetrameric M1-mspA constructs are flanked by unique restriction sites (tetrad A: PacI, MluI; tetrad B: EcoRV, HindIII) (FIG. 5). Genes within the tetramers are flanked by the same restriction sites with the exception of the first and last genes of the tetrads.

The resulting m1$_8$-mspA gene was placed under the control of the constitutive p$_{smyc}$ promoter (FIG. 5). The plasmid pML3213 was transformed into M. smegmatis ML714 (quadruple porin mutant with recA deletion) for protein production and purification. Western blot experiments showed that the expression level of single-chain M1$_8$-MspA in M. smegmatis ML714 is lower compared to M1$_2$-MspA and is reduced to approximately 7% of wt MspA levels (FIG. 6).

Stability of Single-Chain M1-MspA

The MspA pore is very resistant against thermal and chemical denaturation (Heinz et al. J. Biol. Chem. 278: 8678-8685 (2003)). To test the thermal stability of single-chain MspA, the M1$_8$-MspA protein was subjected to increasing temperatures for 15 min in the presence of 2% SDS. (FIG. 7) A significant amount of M1$_8$-MspA is stable even after heating the protein sample to 100° C. (FIG. 7). This result shows that M1$_8$-MspA is at least as stable against thermal denaturation as the wt MspA protein.

Channel Properties of Single-Chain M1-MspA

To examine whether M1$_8$-MspA forms functional channels, in vitro lipid bilayer experiments were performed. No insertions were recorded when only n-octyl-POE buffer was added to the lipid bilayer. Addition of approximately 70 ng of M1$_8$-MspA protein resulted in the step-wise increase in the current across the lipid bilayer indicating the insertion of M1$_8$-MspA channels into the membrane (FIG. 8A). Analysis of the current recordings of M1$_8$-MspA showed a major peak of 1.1 nS (FIG. 8B). This channel conductance is similar to those of the pores made from the M1-MspA dimer (1.3 nS) and M1 MspA monomers (1.4 nS) (see Pavlenok et al.).

Voltage Gating

Voltage gating is defined as a spontaneous channel closure at a certain voltage threshold and is an intrinsic property of bacterial B-barrel channel proteins (Bainbridge et al. FEBS Lett 431(3): 305-308 (1998)). Resistance to voltage gating is very important for nanopore sequencing experiments since voltages as high as +180 mV are used to translocate ssDNA through MspA pore (Manrao et al. Nat. Biotechnol. 30(4): 349-353 (2012); Derrington et al. Proc. Natl. Acad. Sci. USA 107(37): 16060-16065 (2010); Butler et al. Proc. Natl. Acad.

Sci. USA 105(52): 20647-20652 (2008)). Therefore, the voltage gating of M1$_8$-MspA in lipid bilayer experiments was analyzed. After insertion of approximately 220 M1$_8$-MspA pores, the voltage across the lipid bilayer was sequentially increased in 10 mV increments, and the ion current passing through the pores was measured for three minutes. The critical voltage Vc is defined as the voltage at which pores start to close, and is measured in these experiments as decrease of ion current.

The M1$_8$-MspA channels started to close at +90 mV and were completely stable at all applied negative voltages (FIG. 9). In a second experiment with gel-purified M1$_8$-MspA protein no voltage gating, up to voltages of ±100 mV, was observed. Thus, the critical voltage $V_c$ of M1$_8$-MspA is two-fold higher than that of M1-MspA or M1$_2$-MspA ($V_{crit}$+ 40 mV, −50 m V for both proteins). These results show that linking all eight subunits into a single polypeptide drastically increased the resistance of single-chain MspA to voltage gating. This unforeseen advantage of single-chain MspA is of great importance for nanopore sequencing of nucleic acids, for example, DNA.

Construction of a Mutant Single Chain MspA (scMspA M2)

As described herein, mutations in MspA are useful for improving its interactions with DNA, its base recognition properties and its interactions with membranes and accessory proteins such, for example, Phi29 DNA polymerase. Using the approach described above for single-chain M1 MspA, a mutant single-chain MspA (MspA M2), in which eight mutant MspA monomers are linked together was constructed. Expression of both single-chain M1 MspA and single-chain MspA M2 constructs in *M. smegmatis* ML712 was shown by Western blots using an MspA antibody demonstrating that production of scMspA in *M. smegmatis* is feasible. As shown herein, single chain Msps can be expressed in *E. coli*. The single chain M2 MspA (scMspA M2) protein is made in mg amounts, but is not folded. A folding protocol has been developed that allows isolation of active scMspA M2.

A single-chain m2-mspA (scm2-mspA) where eight m2-mspA genes (containing the mutations D90N/D91N/D93N/D118R/D134R/E139K as described in Butler et al. (*PNAS* 105: 20647-20652 (2008)) were connected by DNA fragments encoding (GGGGS)3 polypeptide linkers. In addition, each gene was flanked by unique restriction sites to enable specific modifications of each MspA subunit. The genes in the sequence are named m2-1 through m2-8 beginning from the ATG start codon (FIG. 11 and Table 3). For protein production and purification of the single-chain MspA M2 protein in *E. coli* cells the signal peptide of MspA was removed. The sem2-mspA sequence was codon optimized for optimal expression in *E. coli* and was synthesized by GenScript. The resulting sem2-mspA gene was flanked by EcoRI and HindIII and was obtained in a pUC57 plasmid from GenScript. Next, the whole sc m2-mspA was excised and cloned into the pET-21(a)+ vector. The scm2-mspA gene is under the control of the T7 promoter in the resulting plasmid pML3216 (FIG. 11).

For scMspA M2 protein production and purification, the plasmid pML3216 was transformed into *E. coli* BL21(DE3) Omp8 strain which lacks 3 major porins (See Prilipov et al. *FEMS Microbiol. Lett* 163: 65-72 (1998)). The BL21(DE3) Omp8 strain was chosen to avoid contamination of scMspA M2 with endogenous porins of *E. coli*. After induction of sem2-mspA expression with 1.5 mM IPTG cells were grown at 37° C. in LB medium supplemented with ampicillin. Maximal expression of the target protein was observed two hours after induction accounting for approximately 4% of the total protein in the cell lysate (FIG. 12). A protein band corresponding to scMspA M2 had an apparent mass of 170 kDa which is consistent with its predicted molecular mass of 165.6 kDa (FIG. 12). Next, scMspA M2 from inclusion bodies was isolated and purified as described in Sambrook et al. (*CSH Protocols* 2006) Inclusion bodies containing predominantly scMspA M2 protein were solubilized in 8 M urea. This sample was later a subject to anion exchange chromatography using HiTrap QFF column (GE Health-Care, United Kingdom) in the presence of 8 M urea. The elution profile of scMspA M2 protein was very similar to that of wt MspA published previously (Heinz et al., 2003). This protein is probably not folded and has no channel activity.

Then, scMspA M2 was purified and subjected to a refolding procedure. After anion exchange chromatography a pure fraction of scMspA M2 with a concentration of 50 µg/ml was diluted by a factor of 10 in a buffer containing 10 mM NaCl, 25 mM HEPES, 0.6 M L-Arginine, 0.1% (v/v) LDAO, pH 8.0 to give final volume of 1 ml. The mixture was incubated overnight at room temperature (approximately 21° C.) on a rotating mixer. Then, the sample was transferred into a dialysis tube with 3.5 kDa MWCO and dialyzed against 2 L of a buffer containing 10 mM NaCl, 25 mM HEPES (pH 8.0), 0.023% (v/v) LDAO overnight at room temperature. The dialyzed protein was transferred into a microtube and incubated at a room temperature for an additional day. Next, the refolding efficiency was assessed by Western blot analysis using MspA-specific rabbit antiserum. After the refolding procedure, the band which reacts with MspA polyclonal antibodies migrated from 170 kDa to approximately 130 kDa indicating that folding of scMspA M2 to a more compact form with an increased electrophoretic mobility had occurred (FIG. 13). Such an electrophoretic mobility shift upon folding has been observed for outer membrane proteins of *E. coli* previously. However, it was not clear whether MspA would show a similar phenomenon.

In order to examine if scMspA M2 forms functional channels in vitro after the refolding procedure lipid bilayer experiments were performed. No channel activity was observed when only 0.023% LDAO-buffer was added to the planar bilayer. In contrast, addition of scMspA M2 protein after the refolding step resulted in a step-wise current increase indicative of channel insertions into lipid bilayer (FIG. 14). Analysis of the current traces showed an average conductance of 2.3 nS (FIG. 14). Of interest, analysis of MspA M2 made from monomers showed two peaks at 1.2 nS and 2.4 nS suggesting two different protein conformations. In addition, a multi-channel experiment with scMspA M2 showed improved voltage-gating resistance with a critical voltage of +80 mV/−70 mV (FIG. 15). The increased voltage resistance is beneficial for example, for ssDNA experiments performed at relatively high voltages.

TABLE 3

Restriction sites of scMspA M2

| # of RS | RS | Sequence | Ends | Amino acids | Gene flanked |
|---|---|---|---|---|---|
| 1 | EcoRI | GAATTC | cohesive | EF | m2-1 |
| 2 | KpnI | GGTACC | cohesive | GT | |
| 3 | NsiI | ATGCAT | cohesive | MH | m2-2 |

TABLE 3-continued

Restriction sites of scMspA M2

| # of RS | RS | Sequence | Ends | Amino acids | Gene flanked |
|---|---|---|---|---|---|
| 4 | ScaI | AGTACT | blunt | ST | |
| 5 | NheI | GCTAGC | cohesive | AS | m2-3 |
| 6 | HpaI | GTTAAC | blunt | VN | |
| 7 | XbaI | TCTAGA | cohesive | SR | m2-4 |
| 8 | NdeI | CATATG | cohesive | HM | |
| 9 | EcorV | GATATC | blunt | DI | m2-5 |
| 10 | PstI | CTGCAG | cohesive | LQ | |
| 11 | BstBI | TTCGAA | cohesive | FE | m2-6 |
| 12 | BamHI | GGATCC | cohesive | GS | |
| 13 | MluI | ACGCGT | cohesive | TR | m2-7 |
| 14 | PvuII | CAGCTG | blunt | QL | |
| 15 | Afl II | CTTAAG | cohesive | LK | m2-8 |
| 16 | HindIII | AAGCTT | cohesive | KL | |

Construction of Mutant Single Chain MspA (MspA PN1)

A single-chain mspA pn1 (scmspA PN1) gene where eight mspA genes (containing a P97F mutation and mutations D90N/D91N/D93N/D118R/D134R/E139K as described in Butler et al. (*PNAS* 105: 20647-20652 (2008)) were connected by DNA fragments encoding (GGGGS)$_3$ polypeptide linkers. In addition, each gene was flanked by unique restriction sites to enable specific modifications of each MspA subunit. The genes in the sequence are named m2-97-1 through m2-97-8 beginning from the ATG start codon (FIG. 16 and Table 3). For protein production and purification of the single-chain MspA PN1 protein in *E. coli* cells the signal peptide of MspA was removed. The scmspA PN1 sequence was codon optimized for optimal expression in *E. coli* and was synthesized by GenScript. The resulting scmspA PN1 gene was flanked by EcoRI and HindIII and was obtained in a pUC57 plasmid from GenScript. Next, the entire scmspA PN1 was excised and cloned into the pET-21(a)+ vector. The scmspA PN1 gene is under the control of the T7 promoter in the resulting plasmid pML3216 (FIG. 16).

For scMspA PN1 protein production and purification the plasmid pML3216 was transformed into *E. coli* BL21(DE3) Omp8 strain which lacks 3 major porins (See Prilipov et al. *FEMS Microbiol. Lett* 163: 65-72 (1998)). The BL21(DE3) Omp8 strain was chosen to avoid contamination of scMspA PN1 with endogenous porins of *E. coli*. After induction of semspA PN1 expression with 1.5 mM IPTG, cells were grown at 37° C. in LB medium supplemented with ampicillin. Maximal expression of the target protein was observed two hours after induction accounting for approximately 5% of the total protein in the cell lysate (FIG. 17). A protein band corresponding to scMspA PN1 had an apparent mass of 170 kDa which is consistent with its predicted molecular mass of 165.6 kDa (FIG. 17). Next, scMspA PN1 from inclusion bodies was isolated and purified as described in Sambrook et al. (*CSH Protocols* 2006) Inclusion bodies containing predominantly scMspA PN1 protein were solubilized in 8 M urea. This sample was later a subject to anion exchange chromatography using HiTrap QFF column (GE HealthCare, United Kingdom) in the presence of 8 M urea. The elution profile of scMspA PN1 protein was very similar to that of wt MspA published previously (Heinz et al., 2003). This protein is probably not folded and has no channel activity.

Then, scMspA PN1 was purified and subjected to a refolding procedure. After anion exchange chromatography a pure fraction of scMspA PN1 was dialyzed against 2 L of buffer containing 140 mM NaCl, 10 mM K$_2$HPO$_4$/KH$_2$PO$_4$, 2 mM KCl (pH 7.5) to remove urea. The mixture was incubated overnight at room temperature (approximately 21° C.). After dialysis, L-arginine and LDAO were added to the sample to give a final concentration of 0.6M and 0.1% (v/v), respectively. The protein sample in the refolding buffer (140 mM NaCl, 10 mM K$_2$HPO$_4$/KH$_2$PO$_4$, 2 mM KCl, 0.6 M L-Arginine, 0.1% (v/v) LDAO, pH 7.5) was incubated overnight on an orbital shaker (FIG. 18). The concentration of the purified sample was calculated to be 1.37 mg/ml as determined by absorbance at 280 nm. The protein yield was 0.45 mg per 1 liter of bacterial culture.

To test the effect of phenylalanine at position 97 on incorporation of the single-chain MspA into artificial lipid membranes the insertion activity of different MspA constructs was measured by monitoring the release of fluorescent carboxyfluorescein dye from the liposomes as described (See Schwarz et al., Biophys. J. 58(3):577-83 (1990); Schwarz et al., Biochim. Biophys. Acta 1239(1): 51-7 (1995)). Briefly, DPhPC liposomes were prepared by extrusion in the presence of 30 mM carboxyfluorescein. Carboxyfluorescein is self-quenched when it is enclosed into lipid vesicles. After insertion of MspA pore into the dye-loaded liposome, diffusion-mediated efflux of the dye results in the increase of fluorescence in the reaction mixture. FIG. 19 shows the results of these carboxyfluorescein release experiments. Addition of buffers containing either LDAO (0.1% v/v) or OPOE (0.5% v/v) resulted in only minimal dye release from the liposomes, in contrast to Triton X-100 (1% v/v) buffer that was used as a positive control. Importantly, addition of scMspA PN1 (60 ng/ml, final) lead to faster and larger release of carboxyfluorscein than addition of scMspA M2 (120 ng/ml, final). Interestingly, wt MspA (60 ng/ml, final) resulted in slower dye diffusion from the liposomes than scMspA PN1 (FIG. 19). These data indicate that additional phenylalanines located in the loop 6 of scMspA promote faster and more efficient insertion of the pores into lipid bilayers.

Next, the time of the first pore insertion into DPhPC membrane was measured in a bilayer set up. It was hypothesized that pores with enhanced insertion abilities would require less time to insert into lipid membrane. To examine the effect of phenylalanines in loop 6 on the time of membrane insertion of scMspA, scMspA PN1 was compared with scMspA M2. Briefly, the bilayer cuvette was filled with electrolyte, −10 mV potential was applied, and the data were acquired and recorded using TestPoint software. The same cuvette was always used in these experiments. The protein was added to both sides at a final concentration of 100 ng/ml. Importantly, successful insertion events were observed in 89% of the experiments for scMspA PN1, but only in 40% of the experiments for scMspA M2. This is consistent with the results of the carboxyfluorescein release experiments. Although the median insertion time for scMspA PN1 was 399 seconds as opposed to 695 seconds for scMspA M2, this difference was not significant. Surprisingly, the rate of insertion decreased when scMspA PN1 was analyzed in 0.3M KCl solution (median time: 859 seconds, 50%). However, half of the experiments resulted in successful insertions with scMspA PN1, while only one successful insertion was observed with scMspA M2 in 0.3M KCl with a time of 1270 seconds (8 membranes analyzed, 12% successful insertions) (FIG. 20). This result shows the beneficial effect of phenylalanines in loop 6 for membrane insertion by single-chain MspA.

In order to examine whether scMspA PN1 forms functional channels in vitro after the refolding procedure, lipid bilayer experiments were performed. No channel activity was observed when only 0.1% LDAO-buffer was added to the planar bilayer. In contrast, addition of scMspA PN1 protein after the refolding step resulted in a step-wise current increase indicative of channel insertions into the lipid bilayer (FIG. 21). Analysis of the current traces showed an average conductance of 2.0 nS (FIG. 21). This could translate into larger residual currents for each nucleotide and better signals in DNA sequencing experiments.

Effect of Lipids on Channel Activity of Single-Chain MspA PN1 scMspA PN1 was stored for more than a month at room temperature in 1 µg/mg and 0.2 µg/ml amounts. The scMspA PN1 was diluted in 0.1% LDAO, 140 mM NaCl, 10 mM K2HPO4/KH2PO4 (pH 7.5), 2 mM KCL. Methods for making horizontal bilayers for channel experiments are known in the art. See, for example, Butler et al. (2008) and Akeson et al. Biophysical Journal; 77: 3227-3233 (1999), both of which are incorporated herein in their entireties. For the channel experiments, 2% diphtanoyl-phosphatidylcholine (DiphPC) in chloroform was used to form membrane bilayers for insertion of MspA essentially as described in Butler et al. and Akeson et al. After insertion of the MspA into the bilayers, the membrane was broken and the membrane was reapplied using 1% DiphPC in n-decane. The electrolyte used in these experiments was 0.3 or 1M KCl, 10 mM Hepes, pH 8.0 or pH 7.0, respectively.

As shown in FIG. 22, single-chain MspAs function at a wide range of electrolyte concentration, for example from about 0.3-1M KCl. To optimize channel activity, lipid association can be performed prior to insertion of MspA in a membrane or lipid bilayer. Therefore, in any of the methods set forth herein, an MspA can be contacted or preincubated with one or more lipids to optimize channel activity. In a non-limiting example, FIG. 22 shows that no channel activity was observed in a buffer containing only 0.3 M KCl at pH 8.0. However, breaking the membrane and subsequent repainting of the membrane leads to increased channel activity of scMspA PN1 in the electrolyte containing 0.3 M KCl at pH 8.0.

The invention claimed is:

1. A nucleic acid sequence encoding a mutant single-chain *Mycobacterium smegmatis* porin (Msp), wherein the nucleic acid sequence comprises:
(a) a first and second nucleotide sequence, wherein the first nucleotide sequence encodes a first Msp monomer sequence and the second nucleotide sequence encodes a second Msp monomer sequence; and
(b) a third nucleotide sequence encoding an amino acid linker sequence that links the first and second nucleotide sequence,
wherein at least one of the first and second Msp monomer sequences is a mutant Msp monomer sequence, wherein the mutant Msp monomer sequence has at least 95% sequence identity to SEQ ID NO: 1 and wherein the mutant Msp monomer sequence comprises (i) a P97F mutation; (ii) an amino acid with a positive charge at amino acid position 118, 134 and/or 139; and (iii) a mutation at amino acid position 90, amino acid position 91 and/or amino acid position 93.

2. The nucleic acid sequence of claim 1, wherein the mutant Msp monomer sequence comprises a D90N, a D91N and a D93N mutation.

3. The nucleic acid sequence of claim 1, wherein the mutant Msp monomer sequence comprises a P97F mutation, a D90N mutation, a D91N mutation, a D93N mutation, a D118R mutation, a D134R mutation and a E139K mutation.

4. The nucleic acid sequence of claim 1, wherein the second Msp monomer sequence is selected from the group consisting of a wild-type MspA monomer, a mutant MspA monomer, or a sequence having at least 95% sequence identity to SEQ ID NO: 2, SEQ ID NO: 3 or SEQ ID NO: 4.

5. A nucleic acid sequence encoding a mutant single-chain Msp, wherein the nucleic acid sequence comprises:
   (a) a first and second nucleotide sequence wherein the first nucleotide sequence encodes a first Msp monomer sequence and the second nucleotide sequence encodes a second Msp monomer sequence;
   (b) a third, fourth, fifth, sixth, seventh, and eighth nucleotide sequence or any subset thereof, wherein the third, fourth, fifth, sixth, seventh, and eighth nucleotide sequences encode a third, fourth, fifth, sixth, seventh, and eighth Msp monomer sequence, respectively, wherein the first, second, third, fourth, fifth, sixth, seventh and eighth nucleotide sequence or any subset thereof are arranged consecutively in the nucleic acid; and
   (c) at least one ninth nucleotide sequence encoding an amino acid linker sequence, wherein the ninth nucleotide sequence is positioned between any two consecutive nucleotide sequences encoding Msp monomer sequences
   wherein at least one of the first and second Msp monomer sequences is a mutant Msp monomer sequence, wherein the mutant Msp monomer sequence has at least 95% sequence identity to SEQ ID NO: 1 and wherein the mutant Msp monomer sequence comprises (i) a P97F mutation; (ii) an amino acid with a positive charge at amino acid position 118, 134 and/or 139; and (iii) a mutation at amino acid position 90, amino acid position 91 and/or amino acid position 93.

6. The nucleic acid sequence of claim 5, wherein the mutant Msp monomer sequence comprises a D90N, a D91N and a D93N mutation.

7. The nucleic acid sequence of claim 6, wherein the mutant Msp monomer sequence comprises a P97F mutation, a D90N mutation, a D91N mutation, a D93N mutation, a D118R mutation, a D134R mutation and a E139K mutation.

8. The nucleic acid sequence of claim 5, wherein one or more of the third, fourth, fifth, sixth, seventh or eighth Msp monomer sequence is selected from the group consisting of a wild-type MspA monomer, a mutant MspA monomer, or an MspA having at least 95% sequence identity to SEQ ID NO: 2, SEQ ID NO: 3 or SEQ ID NO: 4.

9. A vector comprising the nucleic acid sequence of claim 1.

* * * * *

```
                            SEQUENCE LISTING

Sequence total quantity: 10
SEQ ID NO: 1            moltype = AA  length = 184
FEATURE                 Location/Qualifiers
source                  1..184
                        mol_type = protein
                        organism = Mycobacterium smegmatis
SEQUENCE: 1
GLDNELSLVD GQDRTLTVQQ WDTFLNGVFP LDRNRLTREW FHSGRAKYIV AGPGADEFEG   60
TLELGYQIGF PWSLGVGINF SYTTPNILID DGDITAPPFG LNSVITPNLF PGVSISADLG  120
NGPGIQEVAT FSVDVSGAEG GVAVSNAHGT VTGAAGGVLL RPFARLIAST GDSVTTYGEP  180
WNMN                                                              184

SEQ ID NO: 2            moltype = AA  length = 184
FEATURE                 Location/Qualifiers
source                  1..184
                        mol_type = protein
                        organism = Mycobacterium smegmatis
SEQUENCE: 2
GLDNELSLVD GQDRTLTVQQ WDTFLNGVFP LDRNRLTREW FHSGRAKYIV AGPGADEFEG   60
TLELGYQIGF PWSLGVGINF SYTTPNILID DGDITAPPFG LNSVITPNLF PGVSISADLG  120
NGPGIQEVAT FSVDVSGPAG GVAVSNAHGT VTGAAGGVLL RPFARLIAST GDSVTTYGEP  180
WNMN                                                              184

SEQ ID NO: 3            moltype = AA  length = 184
FEATURE                 Location/Qualifiers
source                  1..184
                        mol_type = protein
                        organism = Mycobacterium smegmatis
SEQUENCE: 3
GLDNELSLVD GQDRTLTVQQ WDTFLNGVFP LDRNRLTREW FHSGRAKYIV AGPGADEFEG   60
TLELGYQIGF PWSLGVGINF SYTTPNILID DGDITGPPFG LESVITPNLF PGVSISADLG  120
NGPGIQEVAT FSVDVSGPAG GVAVSNAHGT VTGAAGGVLL RPFARLIAST GDSVTTYGEP  180
WNMN                                                              184

SEQ ID NO: 4            moltype = AA  length = 176
FEATURE                 Location/Qualifiers
source                  1..176
                        mol_type = protein
                        organism = Mycobacterium smegmatis
SEQUENCE: 4
VDGQGRTLTV QQAETFLNGV FPLDRNRLTR EWFHSGRATY HVAGPGADEF EGTLELGYQV   60
GFPWSLGVGI NFSYTTPNIL IDGGDITQPP FGLDTIITPN LFPGVSISAD LGNGPGIQEV  120
ATFSVDVKGA KGAVAVSNAH GTVTGAAGGV LLRPFARLIA STGDSVTTYG EPWNMN      176

SEQ ID NO: 5            moltype = AA  length = 15
FEATURE                 Location/Qualifiers
```

```
REGION          1..15
                note = Synthetic construct
source          1..15
                mol_type = protein
                organism = synthetic construct
SEQUENCE: 5
GGGGSGGGGS GGGGS                                                        15

SEQ ID NO: 6            moltype = AA  length = 211
FEATURE                 Location/Qualifiers
source                  1..211
                        mol_type = protein
                        organism = Mycobacterium smegmatis
SEQUENCE: 6
MKAISRVLIA MVAAIAALFT STGTSHAGLD NELSLVDGQD RTLTVQQWDT FLNGVFPLDR   60
NRLTREWFHS GRAKYIVAGP GADEFEGTLE LGYQIGFPWS LGVGINFSYT TPNILIDDGD  120
ITAPPFGLNS VITPNLFPGV SISADLGNGP GIQEVATFSV DVSGAEGGVA VSNAHGTVTG  180
AAGGVLLRPF ARLIASTGDS VTTYGEPWNM N                                 211

SEQ ID NO: 7            moltype = AA  length = 215
FEATURE                 Location/Qualifiers
source                  1..215
                        mol_type = protein
                        organism = Mycobacterium smegmatis
SEQUENCE: 7
MTAFKRVLIA MISALLAGTT GMFVSAGAAH AGLDNELSLV DGQDRTLTVQ QWDTFLNGVF   60
PLDRNRLTRE WFHSGRAKYI VAGPGADEFE GTLELGYQIG FPWSLGVGIN FSYTTPNILI  120
DDGDITAPPF GLNSVITPNL FPGVSISADL GNGPGIQEVA TFSVDVSGPA GGVAVSNAHG  180
TVTGAAGGVL LRPFARLIAS TGDSVTTYGE PWNMN                             215

SEQ ID NO: 8            moltype = AA  length = 215
FEATURE                 Location/Qualifiers
source                  1..215
                        mol_type = protein
                        organism = Mycobacterium smegmatis
SEQUENCE: 8
MKAISRVLIA MISALAAAVA GLFVSAGTSH AGLDNELSLV DGQDRTLTVQ QWDTFLNGVF   60
PLDRNRLTRE WFHSGRAKYI VAGPGADEFE GTLELGYQIG FPWSLGVGIN FSYTTPNILI  120
DDGDITGPPF GLESVITPNL FPGVSISADL GNGPGIQEVA TFSVDVSGPA GGVAVSNAHG  180
TVTGAAGGVL LRPFARLIAS TGDSVTTYGE PWNMN                             215

SEQ ID NO: 9            moltype = AA  length = 207
FEATURE                 Location/Qualifiers
source                  1..207
                        mol_type = protein
                        organism = Mycobacterium smegmatis
SEQUENCE: 9
MRYLVMMFAL LVSVTLVSPR PANAVDNQLS VVDGQGRTLT VQQAETFLNG VFPLDRNRLT   60
REWFHSGRAT YHVAGPGADE FEGTLELGYQ VGFPWSLGVG INFSYTTPNI LIDGGDITQP  120
PFGLDTIITP NLFPGVSISA DLGNGPGIQE VATFSVDVKG AKGAVAVSNA HGTVTGAAGG  180
VLLRPFARLI ASTGDSVTTY GEPWNMN                                      207

SEQ ID NO: 10           moltype = DNA  length = 549
FEATURE                 Location/Qualifiers
source                  1..549
                        mol_type = other DNA
                        organism = Mycobacterium smegmatis
SEQUENCE: 10
ggcctggaca acgagctgag cctcgttgat ggccaggacc gcaccctcac cgtgcagcag   60
tgggacacct tcctcaatgg tgtgttcccc ctggaccgca accgtcttac ccgtgagtgg  120
ttccactccg gtcgcgccaa gtacatcgtg gccggccccg gtgccgacga gttcgagggc  180
acgctggaac tcggctacca gatcggcttc ccgtggtcgc tgggtgtggg catcaacttc  240
agctacacca ccccgaacat cctgatcgac gacggtgaca tcaccgctcc gccgttcggc  300
ctgaactcgg tcatcacccc gaacctgttc cccggtgtgt cgatctcggc agatctgggc  360
aacggccccg gcatccagga agtcgcaacg ttctcggtcg acgtctccgg cgccgagggt  420
ggcgtggccg tgtcgaacgc ccacggcacc gtgaccggtg cggccggcgg tgtgctgctg  480
cgtccgttcg cccgcctgat cgcctcgacc ggtgactcgg tcaccaccta cggcgaaccc  540
tggaacatg                                                          549
```